US008268550B2

(12) United States Patent
Chang et al.

(10) Patent No.: US 8,268,550 B2
(45) Date of Patent: Sep. 18, 2012

(54) COMPOSITIONS AND METHODS FOR IDENTIFICATION OF PARP FUNCTION, INHIBITORS, AND ACTIVATORS

(75) Inventors: Paul Chang, Cambridge, MA (US); Sejal Vyas, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 410 days.

(21) Appl. No.: 12/459,212

(22) Filed: Jun. 26, 2009

(65) Prior Publication Data

US 2010/0330583 A1 Dec. 30, 2010

(51) Int. Cl.
*G01N 33/53* (2006.01)

(52) U.S. Cl. ........................................... 435/6; 436/518

(58) Field of Classification Search ........................ None
See application file for complete search history.

(56) References Cited

U.S. PATENT DOCUMENTS

| | | | | |
|---|---|---|---|---|
| 4,704,692 | A | 11/1987 | Ladner | |
| 4,816,397 | A | 3/1989 | Boss et al. | |
| 4,816,567 | A | 3/1989 | Cabilly et al. | |
| 4,873,316 | A | 10/1989 | Meade et al. | |
| 4,946,778 | A | 8/1990 | Ladner et al. | |
| 6,277,613 | B1 | 8/2001 | De Lange et al. | |
| 6,599,728 | B2 * | 7/2003 | Morin et al. | 435/194 |
| 2002/0142334 | A1 | 10/2002 | Brown et al. | |
| 2003/0170859 | A1 | 9/2003 | Christenson et al. | |
| 2004/0115710 | A1 | 6/2004 | Li et al. | |
| 2004/0203145 | A1 | 10/2004 | Zamore et al. | |
| 2005/0037988 | A1 | 2/2005 | Zamore et al. | |
| 2005/0058982 | A1 | 3/2005 | Han et al. | |
| 2005/0153918 | A1 | 7/2005 | Chabot et al. | |
| 2006/0058255 | A1 | 3/2006 | Chen et al. | |
| 2006/0134787 | A1 | 6/2006 | Zamore et al. | |
| 2006/0167225 | A1 | 7/2006 | Gurskaya | |
| 2006/0204981 | A1 | 9/2006 | Li et al. | |
| 2007/0105114 | A1 * | 5/2007 | Li et al. | 435/6 |
| 2007/0161003 | A1 | 7/2007 | Morris et al. | |
| 2007/0179160 | A1 | 8/2007 | Helleday | |
| 2007/0264654 | A1 | 11/2007 | Wiley et al. | |
| 2008/0015144 | A1 | 1/2008 | Brownlee | |
| 2008/0076156 | A1 | 3/2008 | Inouye et al. | |
| 2008/0207555 | A1 | 8/2008 | Moss et al. | |
| 2008/0262062 | A1 | 10/2008 | Ossovskaya et al. | |
| 2009/0028861 | A1 | 1/2009 | Takagi et al. | |

FOREIGN PATENT DOCUMENTS

| | | | |
|---|---|---|---|
| WO | WO 99/64606 | | 12/1999 |
| WO | WO 01/75164 | | 10/2001 |
| WO | WO-02068579 | * | 9/2002 |
| WO | WO 2006/066048 | | 6/2006 |
| WO | WO-2008016356 | * | 2/2008 |
| WO | WO 2009/059994 | | 5/2009 |

OTHER PUBLICATIONS

MacKay et al. Genetics 2003, vol. 163, p. 1365-1373 Kuno et al. J Biol. Chem 1993, vol. 268, p. 13510-13518 Ashmun et al. Blood 1992, vol. 79, p. 3344-3349.*

Jane Reece Gillen editor, 4th edition, 1988, p. 342, p. 343, p. 442 and p. 445) Green et al. Pro. Natl. Acad. Sci. 1999 vol. 96, p. 4176-4179 Erlenbach et al. J. Biol. Chem 2001 vol. 276, p. 29382-29392.*

Noutoshi et al. Plant Journal 2005 vol. 43, p. 873-888 Bowie et al. Science, 1990 vol. 247:1306-1310.*

Shih et al. (Protein Science 2005 vol. 14, p. 936-941).*

Ame et al., "The PARP superfamily," *Bioessays* 26: 882-893 (2004).

Aravin et al., "A novel class of small RNAs bind to MILI protein in mouse testes," *Nature* 442: 203-207 (2006).

Candé et al., "Regulation of cytoplasmic stress granules by apoptosis-inducing factor," *J. Cell Sci.* 117: 4461-4468 (2004).

Chang et al., "Tankyrase-1 polymerization of poly(ADP-ribose) is required for spindle structure and function," *Nat. Cell Biol.* 7: 1133-1139 (2005).

Cohen-Armon et al., "DNA-independent PARP-1 activation by phosphorylated ERK2 increases Elk1 activity: a link to histone acetylation," *Mol. Ce1125*: 297-308 (2007).

Elbashir et al., "RNA interference is mediated by 21- and 22-nucleotide RNAs," *Genes Dev.* 15: 188-200 (2001).

Girard et al., "A germline-specific class of small RNAs binds mammalian Piwi proteins," *Nature* 442: 199-202 (2006).

Graille et al., "Crystal structure of a *Staphylococcus aureus* protein a domain complexed with the Fab fragment of a human IgM antibody: structural basis for recognition of B-cell receptors and superantigen activity," *Proc. Acad. Sci. U.S.A.* 97: 5399-5404 (2000).

Grivna et al., "A novel class of small RNAs in mouse spermatogenic cells," *Genes Dev.* 20: 1709-1714 (2006).

Haince et al., "PARP1-dependent kinetics of recruitment of MRE11 and NBS1 proteins to multiple DNA damage sites," *J. Biol. Chem.* 283: 1197-1208 (2008).

(Continued)

*Primary Examiner* — Jacob Cheu

(74) *Attorney, Agent, or Firm* — Clark & Elbing LLP; Kristina Bieker-Brady

(57) ABSTRACT

The invention provides nucleic acids encoding PARP fusion proteins, PARP fusion proteins, antibodies that bind to one or more of these PARP fusion proteins, and transgenic cells expressing one or more PARP fusion proteins. The invention also provides methods for identifying an agent as a specific PARP inhibitor or activator requiring contacting one or more PARP fusion proteins with a labeled nicotinamide adenine dinucleotide substrate and the agent and measuring the amount of labeled of ADP-ribose covalently attached to the one or more PARP fusion proteins. The invention also provides methods for identifying an agent that specifically binds to one or more PARP fusion proteins and methods for quantitating the level of one or more PARP proteins in a sample.

27 Claims, 31 Drawing Sheets
(10 of 31 Drawing Sheet(s) Filed in Color)

OTHER PUBLICATIONS

Hatakeyama et al., "Purification and characterization of poly(ADP-ribose) glycohydrolase. Different modes of action on large and small poly(ADP-ribose)," *J. Biol. Chem*. 261: 14902-14911 (1986).

Jones et al., "A novel peptide tag for detection and purification of recombinant expressed proteins," *Protein Expr. Purif.* 53: 404-410 (2007).

Kedersha et al., "Dynamic shuttling of TIA-1 accompanies the recruitment of mRNA to mammalian stress granules," *J. Cell Biol*. 151: 1257-1268 (2000).

Köhler et al., "Continuous cultures of fused cells secreting antibody of predefined specificity," *Nature* 256: 495 (1975).

Köhler et al., "Derivation of specific antibody-producing tissue culture and tumor lines by cell fusion," *Eur. J. Immunol*. 6: 511-519 (1976).

Köhler et al., "Fusion between immunoglobulin-secreting and nonsecreting myeloma cell lines," *Eur. J. Immunol*. 6: 292-295 (1976).

Lau et al., "Characterization of the piRNA complex from rat testes," *Science* 313: 363-367 (2006).

Lichty et al., "Comparison of affinity tags for protein purification," *Protein Expr. Purif.* 41:98-105 (2005).

McCafferty et al., "Phage antibodies: filamentous phage displaying antibody variable domains," *Nature* 348: 552-554 (1990).

McCaffrey et al., "RNA interference in adult mice," *Nature* 418: 38-39 (2002).

Meyer-Ficca et al., "Human poly(ADP-ribose) glycohydrolase is expressed in alternative splice variants yielding isoforms that localize to different cell compartments," *Exp. Cell. Res*. 297: 521-532 (2004).

Mocikat, "Improving the expression of chimeric antibodies following homologous recombination in hybridoma cells," *J. Immunol. Methods* 225: 185-189 (1999).

Nottbahn et al., "A colorimetric substrate for poly(ADP-ribose) polymerase-1, VPARP, and tankyrase-1," *Agnew. Chem. Int. Ed. Engl*. 46: 2066-2069 (2007).

Paddison et al., "Short hairpin RNAs (shRNAs) induce sequence-spcific silencing in mammalian cells," *Genes Dev*. 16: 948-958 (2002).

Putt et al., "An enzymatic assay for poly(ADP-ribose) polymerase-1 (PARP-1) via the chemical quantitation of NAD(+): application to the high-throughput screening of small molecules as potential inhibitors," *Anal. Biochem*. 326: 78-86 (2004).

Roben et al., "VH3 family antibodies bind domain D of staphylococcal protein A," *J. Immunol*. 154: 6437-6445 (1995).

Schagat et al., "Micro RNA biosensors: application for the psiCHECK vector," *Promega Notes* 99: 16-18 (2008).

Srikumaran et al., "Bovine x mouse hybridomas that secrete bovine immunoglobulin G1," *Science* 220: 522-523 (1983).

Tourrière et al., "The RasGAP-associated endoribonuclease G3BP assembles stress granules," *J. Cell Biol*. 160: 823-831 (2003).

Tuesday Session, The Authors Journal Compilation. International Society for Neurochemistry. *J. Neurochem*. 102: 76-147 (2007).

Turner et al., "A synthetic lethal siRNA screen identifying genes mediating sensitivity to a PARP inhibitor," *EMBO J*. 27: 1368-1377 (2008).

Ward et al., "Binding activities of a repertoire of single immunoglobulin variable domains secreted from *Escherichia coli,*" *Nature* 341: 544-546 (1989).

Yu et al., "RNA interference by expression of short-interfering RNAs and hairpin RNAs in mammalian cells," *Proc. Natl. Acad. Sci. U.S.A*. 99: 6047-6052 (2002).

International Search Report from PCT Application WO2010/151773, dated Dec. 20, 2010.

International Search Report from PCT Application WO2010/151664, dated Feb. 9, 2011.

International Search Report from PCT Application WO2010/151656, dated Jan. 12, 2011.

* cited by examiner pEGFP-C1

Polylinker Sequence (SEQ ID NO: 29):

CTGTACAAGTCCGGACTCAGATCTCGAGCTCAAGCTTCGAATTCTGCAGTCGAC 1374

BspE I Bgl II Xho I Sac I Hind III EcoR I Pst I Sal I/Acc I

GGTACCGCGGGCCCGGGATCCACCGGATCTAGATAACTGATCATAATCAGCCAT 1428

Kpn I Sac II Apa I BamH I Xba I Bcl I

Xma I/Sma I

| Marker | Organelle |
| --- | --- |
| Actin | Cytoskeleton |
| ATP Synthase | Mitochondria |
| ADP Ribosylation Factor | TGN/ Secretory Vesicles |
| Calnexin | ER |
| EEA1 | Early Endosome |
| Gamma Tubulin | Centrosome |
| GW182 | GW Bodies |
| Lamin BI | Nuclear Envelope |
| LAMP2 | Lysosome |
| Mannosidase II | Golgi |
| Tubulin | Cytoskeleton |
| Catalase | Peroxisomes |
| PSP-1 | Para Speckles |
| H2AX | Histones |
| Coilin | Cajal Bodies |

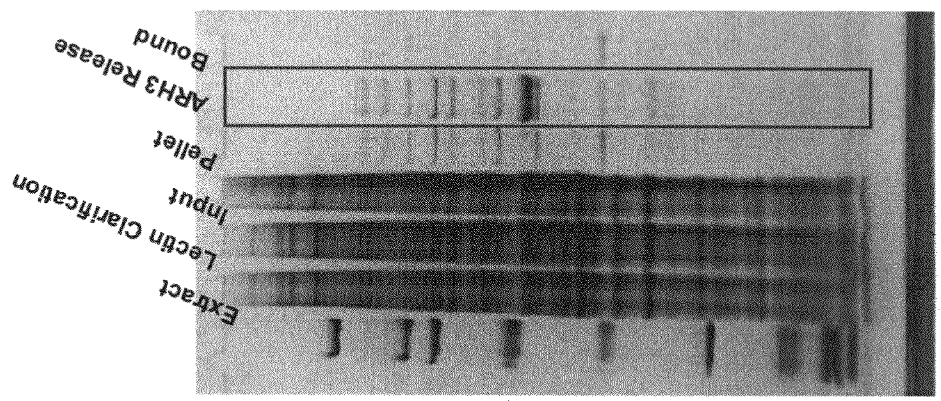
Figure 15
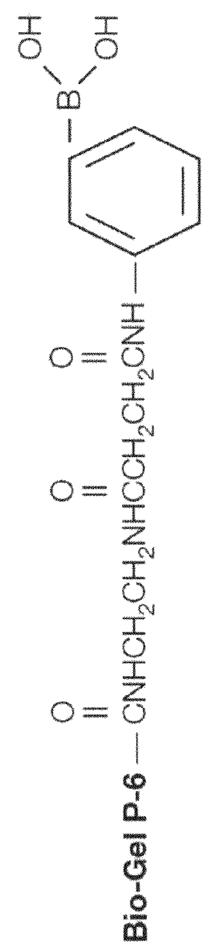

hTERT-RPE eIF3 PARP-11-GFP DAPI

G3BP Structure

SEQUENCE LISTING

```
<160> NUMBER OF SEQ ID NOS: 43

<210> SEQ ID NO 1
<211> LENGTH: 3048
<212> TYPE: DNA
<213> ORGANISM: Homo sapiens

<400> SEQUENCE: 1

aggatggcgg agtcttcgga taagctctat cgagtcgagt acgccaagag cgggcgcgcc      60

tcttgcaaga aatgcagcga gagcatcccc aaggactcgc tccggatggc catcatggtg     120

cagtcgccca tgtttgatgg aaaagtccca cactggtacc acttctcctg cttctggaag     180

gtgggccact ccatccggca ccctgacgtt gaggtggatg ggttctctga gcttcggtgg     240

gatgaccagc agaaagtcaa gaagacagcg gaagctggag gagtgacagg caaaggccag     300

gatggaattg gtagcaaggc agagaagact ctgggtgact ttgcagcaga gtatgccaag     360

tccaacagaa gtacgtgcaa ggggtgtatg gagaagatag aaaagggcca ggtgcgcctg     420

tccaagaaga tggtggaccc ggagaagcca cagctaggca tgattgaccg ctggtaccat     480

ccaggctgct ttgtcaagaa cagggaggag ctgggtttcc ggcccgagta cagtgcgagt     540

cagctcaagg gcttcagcct ccttgctaca gaggataaag aagccctgaa gaagcagctc     600

ccaggagtca agagtgaagg aaagagaaaa ggcgatgagg tggatggagt ggatgaagtg     660

gcgaagaaga aatctaaaaa agaaaaagac aaggatagta agcttgaaaa agccctaaag     720
```

```
gctcagaacg acctgatctg gaacatcaag gacgagctaa agaaagtgtg ttcaactaat    780
gacctgaagg agctactcat cttcaacaag cagcaagtgc cttctgggga gtcggcgatc    840
ttggaccgag tagctgatgg catggtgttc ggtgccctcc ttccctgcga ggaatgctcg    900
ggtcagctgg tcttcaagag cgatgcctat tactgcactg ggacgtcac tgcctggacc    960
aagtgtatgg tcaagacaca gacacccaac cggaaggagt gggtaacccc aaaggaattc   1020
cgagaaatct cttacctcaa gaaattgaag gttaaaaagc aggaccgtat attcccccca   1080
gaaaccagcg cctccgtggc ggccacgcct ccgccctcca cagcctcggc tcctgctgct   1140
gtgaactcct ctgcttcagc agataagcca ttatccaaca tgaagatcct gactctcggg   1200
aagctgtccc ggaacaagga tgaagtgaag gccatgattg agaaactcgg ggggaagttg   1260
acggggacgg ccaacaaggc ttccctgtgc atcagcacca aaaaggaggt ggaaaagatg   1320
aataagaaga tggaggaagt aaaggaagcc aacatccgag ttgtgtctga ggacttcctc   1380
caggacgtct ccgcctccac caagagcctt caggagttgt tcttagcgca catcttgtcc   1440
ccttgggggg cagaggtgaa ggcagagcct gttgaagttg tggccccaag agggaagtca   1500
ggggctgcgc tctccaaaaa aagcaagggc caggtcaagg aggaaggtat caacaaatct   1560
gaaaagagaa tgaaattaac tcttaaagga ggagcagctg tggatcctga ttctggactg   1620
gaacactctg cgcatgtcct ggagaaaggt gggaaggtct tcagtgccac ccttggcctg   1680
gtggacatcg ttaaaggaac caactcctac tacaagctgc agcttctgga ggacgacaag   1740
gaaaacaggt attggatatt caggtcctgg ggccgtgtgg gtacggtgat cggtagcaac   1800
aaactggaac agatgccgtc caaggaggat gccattgagc agttcatgaa attatatgaa   1860
gaaaaaaccg ggaacgcttg gcactccaaa aatttcacga agtatcccaa aaagttttac   1920
cccctggaga ttgactatgg ccaggatgaa gaggcagtga agaagctcac agtaaatcct   1980
ggcaccaagt ccaagctccc caagccagtt caggacctca tcaagatgat ctttgatgtg   2040
gaaagtatga agaaagccat ggtggagtat gagatcgacc ttcagaagat gcccttgggg   2100
aagctgagca aaaggcagat ccaggccgca tactccatcc tcagtgaggt ccagcaggcg   2160
gtgtctcagg gcagcagcga ctctcagatc ctggatctct caaatcgctt ttacaccctg   2220
atcccccacg actttgggat gaagaagcct ccgctcctga acaatgcaga cagtgtgcag   2280
gccaaggtgg aaatgcttga caacctgctg gacatcgagg tggcctacag tctgctcagg   2340
ggagggtctg atgatagcag caaggatccc atcgatgtca actatgagaa gctcaaaact   2400
gacattaagg tggttgacag agattctgaa gaagccgaga tcatcaggaa gtatgttaag   2460
aacactcatg caaccacaca cagtgcgtat gacttggaag tcatcgatat ctttaagata   2520
gagcgtgaag gcgaatgcca gcgttacaag ccctttaagc agcttcataa ccgaagattg   2580
ctgtggcacg ggtccaggac caccaacttt gctgggatcc tgtcccaggg tcttcggata   2640
gccccgcctg aagcgcccgt gacaggctac atgtttggta aagggatcta tttcgctgac   2700
atggtctcca agagtgccaa ctactaccat acgtctcagg gagacccaat aggcttaatc   2760
ctgttgggag aagttgccct tggaaacatg tatgaactga agcacgcttc acatatcagc   2820
aggttaccca agggcaagca cagtgtcaaa ggtttgggca aaactacccc tgatccttca   2880
gctaacatta gtctggatgg tgtagacgtt cctcttggga ccgggatttc atctggtgtg   2940
atagacacct ctctactata taacgagtac attgtctatg atattgctca ggtaaatctg   3000
aagtatctgc tgaaactgaa attcaatttt aagacctccc tgtggtaa                3048
```

<210> SEQ ID NO 2
<211> LENGTH: 1089
<212> TYPE: DNA
<213> ORGANISM: Homo sapiens

<400> SEQUENCE: 2

```
atgctcacag taaatcctgg caccaagtcc aagctcccca agccagttca ggacctcatc     60
aagatgatct ttgatgtgga aagtatgaag aaagccatgg tggagtatga gatcgacctt    120
cagaagatgc ccttggggaa gctgagcaaa aggcagatcc aggccgcata ctccatcctc    180
agtgaggtcc agcaggcggt gtctcagggc agcagcgact ctcagatcct ggatctctca    240
aatcgctttt acaccctgat cccccacgac tttgggatga agaagcctcc gctcctgaac    300
aatgcagaca gtgtgcaggc caaggtggaa atgcttgaca acctgctgga catcgaggtg    360
gcctacagtc tgctcagggg agggtctgat gatagcagca aggatcccat cgatgtcaac    420
tatgagaagc tcaaaactga cattaaggtg gttgacagag attctgaaga agccgagatc    480
atcaggaagt atgttaagaa cactcatgca accacacaca gtgcgtatga cttggaagtc    540
atcgatatct ttaagataga gcgtgaaggc gaatgccagc gttacaagcc ctttaagcag    600
cttatgcata accgaagatt gctgtggcac gggtccagga ccaccaactt tgctgggatc    660
ctgtcccagg gtcttcggat agccccgcct gaagcgcccg tgacaggcta catgtttggt    720
aaagggatct atttcgctga catggtctcc aagagtgcca actactacca tacgtctcag    780
ggagacccaa taggcttaat cctgttggga gaagttgccc ttggaaacat gtatgaactg    840
aagcacgctt cacatatcag caggttaccc aagggcaagc acagtgtcaa aggtttgggc    900
aaaactaccc ctgatccttc agctaacatt agtctggatg gtgtagacgt tcctcttggg    960
accgggattt catctggtgt gatagacacc tctctactat ataacgagta cattgtctat   1020
gatattgctc aggtaaatct gaagtatctg ctgaaactga aattcaattt taagacctcc   1080
ctgtggtaa                                                           1089
```

<210> SEQ ID NO 3
<211> LENGTH: 1716
<212> TYPE: DNA
<213> ORGANISM: Homo sapiens

<400> SEQUENCE: 3

```
gccatggcgg cgcggcggcg acggagcacc ggcggcggca gggcgagagc attaaatgaa     60
agcaaaagag ttaataatgg caacacggct ccagaagact cttcccctgc caagaaaact    120
cgtagatgcc agagacagga gtcgaaaaag atgcctgtgg ctggaggaaa agctaataag    180
gacaggacag aagacaagca agatgaatct gtgaaggcct tgctgttaaa gggcaaagct    240
cctgtggacc cagagtgtac agccaaggtg gggaaggctc atgtgtattg tgaaggaaat    300
gatgtctatg atgtcatgct aaatcagacc aatctccagt tcaacaacaa caagtactat    360
ctgattcagc tattagaaga tgatgcccag aggaacttca gtgtttggat gagatggggc    420
cgagttggga aaatgggaca gcacagcctg gtggcttgtt caggcaatct caacaaggcc    480
aaggaaatct ttcagaagaa attccttgac aaaacgaaaa acaattggga agatcgagaa    540
aagtttgaga aggtgcctgg aaaatatgat atgctacaga tggactatgc caccaatact    600
caggatgaag aggaaacaaa gaaagaggaa tctcttaaat ctcccttgaa gccagagtca    660
cagctagatc ttcgggtaca ggagttaata aagttgatct gtaatgttca ggccatggaa    720
gaaatgatga tggaaatgaa gtataatacc aagaaagccc cacttgggaa gctgacagtg    780
gcacaaatca aggcaggtta ccagtctctt aagaagattg aggattgtat tcgggctggc    840
```

```
cagcatggac gagctctcat ggaagcatgc aatgaattct acaccaggat tccgcatgac    900

tttggactcc gtactcctcc actaatccgg acacagaagg aactgtcaga aaaaatacaa    960

ttactagagg ctttgggaga cattgaaatt gctattaagc tggtgaaaac agagctacaa   1020

agcccagaac acccattgga ccaacactat agaaacctac attgtgcctt gcgcccctt    1080

gaccatgaaa gttatgagtt caaagtgatt tcccagtacc tacaatctac ccatgctccc   1140

acacacagcg actataccat gaccttgctg gatttgtttg aagtggagaa ggatggtgag   1200

aaagaagcct tcagagagga ccttcataac aggatgcttc tatggcatgg ttccaggatg   1260

agtaactggg tgggaatctt gagccatggg cttcgaattg ccccacctga agctcccatc   1320

acaggttaca tgtttgggaa aggaatctac tttgctgaca tgtcttccaa gagtgccaat   1380

tactgctttg cctctcgcct aaagaataca ggactgctgc tcttatcaga ggtagctcta   1440

ggtcagtgta atgaactact agaggccaat cctaaggccg aaggattgct tcaaggtaaa   1500

catagcacca aggggctggg caagatggct cccagttctg cccacttcgt caccctgaat   1560

gggagtacag tgccattagg accagcaagt gacacaggaa ttctgaatcc agatggttat   1620

accctcaact acaatgaata tattgtatat aaccccaacc aggtccgtat gcggtacctt   1680

ttaaaggttc agtttaattt ccttcagctg tggtga                             1716
```

<210> SEQ ID NO 4
<211> LENGTH: 1605
<212> TYPE: DNA
<213> ORGANISM: Homo sapiens

<400> SEQUENCE: 4

```
gccatggctc caaagccgaa gccctgggta cagactgagg gccctgagaa gaagaagggc     60

cggcaggcag gaagggagga ggaccccttc cgctccaccg ctgaggccct caaggccata    120

cccgcagaga agcgcataat ccgcgtggat ccaacatgtc cactcagcag caaccccggg    180

acccaggtgt atgaggacta caactgcacc ctgaaccaga ccaacatcga gaacaacaac    240

aacaagttct acatcatcca gctgctccaa gacagcaacc gcttcttcac ctgctggaac    300

cgctggggcc gtgtgggaga ggtcggccag tcaaagatca accacttcac aaggctagaa    360

gatgcaaaga aggactttga gaagaaattt cgggaaaaga ccaagaacaa ctgggcagag    420

cgggaccact ttgtgtctca cccgggcaag tacacactta tcgaagtaca ggcagaggat    480

gaggcccagg aagctgtggt gaaggtggac agaggcccag tgaggactgt gactaagcgg    540

gtgcagccct gctccctgga cccagccacg cagaagctca tcactaacat cttcagcaag    600

gagatgttca agaacaccat ggccctcatg gacctggatg tgaagaagat gcccctggga    660

aagctgagca agcaacagat tgcacggggt ttcgaggcct tggaggcgct ggaggaggcc    720

ctgaaaggcc ccacggatgg tggccaaagc ctggaggagc tgtcctcaca cttttacacc    780

gtcatcccgc acaacttcgg ccacagccag cccccgccca tcaattcccc tgagcttctg    840

caggccaaga aggacatgct gctggtgctg gcggacatcg agctggccca ggccctgcag    900

gcagtctctg agcaggagaa gacggtggag gaggtgccac accccctgga ccgagactac    960

cagcttctca agtgccagct gcagctgcta gactctggag cacctgagta caaggtgata   1020

cagacctact tagaacagac tggcagcaac cacaggtgcc ctacacttca acacatctgg   1080

aaagtaaacc aagaagggga ggaagacaga ttccaggccc actccaaact gggtaatcgg   1140

aagctgctgt ggcatggcac caacatggcc gtggtggccg ccatcctcac tagtgggctc   1200

cgcatcatgc cacattctgg tgggcgtgtt ggcaagggca tctactttgc ctcagagaac   1260
```

```
agcaagtcag ctggatatgt tattggcatg aagtgtgggg cccaccatgt cggctacatg   1320

ttcctgggtg aggtggccct gggcagagag caccatatca acacggacaa ccccagcttg   1380

aagagcccac ctcctggctt cgacagtgtc attgcccgag gccacaccga gcctgatccg   1440

acccaggaca ctgagttgga gctggatggc cagcaagtgg tggtgcccca gggccagcct   1500

gtgccctgcc cagagttcag cagctccaca ttctcccaga gcgagtacct catctaccag   1560

gagagccagt gtcgcctgcg ctacctgctg gaggtccacc tctga                   1605
```

<210> SEQ ID NO 5
<211> LENGTH: 1602
<212> TYPE: DNA
<213> ORGANISM: Homo sapiens

<400> SEQUENCE: 5

```
gccatggctc caaagccgaa gccctgggta cagactgagg gccctgagaa gaagggccgg     60

caggcaggaa gggaggagga ccccttccgc tccaccgctg aggccctcaa ggccataccc    120

gcagagaagc gcataatccg cgtggatcca acatgtccac tcagcagcaa ccccgggacc    180

caggtgtatg aggactacaa ctgcaccctg aaccagacca acatcgagaa caacaacaac    240

aagttctaca tcatccagct gctccaagac agcaaccgct tcttcacctg ctggaaccgc    300

tggggccgtg tgggagaggt cggccagtca aagatcaacc acttcacaag gctagaagat    360

gcaaagaagg actttgagaa gaaatttcgg gaaaagacca agaacaactg ggcagagcgg    420

gaccactttg tgtctcaccc gggcaagtac acacttatcg aagtacaggc agaggatgag    480

gcccaggaag ctgtggtgaa ggtggacaga ggcccagtga ggactgtgac taagcgggtg    540

cagccctgct ccctggaccc agccacgcag aagctcatca ctaacatctt cagcaaggag    600

atgttcaaga acaccatggc cctcatggac ctggatgtga agaagatgcc cctgggaaag    660

ctgagcaagc aacagattgc acggggtttc gaggccttgg aggcgctgga ggaggccctg    720

aaaggcccca cggatggtgg ccaaagcctg gaggagctgt cctcacactt ttacaccgtc    780

atcccgcaca acttcggcca cagccagccc ccgcccatca attcccctga gcttctgcag    840

gccaagaagg acatgctgct ggtgctggcg gacatcgagc tggcccaggc cctgcaggca    900

gtctctgagc aggagaagac ggtggaggag gtgccacacc ccctggaccg agactaccag    960

cttctcaagt gccagctgca gctgctagac tctggagcac ctgagtacaa ggtgatacag   1020

acctacttag aacagactgg cagcaaccac aggtgcccta cacttcaaca catctggaaa   1080

gtaaaccaag aaggggagga agacagattc caggcccact ccaaactggg taatcggaag   1140

ctgctgtggc atggcaccaa catggccgtg gtggccgcca tcctcactag tgggctccgc   1200

atcatgccac attctggtgg gcgtgttggc aagggcatct actttgcctc agagaacagc   1260

aagtcagctg gatatgttat tggcatgaag tgtggggccc accatgtcgg ctacatgttc   1320

ctgggtgagg tggccctggg cagagagcac catatcaaca cggacaaccc cagcttgaag   1380

agcccacctc ctggcttcga cagtgtcatt gcccgaggcc acaccgagcc tgatccgacc   1440

caggacactg agttggagct ggatggccag caagtggtgg tgccccaggg ccagcctgtg   1500

ccctgcccag agttcagcag ctccacattc tcccagagcg agtacctcat ctaccaggag   1560

agccagtgtc gcctgcgcta cctgctggag gtccacctct ga                      1602
```

<210> SEQ ID NO 6
<211> LENGTH: 1602
<212> TYPE: DNA
<213> ORGANISM: Homo sapiens

<400> SEQUENCE: 6

```
gccatggctc caaagccgaa gccctgggta cagactgagg gccctgagaa gaagggccgg     60
caggcaggaa gggaggagga ccccttccgc tccaccgctg aggccctcaa ggccataccc    120
gcagagaagc gcataatccg cgtggatcca acatgtccac tcagcagcaa ccccgggacc    180
caggtgtatg aggactacaa ctgcaccctg aaccagacca acatcgagaa caacaacaac    240
aagttctaca tcatccagct gctccaagac agcaaccgct tcttcacctg ctggaaccgc    300
tggggccgtg tgggagaggt cggccagtca aagatcaacc acttcacaag gctagaagat    360
gcaaagaagg actttgagaa gaaatttcgg gaaaagacca agaacaactg ggcagagcgg    420
gaccactttg tgtctcaccc gggcaagtac acacttatcg aagtacaggc agaggatgag    480
gcccaggaag ctgtggtgaa ggtggacaga ggcccagtga ggactgtgac taagcgggtg    540
cagccctgct ccctggaccc agccacgcag aagctcatca ctaacatctt cagcaaggag    600
atgttcaaga acaccatggc cctcatggac ctggatgtga agaagatgcc cctgggaaag    660
ctgagcaagc aacagattgc acggggtttc gaggccttgg aggcgctgga ggaggccctg    720
aaaggcccca cggatggtgg ccaaagcctg gaggagctgt cctcacactt ttacaccgtc    780
atcccgcaca acttcggcca cagccagccc ccgcccatca attcccctga gcttctgcag    840
gccaagaagg acatgctgct ggtgctggcg gacatcgagc tggcccaggc cctgcaggca    900
gtctctgagc aggagaagac ggtggaggag gtgccacacc ccctggaccg agactaccag    960
cttctcaagt gccagctgca gctgctagac tctggagcac ctgagtacaa ggtgatacag   1020
acctacttag aacagactgg cagcaaccac aggtgcccta cacttcaaca catctggaaa   1080
gtaaaccaag aaggggagga agacagattc caggcccact ccaaactggg taatcggaag   1140
ctgctgtggc atggcaccaa catggccgtg gtggccgcca tcctcactag tgggctccgc   1200
atcatgccac attctggtgg gcgtgttggc aagggcatct actttgcctc agagaacagc   1260
aagtcagctg gatatgttat tggcatgaag tgtggggccc accatgtcgg ctacatgttc   1320
ctgggtgagg tggccctggg cagagagcac catatcaaca cggacaaccc cagcttgaag   1380
agcccacctc ctggcttcga cagtgtcatt gcccgaggcc acaccgagcc tgatccgacc   1440
caggacactg agttggagct ggatggccag caagtggtgg tgccccaggg ccagcctgtg   1500
ccctgcccag agttcagcag ctccacattc tcccagagcg agtacctcat ctaccaggag   1560
agccagtgtc gcctgcgcta cctgctggag gtccacctct ga                      1602
```

<210> SEQ ID NO 7
<211> LENGTH: 5178
<212> TYPE: DNA
<213> ORGANISM: Homo sapiens

<400> SEQUENCE: 7

```
aggatggtga tgggaatctt tgcaaattgt atcttctgtt tgaaagtgaa gtacttacct     60
cagcagcaga agaaaaagct acaaactgac attaaggaaa atggcggaaa gttttccttt    120
tcgttaaatc ctcagtgcac acatataatc ttagataatg ctgatgttct gagtcagtac    180
caactgaatt ctatccaaaa gaaccacgtt catattgcaa acccagattt tatatggaaa    240
tctatcagag aaaagagact cttggatgta aagaattatg atccttataa gcccctggac    300
atcacaccac ctcctgatca gaaggcgagc agttctgaag tgaaaacaga aggtctatgc    360
ccggacagtg ccacagagga ggaagacact gtggaactca ctgagtttgg tatgcagaat    420
gttgaaattc ctcatcttcc tcaagatttt gaagttgcaa aatataacac cttggagaaa    480
```

```
gtgggaatgg agggaggcca ggaagctgtg gtggtggagc ttcagtgttc gcgggactcc    540
agggactgtc ctttcctgat atcctcacac ttcctcctgg atgatggcat ggagactaga    600
agacagtttg ctataaagaa aacctctgaa gatgcaagtg aatactttga aaattacatt    660
gaagaactga agaaacaagg atttctacta agagaacatt tcacacctga agcaacccaa    720
ttagcatctg aacaattgca agcattgctt ttggaggaag tcatgaattc aagcactctg    780
agccaagagg tgagcgattt agtagagatg atttgggcag aggccctggg ccacctggaa    840
cacatgcttc tcaagccagt gaacaggatt agcctcaacg atgtgagcaa ggcagagggg    900
attctccttc tagtaaaggc agcactgaaa aatggagaaa cagcagagca attgcaaaag    960
atgatgacag agttttacag actgatacct cacaaaggca caatgcccaa agaagtgaac   1020
ctgggactat tggctaagaa agcagacctc tgccagctaa taagagacat ggttaatgtc   1080
tgtgaaacta atttgtccaa acccaaccca ccatccctgg ccaaataccg agctttgagg   1140
tgcaaaattg agcatgttga acagaatact gaagaatttc tcagggttag aaaagaggtt   1200
ttgcagaatc atcacagtaa gagcccagtg gatgtcttgc agatatttag agttggcaga   1260
gtgaatgaaa ccacagagtt tttgagcaaa cttggtaatg tgaggccctt gttgcatggt   1320
tctcctgtac aaaacatcgt gggaatcttg tgtcgagggt tgcttttacc caaagtagtg   1380
gaagatcgtg gtgtgcaaag aacagacgtc ggaaaccttg gaagtgggat ttatttcagt   1440
gattcgctca gtacaagtat caagtactca cacccgggag agacagatgg caccagactc   1500
ctgctcattt gtgacgtagc cctcggaaag tgtatggact tacatgagaa ggactttccc   1560
ttaactgaag caccaccagg ctacgacagt gtgcatggag tttcacaaac agcctctgtc   1620
accacagact ttgaggatga tgaatttgtt gtctataaaa ccaatcaggt taaaatgaaa   1680
tatattatta aattttccat gcctggagat cagataaagg actttcatcc tagtgatcat   1740
actgaattag aggaatacag acctgagttt tcaaattttt caaaggttga agattaccag   1800
ttaccagatg ccaaaacttc cagcagcacc aaggccggcc tccaggatgc ctctgggaac   1860
ttggttcctc tggaggatgt ccacatcaaa gggagaatca tagacactgt agcccaggtc   1920
attgtttttc agacatacac aaataaaagt cacgtgccca ttgaggcaaa atatatcttt   1980
cctttggatg acaaggccgc tgtgtgtggc ttcgaagcct tcatcaatgg gaagcacata   2040
gttggagaga ttaaagagaa ggaagaagcc cagcaagagt acctagaagc cgtgacccag   2100
ggccatggcg cttacctgat gagtcaggat gctccggacg tttttactgt aagtgttgga   2160
aacttacccc ctaaggctaa ggttcttata aaaattacct acatcacaga actcagcatc   2220
ctgggcactg ttggtgtctt tttcatgccc gccaccgtag caccctggca acaggacaag   2280
gctttgaatg aaaaccttca ggatacagta gagaagattt gtataaaaga aataggaaca   2340
aagcaaagct tctctttgac tatgtctatt gagatgccgt atgtgattga attcattttc   2400
agtgatacac atgaactgaa acaaaagcgc acagactgca aagctgtcat tagcaccatg   2460
gaaggcagct ccttagacag cagtggattt tctctccaca tcggtttgtc tgctgcctat   2520
ctcccaagaa tgtgggttga aaaacatcca gaaaaagaaa gcgaggcttg catgcttgtc   2580
tttcaacccg atctcgatgt cgacctccct gacctagcca gtgagagcga agtgattatt   2640
tgtcttgact gctccagttc catggagggt gtgacattct tgcaagccaa gcaaatcacc   2700
ttgcatgcgc tgtccttggt gggtgagaag cagaaagtaa atattatcca gttcggcaca   2760
ggttacaagg agctattttc gtatcctaag catatcacaa gcaataccac ggcagcagag   2820
ttcatcatgt ctgccacacc taccatgggg aacacagact tctggaaaac actccgatat   2880
```

-continued

```
cttagcttat tgtaccctgc tcgagggtca cggaacatcc tcctggtgtc tgatgggcac   2940
ctccaggatg agagcctgac attacagctc gtgaagagga gccgcccgca caccaggtta   3000
ttcgcctgcg gtatcggttc tacagcaaat cgtcacgtct taaggatttt gtcccagtgt   3060
ggtgccggag tatttgaata ttttaatgca aaatccaagc atagttggag aaaacagata   3120
gaagaccaaa tgaccaggct atgttctccg agttgccact ctgtctccgt caaatggcag   3180
caactcaatc cagatgcgcc cgaggccctg caggccccag cccaggtgcc atccttgttt   3240
cgcaatgatc gactccttgt ctatggattc attcctcact gcacacaagc aactctgtgt   3300
gcactaattc aagagaaaga attttgtaca atggtgtcga ctactgagct tcagaagaca   3360
actggaacta tgatccacaa gctggcagcc cgagctctaa tcagagatta tgaagatggc   3420
attcttcacg aaaatgaaac cagtcatgag atgaaaaaac aaaccttgaa atctctgatt   3480
attaaactca gtaaagaaaa ctctctcata acacaattta caagctttgt ggcagttgag   3540
aaaagggatg agaatgagtc gccttttcct gatattccaa aagtttctga acttattgcc   3600
aaagaagatg tagacttcct gccctacatg agctggcagg gggagcccca agaagccgtc   3660
aggaaccagt ctcttttagc atcctctgag tggccagaat tacgtttatc caaacgaaaa   3720
cataggaaaa ttccattttc caaaagaaaa atggaattat ctcagccaga agtttctgaa   3780
gattttgaag aggatggctt aggtgtacta ccagctttca catcaaattt ggaacgtgga   3840
ggtgtggaaa agctattgga tttaagttgg acagagtcat gtaaaccaac agcaactgaa   3900
ccactattta agaaagtcag tccatgggaa acatctactt ctagcttttt tcctattttg   3960
gctccggccg ttggttccta tcttaccccg actacccgcg ctcacagtcc tgcttccttg   4020
tcttttgcct catatcgtca ggtagctagt ttcggttcag ctgctcctcc cagacagttt   4080
gatgcatctc aattcagcca aggccctgtg cctggcactt gtgctgactg gatcccacag   4140
tcggcgtctt gtcccacagg acctccccag aacccacctt ctgcacccta ttgtggcatt   4200
gtttttttcag ggagctcatt aagctctgca cagtctgctc cactgcaaca tcctggaggc   4260
tttactacca ggccttctgc tggcaccttc cctgagctgg attctcccca gcttcatttc   4320
tctcttccta cagaccctga tcccatcaga ggttttgggt cttatcatcc ctctgcttac   4380
tctccttttc attttcaacc ttccgcagcc tctttgactg ccaaccttag gctgccaatg   4440
gcctctgctt tacctgaggc tctttgcagt cagtcccgga ctaccccagt agatctctgt   4500
cttctagaag aatcagtagg cagtctcgaa ggaagtcgat gtcctgtctt tgcttttcaa   4560
agttctgaca cagaaagtga tgagctatca gaagtacttc aagacagctg ctttttacaa   4620
ataaagtgtg atacaaaaga tgacagtatc ccgtgctttc tggaattaaa agaagaggat   4680
gaaatagtgt gcacacaaca ctggcaggat gctgtgcctt ggacagaact cctcagtcta   4740
cagacagagg atggcttctg gaaacttaca ccagaactgg gacttatatt aaatcttaat   4800
acaaatggtt tgcacagctt tcttaaacaa aaaggcattc aatctctagg tgtaaaagga   4860
agagaatgtc tcctggacct aattgccaca atgctggtac tacagtttat tcgcaccagg   4920
ttggaaaaag agggaatagt gttcaaatca ctgatgaaaa tggatgaccc ttctatttcc   4980
aggaatattc cctgggcttt tgaggcaata aagcaagcaa gtgaatgggt aagaagaact   5040
gaaggacagt acccatctat ctgcccacgg cttgaactgg ggaacgactg ggactctgcc   5100
accaagcagt tgctgggact ccagcccata agcactgtgt cccctcttca tagagtcctc   5160
cattacagtc aaggctaa                                                 5178
```

<210> SEQ ID NO 8
<211> LENGTH: 3987
<212> TYPE: DNA
<213> ORGANISM: Homo sapiens

<400> SEQUENCE: 8

```
aagatggcgg cgtcgcgtcg ctctcagcat catcaccacc atcatcaaca acagctccag     60
cccgccccag gggcttcagc gccgccgccg ccacctcctc ccccactcag ccctggcctg    120
gccccgggga ccaccccagc ctctcccacg gccagcggcc tggccccctt cgcctccccg    180
cggcacggcc tagcgctgcc ggagggggat ggcagtcggg atccgcccga caggccccga    240
tccccggacc cggttgacgg taccagctgt tgcagtacca ccagcacaat ctgtaccgtc    300
gccgccgctc ccgtggtccc agcggtttct acttcatctg ccgctggggt cgctcccaac    360
ccagccggca gtggcagtaa caattcaccg tcgtcctctt cttccccgac ttcttcctca    420
tcttcctctc catcctcccc tggatcgagc ttggcggaga gccccgaggc ggccggagtt    480
agcagcacag caccactggg gcctggggca gcaggacctg ggacaggggt cccagcagtg    540
agcggggccc tacgggaact gctggaggcc tgtcgcaatg ggacgtgtc ccgggtaaag    600
aggctggtgg acgcggcaaa cgtaaatgca aaggacatgg ccggccggaa gtcttctccc    660
ctgcacttcg ctgcaggttt tggaaggaag gatgttgtag aacacttact acagatgggt    720
gctaatgtcc acgctcgtga tgatggaggt ctcatcccgc ttcataatgc ctgttctttt    780
ggccatgctg aggttgtgag tctgttattg tgccaaggag ctgatccaaa tgccagggat    840
aactggaact atacacctct gcatgaagct gctattaaag ggaagatcga tgtgtgcatt    900
gtgctgctgc agcacggagc tgacccaaac attcggaaca ctgatgggaa atcagccctg    960
gacctggcag atccttcagc aaaagctgtc cttacaggtg aatacaagaa agacgaactc   1020
ctagaagctg ctaggagtgg taatgaagaa aaactaatgg ctttactgac tcctctaaat   1080
gtgaattgcc atgcaagtga tgggcgaaag tcgactcctt tacatctagc agcgggctac   1140
aacagagttc gaatagttca gcttcttctt cagcatggtg ctgatgttca tgcaaaagac   1200
aaaggtggac ttgtgcctct tcataatgca tgttcatatg gacattatga agtcacagaa   1260
ctgctactaa agcatggagc ttgtgttaat gccatggatc tctggcagtt tactccactg   1320
cacgaggctg cttccaagaa ccgtgtagaa gtctgctctt tgttacttag ccatggcgct   1380
gatcctacgt tagtcaactg ccatggcaaa agtgctgtgg atatggctcc aactccggag   1440
cttagggaga gattgactta tgaatttaaa ggtcattctt tactacaagc agccagagaa   1500
gcagacttag ctaaagttaa aaaaacactc gctctggaaa tcattaattt caaacaaccg   1560
cagtctcatg aaacagcact gcactgtgct gtggcctctc tgcatcccaa acgtaaacaa   1620
gtgacagaat tgttacttag aaaaggagca aatgttaatg aaaaaaataa agatttcatg   1680
actcccctgc atgttgcagc cgaaagagcc cataatgatg tcatggaagt tctgcataag   1740
catggcgcca agatgaatgc actggacacc cttggtcaga ctgctttgca tagagccgcc   1800
ctagcaggcc acctgcagac ctgccgcctc ctgctgagtt acggctctga cccctccatc   1860
atctccttac aaggcttcac agcagcacag atgggcaatg aagcagtgca gcagattctg   1920
agtgagagta cacctatacg tacttctgat gttgattatc gactcttaga ggcatctaaa   1980
gctggagact tggaaactgt gaagcaactt tgcagctctc aaaatgtgaa ttgtagagac   2040
ttagagggcc ggcattccac gcccttacac ttcgcagcag gctacaaccg cgtgtctgtt   2100
gtagagtacc tgctacacca cggtgccgat gtccatgcca aagacaaggg tggcttggtg   2160
ccccttcata atgcctgttc atatggacac tatgaggtgg ctgagctttt agtaaggcat   2220
```

```
ggggcttctg tcaatgtggc ggacttatgg aaatttaccc ctctccatga agcagcagct   2280

aaaggaaagt atgaaatctg caagctcctt ttaaaacatg gagcagatcc aactaaaaag   2340

aacagagatg gaaatacacc tttggatttg gtaaaggaag gagacacaga tattcaggac   2400

ttactgaaag gggatgctgc tttgttggat gctgccaaga agggctgcct ggcaagagtg   2460

cagaagctct gtaccccaga gaatatcaac tgcagagaca cccagggcag aaattcaacc   2520

cctctgcacc tggcagcagg ctataataac ctggaagtag ctgaatatct tctagagcat   2580

ggagctgatg ttaatgccca ggacaagggt ggtttaattc ctcttcataa tgcggcatct   2640

tatgggcatg ttgacatagc ggctttattg ataaaataca acacgtgtgt aaatgcaaca   2700

gataagtggg cgtttactcc cctccatgaa gcagcccaga aaggaaggac gcagctgtgc   2760

gccctcctcc tagcgcatgg tgcagacccc accatgaaga accaggaagg ccagacgcct   2820

ctggatctgg caacagctga cgatatcaga gctttgctga tagatgccat gcccccagag   2880

gccttaccta cctgttttaa acctcaggct actgtagtga gtgcctctct gatctcacca   2940

gcatccaccc cctcctgcct ctcggctgcc agcagcatag acaacctcac tggcccttta   3000

gcagagttgg ccgtaggagg agcctccaat gcaggggatg gcgccgcggg aacagaaagg   3060

aaggaaggag aagttgctgg tcttgacatg aatatcagcc aatttctaaa aagccttggc   3120

cttgaacacc ttcgggatat ctttgaaaca gaacagatta cactagatgt gttggctgat   3180

atgggtcatg aagagttgaa agaaataggc atcaatgcat atgggcaccg ccacaaatta   3240

atcaaaggag tagaaagact cttaggtgga caacaaggca ccaatcctta tttgactttt   3300

cactgtgtta atcagggaac gattttgctg gatcttgctc cagaagataa agaatatcag   3360

tcagtggaag aagagatgca aagtactatt cgagaacaca gagatggtgg taatgctggc   3420

ggcatcttca acagatacaa tgtcattcga attcaaaaag ttgtcaacaa gaagttgagg   3480

gagcggttct gccaccgaca gaaggaagtg tctgaggaga atcacaacca tcacaatgag   3540

cgcatgttgt ttcatggttc tcctttcatt aatgccatta ttcataaagg gtttgatgag   3600

cgacatgcat acataggagg aatgtttggg gccgggattt attttgctga aaactcctca   3660

aaaagcaacc aatatgttta tggaattgga ggaggaacag gctgccctac acacaaggac   3720

aggtcatgct atatatgtca cagacaaatg ctcttctgta gagtgaccct tgggaaatcc   3780

tttctgcagt ttagcaccat gaaaatggcc cacgcgcctc cagggcacca ctcagtcatt   3840

ggtagaccga gcgtcaatgg gctggcatat gctgaatatg tcatctacag aggagaacag   3900

gcatacccag agtatcttat cacttaccag atcatgaagc cagaagcccc ttcccagacc   3960

gcaacagccg cagagcagaa gacctag                                        3987
```

<210> SEQ ID NO 9
<211> LENGTH: 729
<212> TYPE: DNA
<213> ORGANISM: Homo sapiens

<400> SEQUENCE: 9

```
atgttaggtg gacaacaagg caccaatcct tatttgactt ttcactgtgt taatcaggga     60

acgattttgc tggatcttgc tccagaagat aaagaatatc agtcagtgga agaagagatg    120

caaagtacta ttcgagaaca cagagatggt ggtaatgctg gcggcatctt caacagatac    180

aatgtcattc gaattcaaaa agttgtcaac aagaagttga gggagcggtt ctgccaccga    240

cagaaggaag tgtctgagga gaatcacaac catcacaatg agcgcatgtt gtttcatggt    300

tctcctttca ttaatgccat tattcataaa gggtttgatg agcgacatgc atacatagga    360
```

ggaatgtttg gggccgggat ttattttgct gaaaactcct caaaaagcaa ccaatatgtt 420
tatggaattg gaggaggaac aggctgccct acacacaagg acaggtcatg ctatatatgt 480
cacagacaaa tgctcttctg tagagtgacc cttgggaaat cctttctgca gtttagcacc 540
atgaaaatgg cccacgcgcc tccagggcac cactcagtca ttggtagacc gagcgtcaat 600
gggctggcat atgctgaata tgtcatctac agaggagaac aggcataccc agagtatctt 660
atcacttacc agatcatgaa gccagaagcc ccttcccaga ccgcaacagc cgcagagcag 720
aagacctag 729

<210> SEQ ID NO 10
<211> LENGTH: 3504
<212> TYPE: DNA
<213> ORGANISM: Homo sapiens

<400> SEQUENCE: 10
atcatgtcgg gtcgccgctg cgccggcggg ggagcggcct gcgcgagcgc cgcggccgag 60
gccgtggagc cggccgcccg agagctgttc gaggcgtgcc gcaacgggga cgtggaacga 120
gtcaagaggc tggtgacgcc tgagaaggtg aacagccgcg acacggcggg caggaaatcc 180
accccgctgc acttcgccgc aggttttggg cggaaagacg tagttgaata tttgcttcag 240
aatggtgcaa atgtccaagc acgtgatgat gggggcctta ttcctcttca taatgcatgc 300
tcttttggtc atgctgaagt agtcaatctc cttttgcgac atggtgcaga ccccaatgct 360
cgagataatt ggaattatac tcctctccat gaagctgcaa ttaaaggaaa gattgatgtt 420
tgcattgtgc tgttacagca tggagctgag ccaaccatcc gaaatacaga tggaaggaca 480
gcattggatt tagcagatcc atctgccaaa gcagtgctta ctggtgaata taagaaagat 540
gaactcttag aaagtgccag gagtggcaat gaagaaaaaa tgatggctct actcacacca 600
ttaaatgtca actgccacgc aagtgatggc agaaagtcaa ctccattaca tttggcagca 660
ggatataaca gagtaaagat tgtacagctg ttactgcaac atggagctga tgtccatgct 720
aaagataaag gtgatctggt accattacac aatgcctgtt cttatggtca ttatgaagta 780
actgaacttt tggtcaagca tggtgcctgt gtaaatgcaa tggacttgtg gcaattcact 840
cctcttcatg aggcagcttc taagaacagg gttgaagtat gttctcttct cttaagttat 900
ggtgcagacc caacactgct caattgtcac aataaaagtg ctatagactt ggctcccaca 960
ccacagttaa aagaaagatt agcatatgaa tttaaaggcc actcgttgct gcaagctgca 1020
cgagaagctg atgttactcg aatcaaaaaa catctctctc tggaaatggt gaatttcaag 1080
catcctcaaa cacatgaaac agcattgcat tgtgctgctg catctccata tcccaaaaga 1140
aagcaaatat gtgaactgtt gctaagaaaa ggagcaaaca tcaatgaaaa gactaaagaa 1200
ttcttgactc ctctgcacgt ggcatctgag aaagctcata atgatgttgt tgaagtagtg 1260
gtgaaacatg aagcaaaggt taatgctctg gataatcttg gtcagacttc tctacacaga 1320
gctgcatatt gtggtcatct acaaacctgc cgcctactcc tgagctatgg gtgtgatcct 1380
aacattatat cccttcaggg ctttactgct ttacagatgg gaaatgaaaa tgtacagcaa 1440
ctcctccaag agggtatctc attaggtaat tcagaggcag acagacaatt gctggaagct 1500
gcaaaggctg gagatgtcga aactgtaaaa aaactgtgta ctgttcagag tgtcaactgc 1560
agagacattg aagggcgtca gtctacacca cttcattttg cagctgggta taacagagtg 1620
tccgtggtgg aatatctgct acagcatgga gctgatgtgc atgctaaaga taaaggaggc 1680
cttgtacctt tgcacaatgc atgttcttat ggacattatg aagttgcaga acttcttgtt 1740

```
aaacatggag cagtagttaa tgtagctgat ttatggaaat ttacaccttt acatgaagca   1800

gcagcaaaag gaaaatatga aatttgcaaa cttctgctcc agcatggtgc agaccctaca   1860

aaaaaaaaca gggatggaaa tactcctttg gatcttgtta aagatggaga tacagatatt   1920

caagatctgc ttaggggaga tgcagctttg ctagatgctg ccaagaaggg ttgtttagcc   1980

agagtgaaga agttgtcttc tcctgataat gtaaattgcc gcgataccca aggcagacat   2040

tcaacacctt tacatttagc agctggttat aataatttag aagttgcaga gtatttgtta   2100

caacacggag ctgatgtgaa tgcccaagac aaaggaggac ttattccttt acataatgca   2160

gcatcttacg ggcatgtaga tgtagcagct ctactaataa agtataatgc atgtgtcaat   2220

gccacggaca aatgggcttt cacacctttg cacgaagcag cccaaaaggg acgaacacag   2280

ctttgtgctt tgttgctagc ccatggagct gacccgactc ttaaaaatca ggaaggacaa   2340

acacctttag atttagtttc agcagatgat gtcagcgctc ttctgacagc agccatgccc   2400

ccatctgctc tgccctcttg ttacaagcct caagtgctca atggtgtgag aagcccagga   2460

gccactgcag atgctctctc ttcaggtcca tctagcccat caagcctttc tgcagccagc   2520

agtcttgaca acttatctgg gagtttttca gaactgtctt cagtagttag ttcaagtgga   2580

acagagggtg cttccagttt ggagaaaaag gaggttccag gagtagattt tagcataact   2640

caattcgtaa ggaatcttgg acttgagcac ctaatggata tatttgagag agaacagatc   2700

actttggatg tattagttga gatggggcac aaggagctga aggagattgg aatcaatgct   2760

tatggacata ggcacaaact aattaaagga gtcgagagac ttatctccgg acaacaaggt   2820

cttaacccat atttaacttt gaacacctct ggtagtggaa caattcttat agatctgtct   2880

cctgatgata aagagtttca gtctgtggag gaagagatgc aaagtacagt tcgagagcac   2940

agagatggag gtcatgcagg tggaatcttc aacagataca atattctcaa gattcagaag   3000

gtttgtaaca agaaactatg ggaaagatac actcaccgga gaaaagaagt ttctgaagaa   3060

aaccacaacc atgccaatga acgaatgcta tttcatgggt ctccttttgt gaatgcaatt   3120

atccacaaag gctttgatga aaggcatgcg tacataggtg gtatgtttgg agctggcatt   3180

tattttgctg aaaactcttc caaaagcaat caatatgtat atggaattgg aggaggtact   3240

gggtgtccag ttcacaaaga cagatcttgt tacatttgcc acaggcagct gctcttttgc   3300

cgggtaacct tgggaaagtc tttcctgcag ttcagtgcaa tgaaaatggc acattctcct   3360

ccaggtcatc actcagtcac tggtaggccc agtgtaaatg gcctagcatt agctgaatat   3420

gttatttaca gaggagaaca ggcttatcct gagtatttaa ttacttacca gattatgagg   3480

cctgaaggta tggtcgatgg ataa                                          3504
```

<210> SEQ ID NO 11
<211> LENGTH: 1563
<212> TYPE: DNA
<213> ORGANISM: Homo sapiens

<400> SEQUENCE: 11

```
ccaatggaca tcaaaggcca gttctggaat gatgacgact cggagggaga taatgaatca     60

gaggaatttc tctatggcgt tcaggggaac tgtgcagccg acctgtatcg acacccacag    120

cttgatgcag acattgaagc cgtgaaggag atctacagtg agaactctgt atccatcaga    180

gaatatggaa ctatcgatga cgtggacatt gacctccaca tcaacatcag cttcctcgat    240

gaggaagtct ctacagcctg gaaggtcctc cggacagaac ctattgtgtt gaggctgcga    300

ttttctctct cccagtacct agatggacca gaaccatcca ttgaggtttt ccagccatca    360
```

```
aataaggaag gatttgggct gggtcttcag ttgaaaaaga tcctgggtat gtttacatcc    420

caacaatgga aacatctgag caatgatttc ttgaagaccc agcaggagaa gaggcacagt    480

tggttcaagg caagtggtac catcaagaag ttccgagctg gcctcagcat cttttcaccc    540

atccccaagt ctcccagttt ccctatcata caggactcca tgctgaaagg caaactaggt    600

gtaccagagc ttcgggttgg gcgcctcatg aaccgttcca tctcctgtac catgaagaac    660

cccaaagtgg aagtgtttgg ctaccctccc agcccccagg caggtctcct gtgccctcag    720

cacgtgggcc tccctccccc agcacggacc tctcctttgg tcagtggtca ctgcaagaac    780

attcccactc tggagtatgg attcctcgtt cagatcatga agtatgcaga acagaggatt    840

ccaacattga atgagtactg tgtggtgtgt gatgagcagc atgtcttcca aaatggatct    900

atgctgaagc cagctgtctg tactcgtgaa ctatgcgttt tctccttcta cacactgggc    960

gtcatgtctg gagctgcaga ggaggtggcc actggagcag aggtggtgga tctgctggtg   1020

gccatgtgta gggcagcttt agagtcccct agaaagagca tcatctttga gccttatccc   1080

tctgtggtgg accccactga tcccaagact ctggccttta accctaagaa gaagaattat   1140

gagcggcttc agaaagctct ggatagtgtg atgtctattc gggagatgac ccagggctca   1200

tatttggaaa tcaagaaaca gatggacaag ttggatcccc tggcccatcc tctcctgcag   1260

tggatcatct ctagcaacag gtcacacatt gtcaaactac ctctcagcag gcagctgaag   1320

ttcatgcaca cctcacacca gttcctcctg ctgagcagcc ctcctgccaa ggaggctcgg   1380

ttccggaccg ccaagaagct ctatggcagc acctttgcct tccatgggtc ccacattgag   1440

aactggcatt cgatcctgcg caatgggctg gtcaatgcat cctacaccaa actgcaggaa   1500

tgggaaaagg acagcacagg atgccctcca aggatgagct ggtccagaga tacaacagga   1560

tga                                                                 1563
```

```
<210> SEQ ID NO 12
<211> LENGTH: 1977
<212> TYPE: DNA
<213> ORGANISM: Homo sapiens

<400> SEQUENCE: 12
```

```
attatggaaa tggaaaccac cgaacctgag ccagactgtg tagtgcagcc tccctctcct     60

cctgatgact tttcatgcca aatgagactc tctgagaaga tcactccatt gaagacttgt    120

tttaagaaaa aggatcagaa aagattggga actggaaccc tgaggtcttt gaggccaata    180

ttaaacactc ttctagaatc tggctcactt gatggggttt ttagatctag gaaccagagt    240

acagatgaga acagcttaca tgaacctatg atgaagaaag ccatggaaat caattcatca    300

tgcccaccag cagaaaataa tatgtctgtt ctgattcctg ataggacaaa tgttggggac    360

cagataccgg aagcccatcc ttccactgaa gctccagaac gagtggttcc aatccaagat    420

cacagctttc catcagaaac cctcagtggg acggtggcag attccacacc agctcacttc    480

cagactgatc ttttgcaccc agtttcaagt gatgttccta ctagtcctga ctgcttagac    540

aaagtcatag attatgttcc aggcattttc caagaaaaca gttttacaat ccaatacatt    600

ctggacacca gtgataagct gagtactgag ctctttcagg acaaaagtga agaggcttcc    660

cttgacctcg tgtttgagct ggtgaaccag ttgcagtacc acactcacca agagaacgga    720

attgaaattt gcatggactt tctgcaaggc acttgtattt atggcaggga ttgtttgaag    780

caccacactg tcttgccata tcattggcag atcaaaagga caactactca aaagtggcag    840

agtgtattca atgattctca ggagcacttg gaaagatttt actgtaaccc agaaaatgat    900
```

```
agaatgagaa tgaagtatgg aggacaagaa ttttgggcag atttgaatgc catgaacgtg    960
tatgaaacaa ctgaatttga ccaactacga aggctgtcca caccaccctc tagcaatgtc   1020
aactctattt accacacagt ctggaaattc ttctgtaggg accactttgg atggagagag   1080
tatcccgagt ctgtcattcg attgattgaa gaagccaact ctcggggtct gaaagaggtt   1140
cgatttatga tgtggaataa ccactacatc ctccacaatt cattcttcag gagagagata   1200
aaaaggagac ccctcttccg ctcctgtttt atactgcttc catatttaca gacacttggt   1260
ggggttccca cacaagctcc tccacctctt gaagcaactt catcatcaca aattatctgc   1320
ccagatgggg tcacttcagc aaacttttac cctgaaactt gggtttatat gcatccatct   1380
caggacttca tccaagtccc tgtttctgca gaggataaaa gttatcggat catttacaat   1440
ctttttcata agactgtgcc tgagtttaaa tacagaattt tgcagatatt gagagtccaa   1500
aaccagtttc tttgggagaa atataaaagg aaaaaggaat atatgaacag gaaaatgttt   1560
ggccgtgaca ggataataaa tgagagacat ttatttcatg gaacatccca ggatgtggta   1620
gatggaatct gcaaacacaa ctttgaccct cgagtctgtg gaaagcatgc tacaatgttt   1680
ggacaaggca gttattttgc aaagaaggca agctactctc ataacttttc taagaagtcc   1740
tccaaaggag tccacttcat gtttctggcc aaagtgctga cgggcagata cacaatgggc   1800
agtcatggca tgagaaggcc cccgccagtc aatcctggca gtgtcaccag tgacctttat   1860
gactcttgtg tggataattt ctttgagcct cagattttg tcatttttaa tgatgaccag    1920
agttaccctt attttgttat ccaatatgaa gaagtcagta acactgtttc catttga      1977
```

<210> SEQ ID NO 13
<211> LENGTH: 2568
<212> TYPE: DNA
<213> ORGANISM: Homo sapiens

<400> SEQUENCE: 13

```
ttaatgggga tgtgttcaag gcaagagcga attcagaagg atatcgacgt cgtgatccag     60
aagtccagag ctgagaagga ctgcctgttt gcagatttca gatactctga ctccaccttt    120
acttttacct acgttggcgg ccccagaagt gtatcctact cagtacatgt atctgaagat    180
tacccagata atacatatgt gtcaagttca gagaatgatg aagatgtgct agttactaca    240
gagccaatac cagtaatttt tcatagaata gcaacagaat taagaaaaac aaatgacatt    300
aactgttgct tatccataaa atccaaatta caaaaggaaa atggggagga atcaagacag    360
aatagtacag tggaggaaga ttctgaaggt gacaatgatt ccgaagaatt ttattacgga    420
ggacaggtga actatgatgg ggaactgcac aagcacccac aactggaagc tgatttgtca    480
gcagttagag agatatatgg gccacatgca gtttctctca gggaatatgg agccattgat    540
gatgtagata ttgatctgca tatcgatgtt agctttcttg atgaggagat tgctgtggct    600
tgggaagtaa ttcgaacaga acctataatt gttcgactac actgttcact tacacagtat    660
ttaaatggcc cagtgcccac tgttgatgtc tttcagattt ccacaaaaga gcgatttgga    720
ttgggacatc agctgaaaaa aatcatgcag acatttgtta cacagcagtg gaaacagagc    780
aaagaaaaat ccaattgcct gcacaataaa aagttgtcag agaagaaagt gaagtctccc    840
ctgcatttat tttctacttt gcgcaggtcg ccaagttatc ctccccctgg ttgtggcaaa    900
agcaaatcca aactgaaatc tgagcaggac ggaatctcca aaacgcataa gctgctgcgg    960
aggacttgtt ccagcacagt caagactgat gatgtgtgtg tcacaaagtc acacaggacc   1020
tttggccgct ccttgtccag cgatcccagg gcggagcagg ctatgacagc aattaaatcg   1080
```

```
cacaaacttt tgaaccgtcc ttgccctgca gctgttaagt cagaggaatg cctaactcta   1140

aagtcgcata gactattgac tcgatcttgt tctggagatc cacgatgtga gcacaacaca   1200

aacttgaagc cccataaact gttaagcagg tcttactcta gtaatctcag aatggaagaa   1260

ttatatggac tgaaaaatca caaattgctc agcaagtcct actccagtgc ccccaagtca   1320

tccaaaactg agcttttcaa ggaacctaac gcagagggca ggaggctctc tcttacctca   1380

gggcttattg gtatcctaac accatcttca tcttcatctt ctcagcttgc tccaaatggt   1440

gcaaaatgca ttccagtacg agaccgtggc ttcctggtgc agacaattga gtttgctgaa   1500

cagcggatcc ctgtattaaa tgaatattgt gtggtttgtg atgagccaca tgtgtttcaa   1560

aatggcccta tgcttaggcc taccgtatgt gaacgggagc tgtgtgtgtt tgcttttcaa   1620

accctgggag taatgaatga agctgctgat gaaatagcaa ctggagctca ggtggtagat   1680

ctactagtat ccatgtgtag gtctgcgttg gaatctccta gaaaagttgt gattttcgag   1740

ccatatcctt ctgtggtaga tcctaatgat cctcagatgt tggccttcaa ccccaggaaa   1800

aagaactatg atcgagtaat gaaagcactg gatagcataa cttctatcag agaaatgaca   1860

caagcaccat atctggaaat caagaagcaa atggataaac aggaccccct tgctcatccc   1920

ttactgcaat gggttatatc aagtaataga tcacatattg tgaaactgcc agttaacagg   1980

caattgaagt ttatgcatac tccacatcag ttccttcttc tcagcagtcc accagccaaa   2040

gaatccaatt ttagagctgc taaaaaactc tttggaagca cctttgcatt tcatggctca   2100

cacattgaaa actggcactc catcctgagg aatggtctgg ttgttgcttc taatacacga   2160

ttgcagctcc atggtgcaat gtatggaagt ggaatctatc ttagtccaat gtcaagcata   2220

tcatttggtt actcagggat gaacaagaaa cagaaggtgt cagccaagga cgagccagct   2280

tcaagcagta aaagcagcaa tacatcacag tcacagaaaa aaggacagca atcccaattc   2340

ctgcaaagcc gtaacttaaa atgcatagcc ttatgtgaag tgatcacctc atctgacctg   2400

cacaaacatg gagagatatg ggttgtcccc aatactgacc atgtctgcac acgattcttt   2460

ttcgtctatg aagacggcca agtgggagat gcaaatatta atacacaaga aggaggcatt   2520

cacaaagaga tcctccgagt aattggtaat caaactgcta ctggttaa               2568
```

<210> SEQ ID NO 14
<211> LENGTH: 2568
<212> TYPE: DNA
<213> ORGANISM: Homo sapiens

<400> SEQUENCE: 14

```
aggatggact tttccatggt ggccggagca gcagcttaca atgaaaaatc aggtaggatt     60

acctcgctct cactcttgtt tcagaaagtc tttgctcaga tctttcctca gtggagaaag    120

gggaatacag aagaatgtct cccctacaag tgctcagaga ctggtgctct tggagaaaac    180

tatagttggc aaattcccat taaccacaat gacttcaaaa ttttaaaaaa taatgagcgt    240

cagctgtgtg aagtcctcca gaataagttt ggctgtatct ctaccctggt ctctccagtt    300

caggaaggca acagcaaatc tctgcaagtg ttcagaaaaa tgctgactcc taggatagag    360

ttatcagtct ggaaagatga cctcaccaca catgctgttg atgctgtggt gaatgcagcc    420

aatgaagatc ttctgcatgg gggaggcctg gccctggccc tggtaaaagc tggtggattt    480

gaaatccaag aagagagcaa acagtttgtt gccagatatg gtaaagtgtc agctggtgag    540

atagctgtca cgggagcagg gaggcttccc tgcaaacaga tcatccatgc tgttgggcct    600

cggtggatgg aatgggataa acagggatgt actggaaagc tgcagagggc cattgtaagt    660
```

```
attctgaatt atgtcatcta taaaaatact cacattaaga cagtagcaat tccagccttg    720

agctctggga tttttcagtt ccctctgaat ttgtgtacaa agactattgt agagactatc    780

cgggttagtt tgcaagggaa gccaatgatg agtaatttga aagaaattca cctggtgagc    840

aatgaggacc ctactgttgc tgcctttaaa gctgcttcag aattcatcct agggaagagt    900

gagctgggac aagaaaccac cccttctttc aatgcaatgg tcgtgaacaa cctgaccctc    960

cagattgtcc agggccacat tgaatggcag acggcagatg taattgttaa ttctgtaaac   1020

ccacatgata ttacagttgg acctgtggca aagtcaattc tacaacaagc aggagttgaa   1080

atgaaatcgg aatttcttgc cacaaaggct aaacagtttc aacggtccca gttggtactg   1140

gtcacaaaag gatttaactt gttctgtaaa tatatatacc atgtactgtg gcattcagaa   1200

tttcctaaac ctcagatatt aaaacatgca atgaaggagt gtttggaaaa atgcattgag   1260

caaaatataa cttccatttc ctttcctgcc cttgggactg gaaacatgga aataaagaag   1320

gaaacagcag cagagatttt gtttgatgaa gttttaacat ttgccaaaga ccatgtaaaa   1380

caccagttaa ctgtaaaatt tgtgatcttt ccaacagatt tggagatata taaggctttc   1440

agttctgaaa tggcaaagag gtccaagatg ctgagtttga acaattacag tgtcccccag   1500

tcaaccagag aggagaaaag agaaaatggg cttgaagcta gatctcctgc catcaatctg   1560

atgggattca acgtggaaga gatgtgtgag gcccacgcat ggatccaaag aatcctgagt   1620

ctccagaacc accacatcat tgagaataat catattctgt accttgggag aaaggaacat   1680

gacattttgt ctcagcttca gaaaacttca agtgtctcca tcacagaaat tatcagccca   1740

ggaaggacag agttagagat tgaaggagcc cgggctgacc tcattgaggt ggttatgaac   1800

attgaagata tgctttgtaa agtacaggag gaaatggcaa ggaaaaagga gcgaggcctt   1860

tggcgctcgt taggacagtg gactattcag caacaaaaaa cccaagacga aatgaaagaa   1920

aatatcatat ttctgaaatg tcctgtgcct ccaactcaag agcttctaga tcaaaagaaa   1980

cagtttgaaa aatgtggttt gcaggttcta aaggtggaga agatagacaa tgaggtcctt   2040

atggctgcct ttcaaagaaa gaagaaaatg atggaagaaa aactgcacag gcaacctgtg   2100

agccataggc tgtttcagca agtcccatac cagttctgca atgtggtatg cagagttggc   2160

tttcaaagaa tgtactcgac accttgcgat ccaaaatacg gagctggcat atacttcacc   2220

aagaacctca aaaacctggc agagaaggcc aagaaaatct ctgctgcaga taagctgatc   2280

tatgtgtttg aggctgaagt actcacaggc ttcttctgcc agggacatcc gttaaatatt   2340

gttcccccac cactgagtcc tggagctata gatggtcatg acagtgtggt tgacaatgtc   2400

tccagccctg aaacctttgt tatttttagt ggcatgcagg ctatacctca gtatttgtgg   2460

acatgcaccc aggaatatgt acagtcacaa gattactcat caggaccaat gagacccttt   2520

gcacagcatc cttggagggg attcgcaagt ggcagccctg ttgattaa                2568
```

<210> SEQ ID NO 15
<211> LENGTH: 3081
<212> TYPE: DNA
<213> ORGANISM: Homo sapiens

<400> SEQUENCE: 15

```
ggaatggttg caatggcgga ggcagaggca ggggtggcag tggaggtccg tggactgccc     60

cctgccgtgc ccgacgagct gctcactctc tactttgaaa accgccgacg ctctggaggg    120

ggacctgtgt tgagctggca gagactgggc tgtgggggcg tcctcacctt cagagagcct    180

gcagacgccg agagggtctt ggcccaggca gatcatgaac tacatggtgc ccagctgagc    240
```

```
ctgcggccag ctccaccacg agcccctgca cgcctgctgc tccaaggact gcccccctggc    300
accacgcccc agcgcttgga gcagcatgtc caggccttgc tgcgggcctc ggggctccca    360
gtacagcctt gctgtgcctt ggccagcccc cggccagacc gggctctggt ccagttgccc    420
aagccccttt ctgaggcaga tgtccgtgtc ctggaggagc aggcccagaa tctgggcctg    480
gaggggacct tggtgtccct ggcccgggtt ccccaggccc gagcggtgcg tgtggtgggg    540
gatggtgcct ctgtggacct gctgttgctg gagttgtacc tggagaatga gcgccgcagt    600
ggtggggggc ccctggagga cctgcaacgc ctacccgggc ccctgggcac tgttgcctcc    660
ttccagcagt ggcaagtggc agaacgagtg ttgcagcagg agcaccggtt gcagggctca    720
gagctgagcc ttgtccccca ctacgacgtc ctggagcccg aggagctggc tgagaacacc    780
agtggagggg accacccgtc cacccagggg cctagggcta ccaagcatgc tctcctgagg    840
accggagggt tggtgacggc tctgcagggt gcagggactg tgacaatggg ctctggcgag    900
gaaccagggc agtcaggggc ctctctgagg acaggtccca tagtgcaggg tagagggatt    960
atgacaacag gctctggcca ggaaccaggg cagtcaggga cctctctgag gacaggtccc   1020
atggggtctc tgggacaggc agagcaagtc agctcgatgc ccatggggtc tctggaacat   1080
gaggggctgg taagcctgag gcctgtgggg ttgcaggaac aggaggggcc catgagcctg   1140
gggcctgtgg ggtctgcagg cccagtggag acctctaagg ggttgccggg gcaggagggc   1200
ctggtggaaa ttgccatgga ctcaccagag caagaggggc tggtgggtcc catggagatc   1260
accatggggt ctctggagaa ggcagggcct gtgagcccag gatgtgtgaa gctggcaggg   1320
caggagggcc tggtggagat ggtgctattg atggagccag gggcgatgcg cttcctgcag   1380
ctctaccatg aggaccttct tgcgggcctg ggagacgtcg ctctcttgcc acttgaagga   1440
ccggatatga ctggctttcg gctctgtgga gcccaggctt cctgccaggc ggctgaggag   1500
tttctgcgga gcctgctggg cagcattagc tgccatgtgt tgtgcctgga gcactcgggc   1560
agcgccaggt ttctcctggg cccagaaggg cagcaccttc tccaggggct ggaggctcag   1620
ttccagtgtg tctttgggac agagcgcctg gccacagcca cgttggacac aggccttgaa   1680
gaggtggacc ctaccgaggc cctcccagtg ctccctggca acgcccacac cctgtggacc   1740
ccagacagta caggtggtga ccaggaggac gtgagcctgg aggaggtccg agaactgctg   1800
gccaccctgg agggcctaga cctagacggg gaggactggc tgcctcggga gctggaggag   1860
gaagggcctc aggagcagcc agaggaggag gcgaccccag ggcatgagga ggaggagcct   1920
gtggccccca gcactgtggc acccaggtgg ctggaggagg aggccgctct gcagctggcc   1980
ctccaccggt cactggagcc tcaaggtcag gtggctgagc aggaggaggc tgctgccctg   2040
cggcaagccc taaccctctc cctgctggag cagcccccgt tggaggcaga agagcccccca   2100
gatgggggga ctgatggcaa ggcccagctg gtggtgcact cggcctttga gcaggatgtg   2160
gaggagctgg accgggcgct cagggctgcc ttggaggtcc acgtccagga ggagacggtg   2220
gggccctggc gccgcacact gcctgcagag ctgcgtgctc gcctggagcg gtgccatggt   2280
gtgagtgttg ccctgcgtgg tgactgcacc atcctccgtg gcttcggggc ccaccctgcc   2340
cgtgctgccc gccacttggt ggcacttctg gctggcccct gggatcagag tttggccttt   2400
cccttggcag cttcaggccc taccttggcg gggcagacgc tgaaggggcc ctggaacaac   2460
ctggagcgtc tggcagagaa caccggggag ttccaggagg tggtgcgggc cttctacgac   2520
accctggacg ctgcccgcag cagcatccgc gtcgttcgtg tggagcgcgt gtcgcacccg   2580
ctgctgcagc agcagtatga gctgtaccgg gagcgcctgc tgcagcgatg cgagcggcgc   2640
```

```
ccggtggagc aggtgctgta ccacggcacg acggcaccgg cagtgcctga catctgcgcc   2700
cacggcttca accgcagctt ctgcggccgc aacgccacgg tctacgggaa gggcgtgtat   2760
ttcgccaagc gcgcctccct gtcggtgcag gaccgctact cgcccccca cgccgatggc   2820
cataaggcgg tgttcgtggc acgggtgctg actggcgact acgggcaggg ccgccgcggt   2880
ctgcgggcgc cccctctgcg gggtcctggc cacgtgctcc tgcgctacga cagcgccgtg   2940
gactgcatct gccagcccag catcttcgtc atcttccacg acacccaggc gctgcccacc   3000
cacctcatca cctgcgagca cgtgccccgc gcttcccccg acgacccctc tgggctcccg   3060
ggccgctccc cagacactta a                                             3081
```

<210> SEQ ID NO 16
<211> LENGTH: 3081
<212> TYPE: DNA
<213> ORGANISM: Homo Sapiens

<400> SEQUENCE: 16

```
ggaatggttg caatggcgga ggcagaggca ggggtggcag tggaggtccg tggactgccc     60
cctgccgtgc ccgacgagct gctcactctc tactttgaaa accgccgacg ctctggaggg    120
ggacctgtgt tgagctggca gagactgggc tgtgggggcg tcctcacctt cagagagcct    180
gcagacgccg agagggtctt ggcccaggca gatcatgaac tacatggtgc ccagctgagc    240
ctgcggccag ctccaccacg agcccctgca cgcctgctgc tccaaggact gcccccctggc   300
accacgcccc agcgcttgga gcagcatgtc caggccttgc tgcgggcctc ggggctccca    360
gtacagcctt gctgtgcctt ggccagcccc cggccagacc gggctctggt ccagttgccc    420
aagccccttt ctgaggcaga tgtccgtgtc ctggaggagc aggcccagaa tctgggcctg    480
gaggggacct tggtgtccct ggcccgggtt ccccaggccc gagcggtgcg tgtggtgggg    540
gatggtgcct ctgtggacct gctgttgctg gagttgtacc tggagaatga gcgccgcagt    600
ggtgggggc cctggagga cctgcaacgc ctacccgggc ccctgggcac tgttgcctcc    660
ttccagcagt ggcaagtggc agaacgagtg ttgcagcagg agcaccggtt gcagggctca    720
gagctgagcc ttgtccccca ctacgacgtc ctggagcccg aggagctggc tgagaacacc    780
agtggagggg accacccgtc cacccagggg cctagggcta ccaagcatgc tctcctgagg    840
accggagggt tggtgacggc tctgcagggt gcagggactg tgacaatggg ctctggcgag    900
gaaccagggc agtcaggggc ctctctgagg acaggtccca tagtgcaggg tagagggatt    960
atgacaacag gctctggcca ggaaccaggg cagtcaggga cctctctgag gacaggtccc   1020
atggggtctc tgggacaggc agagcaagtc agctcgatgc ccatggggtc tctggaacat   1080
gaggggctgg taagcctgag gcctgtgggg ttgcaggaac aggaggggcc catgagcctg   1140
gggcctgtgg ggtctgcagg cccagtggag acctctaagg ggttgccggg gcaggagggc   1200
ctggtggaaa ttgccatgga ctcaccagag caagaggggc tggtgggtcc catggagatc   1260
accatggggt ctctggagaa ggcagggcct gtgagcccag gatgtgtgaa gctggcaggg   1320
caggagggcc tggtggagat ggtgctattg atggagccag ggcgatgcg cttcctgcag    1380
ctctaccatg aggaccttct tgcgggcctg ggagacgtcg ctctcttgcc acttgaagga   1440
ccggatatga ctggctttcg gctctgtgga gcccaggctt cctgccaggc ggctgaggag   1500
tttctgcgga gcctgctggg cagcattagc tgccatgtgt tgtgcctgga gcactcgggc   1560
agcgccaggt ttctcctggg cccagaaggg cagcaccttc tccaggggct ggaggctcag   1620
ttccagtgtg tctttgggac agagcgcctg gccacagcca cgttggacac aggccttgaa   1680
```

```
gaggtggacc ctaccgaggc cctcccagtg ctccctggca acgcccacac cctgtggacc   1740
ccagacagta caggtggtga ccaggaggac gtgagcctgg aggaggtccg agaactgctg   1800
gccaccctgg agggcctaga cctagacggg gaggactggc tgcctcggga gctggaggag   1860
gaagggcctc aggagcagcc agaggaggag gcgaccccag ggcatgagga ggaggagcct   1920
gtggccccca gcactgtggc acccaggtgg ctggaggagg aggccgctct gcagctggcc   1980
ctccaccggt cactggagcc tcaaggtcag gtggctgagc aggaggaggc tgctgccctg   2040
cggcaagccc taaccctctc cctgctggag cagcccccgt tggaggcaga agagccccca   2100
gatgggggga ctgatggcaa ggcccagctg gtggtgcact cggcctttga gcaggatgtg   2160
gaggagctgg accgggcgct cagggctgcc ttggaggtcc acgtccagga ggagacggtg   2220
gggccctggc gccgcacact gcctgcagag ctgcgtgctc gcctggagcg gtgccatggt   2280
gtgagtgttg ccctgcgtgg tgactgcacc atcctccgtg gcttcggggc ccaccctgcc   2340
cgtgctgccc gccacttggt ggcacttctg gctggcccct gggatcagag tttggccttt   2400
cccttggcag cttcaggccc taccttggcg gggcagacgc tgaaggggcc ctggaacaac   2460
ctggagcgtc tggcagagaa caccggggag ttccaggagg tggtgcgggc cttctacgac   2520
accctggacg ctgcccgcag cagcatccgc gtcgttcgtg tggagcgcgt gtcgcacccg   2580
ctgctgcagc agcagtatga gctgtaccgg gagcgcctgc tgcagcgatg cgagcggcgc   2640
ccggtggagc aggtgctgta ccacggcacg acggcaccgg cagtgcctga catctgcgcc   2700
cacggcttca accgcagctt ctgcggccgc aacgccacgg tctacgggaa gggcgtgtat   2760
ttcgccaagc gcgcctccct gtcggtgcag gaccgctact cgccccccaa cgccgatggc   2820
cataaggcgg tgttcgtggc acgggtgctg actggcgact acgggcaggg ccgccgcggt   2880
ctgcgggcgc cccctctgcg ggtcctggc cacgtgctcc tgcgctacga cagcgccgtg   2940
gactgcatct gccagcccag catcttcgtc atcttccacg acacccaggc gctgcccacc   3000
cacctcatca cctgcgagca cgtgccccgc gcttcccccg acgacccctc tgggctcccg   3060
ggccgctccc cagacactta a                                            3081
```

<210> SEQ ID NO 17
<211> LENGTH: 999
<212> TYPE: DNA
<213> ORGANISM: Homo sapiens

<400> SEQUENCE: 17

```
gagatgtttc acaaagcaga agaattattt tctaaaacaa caaacaatga agtggatgac     60
atggacacgt cagataccca gtggggctgg ttttacttgg cagaatgtgg gaagtggcac    120
atgtttcagc cggataccaa cagtcagtgt tcagttagca gtgaagatat cgaaaaaagc    180
ttcaaaacaa acccttgtgg ctccatttct tttactactt ccaaattcag ctacaagata    240
gactttgcag aaatgaagca aatgaatctc accactggaa agcagcgctt aataaaaaga    300
gcccccttttt ctatcagtgc tttcagttac atctgtgaaa acgaggccat ccctatgcca    360
ccacactggg agaatgtgaa tactcaagta ccatatcagc ttattcctct gcacaatcaa    420
acacatgaat ataatgaagt tgctaatctc tttgggaaga cgatggatcg caaccgaatt    480
aaaagaattc agagaattca aaacctagat ttgtgggagt tcttttgcag gaaaaaggct    540
cagctcaaga aaaaaagagg tgtgcctcag attaatgaac aaatgctgtt tcatggtacc    600
agcagtgaat ttgtggaagc aatctgcatt cataactttg attggagaat aaatggtata    660
catggtgctg tctttggaaa aggaacctat tttgctagag atgctgctta ttccagtcgt    720
```

```
ttctgcaaag atgacataaa gcatgggaac acattccaaa ttcatggtgt cagcttgcaa     780

cagcggcatc tgtttagaac atataaatct atgtttcttg ctcgagtgct aattggagat     840

tacataaacg gagactccaa atacatgcga cctccttcca aagacgggag ctatgtgaat     900

ttatatgaca gctgtgtgga tgatacctgg aacccaaaga tctttgtggt ttttgatgcc     960

aaccaaatct atcctgagta cttgatagac tttcattga                           999


<210> SEQ ID NO 18
<211> LENGTH: 2109
<212> TYPE: DNA
<213> ORGANISM: Homo sapiens

<400> SEQUENCE: 18

gccatggccc aggccggcgt cgtcggtgag gtcacccagg tgctgtgcgc ggccgggggc      60

gccctggagt tgcccgagct gcggcgccgc ttgcggatgg gcttgagcgc cgacgcgctg     120

gagcggctgc tgcggcagcg tgggcgcttc gtggtggcgg tgcgggcggg cggcgcagcc     180

gcggccccgg agcgcgtggt gctggccgcc tcgccgctgc gcctgtgtcg cgcgcaccag     240

ggctccaagc cgggctgcgt ggggctctgc gcgcagctcc acctctgcag gttcatggtc     300

tacggcgcct gcaagttcct gagagccggg aagaactgta ggaatagtca cagcttgaca     360

accgaacaca acctgagtgt gctgagaact catggcgttg accacctgag ctataatgag     420

ctatgccaac tcttgtttca gaacgacccc tggcttttgc cagaaatttg ccaacattac     480

aacaaaggag atggacccca cggctcttgt gcctttcaaa agcagtgcat caagctccat     540

atctgccagt attttttaca gggggaatgc aagtttggca ctagctgtaa gagatcccat     600

gatttctcta attctgagaa tctggaaaaa ttggagaagt tgggtatgag ctcagacctg     660

gtgagcaggc tgcctaccat ttatagaaat gcacatgaca tcaagaataa gagctctgcc     720

cccagcagag tgcctcctct tttgtcccca caggggactt ctgaaagaaa agacagttca     780

ggttctgtgt ccccaaacac tcttagccag gaggagggtg atcagatctg tttgtaccat     840

atccggaaaa gttgtagctt tcaagataag tgccatagag ttcatttcca tttgccgtat     900

cgatggcaat tcttggatag aggcaaatgg gaggatttgg acaacatgga acttattgaa     960

gaggcatatt gcaatcccaa aatagaaagg atcctgtgct ctgagtcagc cagtaccttt    1020

cactctcatt gtctgaactt taacgccatg acttacggtg ctacccaggc tcgccgcctc    1080

tccacggcct cctctgtcac caaacctcca cacttcatcc tcaccactga ctggatttgg    1140

tactggagtg atgagtttgg ttcttggcag gaatatggaa gacagggcac ggtgcaccct    1200

gtgaccactg tcagcagtag cgacgtggag aaggcctacc tggcctactg tacaccgggg    1260

tctgacggcc aggcagccac cttgaagttc caggccggaa agcacaacta cgagttagat    1320

ttcaaagcct tcgttcagaa aaacctggtc tatggcacaa ctaaaaaggt ttgccgcaga    1380

cccaaatacg tgtctcccca ggatgtgacg accatgcaaa cctgcaatac caagtttcca    1440

ggcccgaaga gcatcccaga ctattgggac tcctctgccc tgccagaccc aggctttcag    1500

aagatcaccc ttagttcttc ctcggaagag tatcagaagg tctggaacct ctttaaccgc    1560

acgctgcctt tctactttgt tcagaagatt gagcgagtac agaacctggc cctctgggaa    1620

gtctaccagt ggcaaaaagg acagatgcag aagcagaatg gagggaaggc cgtggacgag    1680

cggcagctgt tccacggcac cagcgccatt tttgtggacg ccatctgcca gcagaacttt    1740

gactggcggg tctgtggtgt tcatggcact tcctacggca aggggagcta ctttgcccga    1800

gatgctgcat attcccacca ctacagcaaa tccgacacgc agacccacac gatgttcctg    1860
```

```
gcccgggtgc tggtgggcga gttcgtcagg ggcaatgcgt cctttgtccg tccgccggcc   1920

aaggagggct ggagcaacgc cttctatgat agctgcgtga acagtgtgtc cgacccctcc   1980

atctttgtga tctttgagaa acaccaggtc tacccagagt atgtcatcca gtacaccacc   2040

tcctccaagc cctcggtcac accctccatc ctgctggcct tgggctccct gttcagcagc   2100

cgacagtga                                                           2109
```

<210> SEQ ID NO 19
<211> LENGTH: 2712
<212> TYPE: DNA
<213> ORGANISM: Homo sapiens

<400> SEQUENCE: 19

```
gccatggcgg acccggaggt gtgctgcttc atcaccaaaa tcctgtgcgc ccacgggggc     60

cgcatggccc tggacgcgct gctccaggag atcgcgctgt ctgagccgca gctctgtgag    120

gtgctgcagg tggccgggcc cgaccgcttt gtggtgttgg agaccggcgg cgaggccggg    180

atcacccgat cggtggtggc caccactcga gcccgggtct gccgtcgcaa gtactgccag    240

agaccctgcg ataacctgca tctctgcaaa ctcaacttgc tgggccggtg caactattcg    300

cagtccgagc ggaatttatg caaatattct catgaggttc tctcagaaga gaacttcaaa    360

gtcctgaaaa atcacgaact ctctggactg aacaaagagg aattagcagt gctcctcctc    420

caaagtgatc ctttttttat gcccgagata tgcaaaagtt ataagggaga gggtcggcag    480

cagatttgta accagcagcc accgtgttca agactccaca tctgtgacca cttcacccga    540

gggaactgtc gttttcccaa ctgcctccgg tcccataacc tgatggacag aaaggtgctg    600

gccatcatga gggagcacgg gctgaacccc gacgtggtcc agaacatcca ggacatctgc    660

aacagcaagc acatgcagaa gaatcccccca gggcccagag ctccttcttc acatcgtaga    720

aacatggcat atagggctag aagcaagagt agagatcggt tctttcaggg cagccaagaa    780

tttcttgcgt ctgcttcagc gtctgctgag aggtcctgca cacctagtcc agatcagatc    840

agccacaggg cttccctgga ggacgcgcct gtggacgatc tcacccgcaa gttcacgtat    900

ctggggagtc aggatcgcgc tcggcctccc tcaggctcgt ccaaggctac tgatcttgga    960

ggaacaagtc aggccgggac aagccagagg tttttagaga acggcagtca agaggacctc   1020

ttgcatggaa atccaggcag cacttacctt gcttccaatt caacatcagc ccccaactgg   1080

aagagcctca catcctggac gaatgaccaa ggcgccagga gaaagactgt gttttctccc   1140

acgctacctg ccgcccgctc ttctcttggc tctctgcaaa cacctgaagc tgtgaccacc   1200

agaaagggca caggcttgct ttcctcagac tacaggatca tcaatggcaa aagtggaact   1260

caggacatcc agcctggccc tctttttaat aataatgctg atggagtggc cacagatata   1320

acttctacca gatccttaaa ttacaaaagc actagcagcg gtcacagaga aatatcatca   1380

cctaggattc aggatgctgg acctgcttcc cgagatgtcc aggccactgg cagaatcgca   1440

gatgatgctg acccaagagt agcacttgtt aacgattctt tatctgatgt cacaagtacc   1500

acatcttcta gggtggatga tcatgactca gaggaaattt gtcttgacca tctgtgtaag   1560

ggttgtccgc ttaatggtag ctgcagcaaa gtccacttcc atctgcctta ccggtggcag   1620

atgcttattg gtaaaacctg gacggacttt gagcacatgg agacgatcga gaaaggctac   1680

tgtaaccccg gaatccacct ctgttctgta ggaagttata caatcaattt tcgggtaatg   1740

agttgtgatt cctttcccat ccgacgcctc tccactcctt cttctgtcac caagccagcc   1800

aattctgtct tcaccaccaa atggatttgg tattggaaga atgaatctgg cacatggatt   1860
```

cagtatggag aagagaaaga caaacggaaa aattcaaacg tcgactcttc atacctggag 1920
tctctctatc aatcctgtcc gaggggagtt gtgccatttc aggcgggctc acggaactat 1980
gagctgagtt tccaagggat gattcagaca aacatagctt ccaaaactca aaaggatgtc 2040
atcagaagac caacatttgt gcctcagtgg tatgtgcagc agatgaagag agggccagac 2100
catcagccag caaagacctc gtcagtgtct ttaactgcga cctttcgtcc tcaggaggac 2160
ttttgcttcc tatcctcaaa gaaatataag ttgtcagaga tccatcacct acatccagaa 2220
tatgtcagag taagtgagca ttttaaagct tccatgaaaa atttcaagat tgaaaagata 2280
aagaagatcg agaactcaga gctcctggat aaatttacat ggaagaaatc gcagatgaag 2340
gaagaaggaa aactcctatt ttatgcgaca agccgtgcct atgtggaatc tatctgttcg 2400
aataattttg acagtttcct acatgaaact catgaaaaca aatacggaaa aggaatttac 2460
tttgcaaaag atgccatcta ttcccacaaa aattgcccgt atgatgccaa aaacgtcgtt 2520
atgtttgtag cccaagttct ggttggaaag tttactgaag gaaatataac gtacacgagc 2580
cctcctccac agttcgacag ctgtgtggat accagatcga atccctccgt ttttgtcatc 2640
tttcagaaag atcaggttta cccacaatat gtgattgaat atactgaaga caaagcctgc 2700
gtgattagtt ag 2712

<210> SEQ ID NO 20
<211> LENGTH: 2103
<212> TYPE: DNA
<213> ORGANISM: Homo sapiens

<400> SEQUENCE: 20
gccatggcgg acccggaggt gtgctgcttc atcaccaaaa tcctgtgcgc ccacgggggc 60
cgcatggccc tggacgcgct gctccaggag atcgcgctgt ctgagccgca gctctgtgag 120
gtgctgcagg tggccgggcc cgaccgcttt gtggtgttgg agaccggcgg cgaggccggg 180
atcacccgat cggtggtggc caccactcga gcccgggtct gccgtcgcaa gtactgccag 240
agaccctgcg ataacctgca tctctgcaaa ctcaacttgc tgggccggtg caactattcg 300
cagtccgagc ggaatttatg caaatattct catgaggttc tctcagaaga gaacttcaaa 360
gtcctgaaaa atcacgaact ctctggactg aacaaagagg aattagcagt gctcctcctc 420
caaagtgatc ctttttttat gcccgagata tgcaaaagtt ataagggaga gggtcggcag 480
cagatttgta accagcagcc accgtgttca agactccaca tctgtgacca cttcacccga 540
gggaactgtc gttttcccaa ctgcctccgg tcccataacc tgatggacag aaaggtgctg 600
gccatcatga gggagcacgg gctgaacccc gacgtggtcc agaacatcca ggacatctgc 660
aacagcaagc acatgcagaa gaatcccccca gggcccagag ctccttcttc acatcgtaga 720
aacatggcat atagggctag aagcaagagt agagatcggt tctttcaggg cagccaagaa 780
tttcttgcgt ctgcttcagc gtctgctgag aggtcctgca cacctagtcc agatcagatc 840
agccacaggg cttccctgga ggacgcgcct gtggacgatc tcacccgcaa gttcacgtat 900
ctggggagtc aggatcgcgc tcggcctccc tcaggctcgt ccaaggctac tgatcttgga 960
ggaacaagtc aggccgggac aagccagagg tttttagaga acggcagtca agaggacctc 1020
ttgcatggaa atccaggcag cacttacctt gcttccaatt caacatcagc ccccaactgg 1080
aagagcctca catcctggac gaatgaccaa ggcgccagga gaaagactgt gttttctccc 1140
acgctacctg ccgcccgctc ttctcttggc tctctgcaaa cacctgaagc tgtgaccacc 1200
agaaagggca caggcttgct ttcctcagac tacaggatca tcaatggcaa aagtggaact 1260

```
caggacatcc agcctggccc tctttttaat aataatgctg atggagtggc cacagatata   1320

acttctacca gatccttaaa ttacaaaagc actagcagcg gtcacagaga aatatcatca   1380

cctaggattc aggatgctgg acctgcttcc cgagatgtcc aggccactgg cagaatcgca   1440

gatgatgctg acccaagagt agcacttgtt aacgattctt tatctgatgt cacaagtacc   1500

acatcttcta gggtggatga tcatgactca gaggaaattt gtcttgacca tctgtgtaag   1560

ggttgtccgc ttaatggtag ctgcagcaaa gtccacttcc atctgcctta ccggtggcag   1620

atgcttattg gtaaaacctg gacggacttt gagcacatgg agacgatcga gaaaggctac   1680

tgtaaccccg gaatccacct ctgttctgta ggaagttata caatcaattt tcgggtaatg   1740

agttgtgatt cctttcccat ccgacgcctc tccactcctt cttctgtcac caagccagcc   1800

aattctgtct tcaccaccaa atggatttgg tattggaaga atgaatctgg cacatggatt   1860

cagtatggag aagagaaaga caaacggaaa aattcaaacg tcgactcttc atacctggag   1920

tctctctatc aatcctgtcc gaggggagtt gtgccatttc aggcgggctc acggaactat   1980

gagctgagtt tccaagggat gattcagaca aacatagctt ccaaaactca aaaggatgtc   2040

atcagaagac caacatttgt gcctcagtgg tatgtgcagc agatgaagag agggccagag   2100

taa                                                                 2103
```

<210> SEQ ID NO 21
<211> LENGTH: 4560
<212> TYPE: DNA
<213> ORGANISM: Homo sapiens

<400> SEQUENCE: 21

```
atcatggcca caaaactcga cttcaataaa atgccacttt ctgtgttccc atactatgcc     60

tcattgggca cagccttgta tggaaaggag aagcctctga tcaagcttcc agcaccattt    120

gaagagtcac tagatcttcc cttatggaag ttcttacaga aaaagaatca cctcattgag    180

gagataaacg atgaaatgag gcgttgtcac tgtgagctca cgtggtccca actcagtggt    240

aaagttacca tcagaccagc agccacctta gtcaatgaag gaagaccgag aatcaagacc    300

tggcaggcag atacttccac aacactctct agcatcaggt ctaaatataa agtcaaccca    360

attaaagtgg atccaacaat gtgggacacc ataaaaaatg atgtgaaaga tgacaggatt    420

ttgattgagt ttgatacact taaggagatg gtaatcttag cagggaaatc agaggatgtc    480

caaagcattg aggtacaagt caggggagtta atagaaagca ctactcaaaa aattaaaagg    540

gaagagcaaa gtttgaagga aaaaatgatc atttctccag gcaggtattt tcttttgtgt    600

cacagcagtc tactggacca tttactcacg gagtgcccag agatagagat ttgttacgat    660

agagtcactc aacacttgtg cttgaaagga cctagtgcag atgtgtataa agcaaagtgt    720

gaaatccagg aaaaggtgta caccatggct cagaaaaaca ttcaggtttc tcctgagatt    780

tttcagtttt tgcaacaggt aaactggaaa gaattctcta agtgtctttt catagcacag    840

aagattcttg cactttatga gctagagggt acaactgttc tcttaaccag ctgttcttct    900

gaagccctgt tagaagcaga aaagcaaatg ctcagtgcct taaattataa gcgcattgaa    960

gttgagaaca aagaagttct tcatggcaag aaatggaaag ggctcactca caatttgctt   1020

aagaaacaaa attcctcccc aaacactgta atcatcaatg agttaacttc agaaaccaca   1080

gctgaagtca tcattacagg ctgtgtaaaa gaagtaaatg aaacctataa attgcttttt   1140

aacttcgttg aacaaaacat gaaaatagag agactggttg aagtaaagcc ttccttagtt   1200

attgactatt taaagacaga aaagaagcta ttctggccaa agataaagaa ggtaaatgtg   1260
```

```
caggtaagtt tcaatcctga gaacaaacaa aaaggcattt tactaactgg ctcaaagacc   1320
gaagtactga aggcagtgga cattgtcaag caagtctggg attcagtctg tgttaaaagt   1380
gtccatactg ataagccagg agccaagcag ttcttccagg ataaagcacg gttttatcaa   1440
agtgagatca aacggttgtt tggttgttac attgaactac aggagaatga agtaatgaag   1500
gagggaggca gccccgctgg gcagaagtgc ttctctcgga cagtcttggc ccctggcgtt   1560
gtgctgattg tgcagcaggg tgacttggca cggcttcctg tcgatgtggt ggtgaatgca   1620
tctaatgagg accttaagca ttatggtggc ctggccgctg cgctctcaaa agcagctggc   1680
cctgagctcc aggccgactg tgaccagata gtgaagagag agggcagact cctaccgggc   1740
aatgccacca tctccaaggc aggaaagctg ccctaccacc acgtgatcca tgcagtgggg   1800
ccccgctgga gcggatatga ggccccgagg tgtgtgtacc tattaaggag agctgtgcaa   1860
ctcagtctct gtctagccga aaaatacaag taccgatcca tagccatccc agctattagt   1920
tctggagtct ttggctttcc cttaggccga tgcgtggaga ccattgtttc tgccatcaag   1980
gaaaacttcc aattcaagaa ggatggacac tgcttgaaag aaatctacct tgtggatgta   2040
tctgagaaga ctgttgaggc ctttgcagaa gctgtgaaaa ctgtatttaa agccaccctg   2100
ccagatacag ctgccccgcc aggtttacca ccagcagcag cggggcctgg gaaaacatca   2160
tgggaaaaag gaagcctggt gtccccggga ggcctgcaga tgctgttggt gaaagagggt   2220
gtgcagaatg ctaagaccga tgttgttgtc aactccgttc ccttggatct cgtgcttagt   2280
agagggcctc tttctaagtc cctcttggaa aaagctggac cagagctcca ggaggaattg   2340
gacacagttg gacaaggggt ggctgtcagc atgggcacag tgctcaaaac cagcagctgg   2400
aatctggact gtcgctatgt gcttcacgtg gtagctccgg agtggagaaa tggtagcaca   2460
tcttcactca agataatgga agacataatc agagaatgta tggagatcac tgagagcttg   2520
tccttaaaat caattgcatt tccagcaata ggaacaggaa acttgggatt tcctaaaaac   2580
atattcgctg aattaatcat ttcagaggtg ttcaaattta gtagcaagaa tcagctgaaa   2640
actttacaag aggttcactt tctgctgcac ccgagtgatc atgaaaatat tcaggcattt   2700
tcagatgaat ttgccagaag ggctaatgga aatctcgtca gtgacaaaat tccgaaggct   2760
aaagatacac aaggtttttta tgggactgtt tctagccctg attcaggtgt gtatgaaatg   2820
aagattggct ccatcatctt ccaggtggct tctggagata tcacgaaaga agaggcagat   2880
gtgattgtaa attcaacatc aaactcattc aatctcaaag caggggtctc caaagcaatt   2940
ttagaatgtg ctggacaaaa tgtagaaagg gaatgttctc agcaagctca gcagcgcaaa   3000
aatgattata taatcaccgg aggtggattt ttgaggtgca agaatatcat tcatgtaatt   3060
ggtggaaatg atgtcaagag ttcagtttcc tctgttttgc aggagtgtga aaaaaaaaat   3120
tactcatcca tttgcctccc agccattggg acaggaaatg ccaaacaaca cccagataag   3180
gttgctgaag ccataattga tgccattgaa gactttgtcc agaaaggatc agcccagtct   3240
gtgaaaaaag ttaaagttgt tatctttctg cctcaagtac tggatgtgtt ttatgccaac   3300
atgaagaaaa gagaagggac tcagctttct tcccaacagt ctgtgatgtc taaacttgca   3360
tcatttttgg gcttttcaaa gcaatctccc caaaaaaaga atcatttggt tttggaaaag   3420
aaaacagaat cagcaacttt tcgggtgtgt ggtgaaaatg tcacgtgtgt ggaatatgct   3480
atctcctggc tacaagacct gattgaaaaa gaacagtgtc cttacaccag tgaagatgag   3540
tgcatcaaag actttgatga aaaggagtat caggagttga atgagctgca gaagaagtta   3600
aatattaaca tttccctgga ccataagaga cctttgatta aggttttggc aattagcaga   3660
```

```
gatgtgatgc aggctagaga tgaaattgag gcgatgatca agagagttcg attgggcaaa   3720

gaacaggaat cccgggcaga ttgtatcagt gagtttatag aatggcagta taatgacaat   3780

aacacttctc attgttttaa caaaatgacc aatctgaaat tagaggatgc aaggagagaa   3840

aagaaaaaaa cagttgatgt caaaattaat catcggcact acacagtgaa cttgaacaca   3900

tacactgcca cagacacaaa gggccacagt ttatctgttc agcgcctcac gaaatccaaa   3960

gttgacatcc ctgcacactg gagtgatatg aagcagcaga atttctgtgt ggtggagctg   4020

ctgcctagtg atcctgagta caacacggtg gcaagcaagt ttaatcagac ctgctcacac   4080

ttcagaatag agaagattga gaggatccag aatccagatc tctggaatag ctaccaggca   4140

aagaaaaaaa ctatggatgc caagaatggc cagacaatga atgagaagca actcttccat   4200

gggacagatg ccggctccgt gccacacgtc aatcgaaatg gctttaaccg cagctatgcc   4260

ggaaagaatg ctgtggcata tggaaaggga acctattttg ctgtcaatgc caattattct   4320

gccaatgata cgtactccag accagatgca aatgggagaa agcatgtgta ttatgtgcga   4380

gtacttactg gaatctatac acatggaaat cattcattaa ttgtgcctcc ttcaaagaac   4440

cctcaaaatc ctactgacct gtatgacact gtcacagata atgtgcacca tccaagttta   4500

tttgtggcat tttatgacta ccaagcatac ccagagtacc ttattacgtt tagaaaataa   4560
```

```
<210> SEQ ID NO 22
<211> LENGTH: 2040
<212> TYPE: DNA
<213> ORGANISM: Homo sapiens

<400> SEQUENCE: 22
```

```
aggatggctg cgccaggccc ccttcctgcc gctgctctga gtccaggggc tccgaccccc     60

agagaactta tgcacggagt tgcaggtgtt acttccagag ccggacgaga tcgggaggcg    120

gggagcgtgc tgccggccgg gaaccgtggg gcgcggaagg cctcccggcg ctcttcctcc    180

cggagtatgt ccagagacaa caagttcagc aagaaagatt gtctttcaat caggaatgtt    240

gtagcttcaa tccaaaccaa agaaggtctg aatctcaagt tgataagtgg agatgttctg    300

tacatctggg ccgatgtcat tgtcaacagc gttcccatga atcttcagct tggaggagga    360

ccactatctc gggcattttt gcagaaagct ggtcccatgc tccagaaaga gttagatgac    420

agaaggcggg aaacagagga aaaagtaggt aacatattca tgacaagcgg ctgcaatctg    480

gactgcaaag ctgtgctcca tgctgtggct ccatactgga ataatggagc agagacttct    540

tggcagatca tggcaaatat aatcaagaaa tgtttgacaa ctgtagaagt gctatctttc    600

tcatcaatca catttcccat gattggaaca ggaagtttgc agtttcccaa agctgttttt    660

gctaaactaa tcctttcaga agtgttcgaa tacagtagca gcacaaggcc gataactagc    720

cctttacaag aagtccactt tctggtatat acaaatgacg atgaaggctg tcaggcattt    780

ttagatgaat tcactaactg gtcaagaata aatcccaaca aggccaggat tcccatggca    840

ggagataccc aaggtgtggt cgggactgtc tctaagcctt gtttcacagc atatgaaatg    900

aaaatcggtg caattacttt tcaggttgct actggagata tagccactga acaggtagat    960

gttattgtaa actcaacagc aaggacattt aatcggaaat caggtgtgtc aagagctatt   1020

ttagaaggtg ctggacaagc tgtggaaagt gaatgtgctg tactagctgc acagcctcac   1080

agagatttta taattacacc aggtggatgc ttaaagtgca aaataataat tcatgttcct   1140

gggggaaaag atgtcaggaa aacggtcacc agtgttctag aagagtgtga acagaggaag   1200

tacacatcgg tttcccttcc agccattgga acaggaaatg ccggaaaaaa ccctatcaca   1260
```

```
gttgctgata acataatcga tgctattgta gacttctcat cacaacattc caccccatca   1320

ttaaaaacag ttaaagttgt catttttcaa cctgagctgc taaatatatt ctacgacagc   1380

atgaaaaaaa gagacctctc tgcatcactg aactttcagt ccacattctc catgactaca   1440

tgtaatcttc ctgaacactg gactgacatg aatcatcagc tgttttgcat ggtccagcta   1500

gagccaggac aatcagaata taataccata aaggacaagt tcacccgaac ttgttcttcc   1560

tacgcaatag agaagattga gaggatacag aatgcatttc tctggcagag ctaccaggta   1620

aagaaaaggc aaatggatat caagaatgac cataagaata atgagagact cctcttccat   1680

gggacagatg cagactcagt gccatatgtc aatcagcacg gctttaatag aagttgtgct   1740

gggaaaaatg ctgtatccta tggaaaagga acctattttg ctgtggatgc cagttattct   1800

gccaaggaca cctactccaa gccagacagc aatgggagaa agcacatgta cgttgtgcga   1860

gtacttactg gagtcttcac aaagggacgt gcaggattag tcacccctcc acccaagaat   1920

cctcacaatc ccacagatct ctttgactca gtgacaaaca atacacgatc tccaaagcta   1980

tttgtggtat tctttgataa tcaggcttac ccagaatatc tcataacttt cacggcttaa   2040
```

<210> SEQ ID NO 23
<211> LENGTH: 1338
<212> TYPE: DNA
<213> ORGANISM: Homo sapiens

<400> SEQUENCE: 23

```
tcaatgctcc aaagaattgg attaatattt ttacacaata ttgttgtagt cagtaactgt     60

ttctatttcc aggcattttt agatgaattc actaactggt caagaataaa tcccaacaag    120

gccaggattc ccatggcagg agatacccaa ggtgtggtcg ggactgtctc taagccttgt    180

ttcacagcat atgaaatgaa aatcggtgca attacttttc aggttgctac tggagatata    240

gccactgaac aggtagatgt tattgtaaac tcaacagcaa ggacatttaa tcggaaatca    300

ggtgtgtcaa gagctatttt agaaggtgct ggacaagctg tggaaagtga atgtgctgta    360

ctagctgcac agcctcacag agattttata attacaccag gtggatgctt aaagtgcaaa    420

ataataattc atgttcctgg gggaaaagat gtcaggaaaa cggtcaccag tgttctagaa    480

gagtgtgaac agaggaagta cacatcggtt tcccttccag ccattggaac aggaaatgcc    540

ggaaaaaacc ctatcacagt tgctgataac ataatcgatg ctattgtaga cttctcatca    600

caacattcca ccccatcatt aaaaacagtt aaagttgtca tttttcaacc tgagctgcta    660

aatatattct acgacagcat gaaaaaaaga gacctctctg catcactgaa ctttcagtcc    720

acattctcca tgactacatg taatcttcct gaacactgga ctgacatgaa tcatcagctg    780

ttttgcatgg tccagctaga gccaggacaa tcagaatata ataccataaa ggacaagttc    840

acccgaactt gttcttccta cgcaatagag aagattgaga ggatacagaa tgcatttctc    900

tggcagagct accaggtaaa gaaaaggcaa atggatatca agaatgacca taagaataat    960

gagagactcc tcttccatgg gacagatgca gactcagtgc catatgtcaa tcagcacggc   1020

tttaatagaa gttgtgctgg gaaaaatgct gtatcctatg gaaaaggaac ctattttgct   1080

gtggatgcca gttattctgc caaggacacc tactccaagc cagacagcaa tgggagaaag   1140

cacatgtacg ttgtgcgagt acttactgga gtcttcacaa agggacgtgc aggattagtc   1200

acccctccac ccaagaatcc tcacaatccc acagatctct ttgactcagt gacaaacaat   1260

acacgatctc caaagctatt tgtggtattc tttgataatc aggcttaccc agaatatctc   1320

ataactttca cggcttaa                                                 1338
```

<210> SEQ ID NO 24
<211> LENGTH: 975
<212> TYPE: DNA
<213> ORGANISM: Homo sapiens

<400> SEQUENCE: 24

```
gggatgcagc cctcaggctg ggcggccgcc agggaggcgg cgggccgcga catgctggcc     60

gccgacctcc ggtgcagcct cttcgcctcg gccctgcaga gctacaagcg cgactcggtg    120

ctgcggccct tccccgcgtc ctacgcccgc ggcgactgta aggactttga agccctgctt    180

gcagatgcca gcaagttacc taacctgaaa gaacttctcc agtcctccgg agacaaccac    240

aaacgggcct gggacctggt gagctggatt ttatcctcaa aggtcctgac aatccacagt    300

gcagggaagg cagagtttga aaagatccaa aagctgactg gggctcctca cacgcctgtt    360

cctgcaccgg acttcctgtt tgaaattgag tactttgacc cagccaacgc caaattttat    420

gagaccaaag gagaacgaga cctaatctat gcatttcatg gtagccgcct agaaaacttc    480

cattccatta tccacaatgg cctgcactgc catctgaaca agacatcctt gttcggagag    540

gggacctacc tcaccagtga cttgagcctg gccctcatat acagccccca tggccatggg    600

tggcagcaca gcctcctcgg ccccatcctt agctgtgtgg ccgtgtgtga ggtcattgac    660

catccggacg tcaagtgcca aaccaagaag aaggattcca aggagataga tcgcagacga    720

gcgagaatca aacatagtga agggggagac atccctccca agtacttcgt ggtcaccaat    780

aaccagctgc tgcgagtgaa gtacctcctg gtgtattcac agaagccacc caagagcagg    840

gcttcgagcc agctctcctg gttttccagc cattggttta ccgtcatgat atccctgtat    900

ctgctgctgc tgctcatagt gagtgtcatc aactcctctg ctttccaaca cttttggaat    960

cgtgcgaaaa gataa                                                     975
```

<210> SEQ ID NO 25
<211> LENGTH: 238
<212> TYPE: PRT
<213> ORGANISM: Aequorea coerulescens

<400> SEQUENCE: 25

```
Met Ser Lys Gly Ala Glu Leu Phe Thr Gly Val Val Pro Ile Leu Ile
1               5                   10                  15

Glu Leu Asn Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Ile Gln Glu Arg
                85                  90                  95

Thr Ile Phe Phe Lys Asp Asp Gly Asn Tyr Lys Ser Arg Ala Glu Val
            100                 105                 110

Lys Phe Glu Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
    130                 135                 140

Tyr Asn Ala His Asn Val Tyr Ile Met Thr Asp Lys Ala Lys Asn Gly
145                 150                 155                 160
```

```
Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Thr Leu Ser
        195                 200                 205

Lys Asp Pro Asn Glu Lys Arg Asp His Met Ile Tyr Phe Glu Phe Val
    210                 215                 220

Thr Ala Ala Ala Ile Thr His Gly Met Asp Glu Leu Tyr Lys
225                 230                 235


<210> SEQ ID NO 26
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid

<400> SEQUENCE: 26

Glu Xaa Xaa Tyr Xaa Gln Ser
1               5


<210> SEQ ID NO 27
<211> LENGTH: 126
<212> TYPE: PRT
<213> ORGANISM: Staphylococcus aureus

<400> SEQUENCE: 27

Gly Pro Ser Ala Val Asp Asn Lys Phe Asn Lys Glu Gln Gln Asn Ala
1               5                   10                  15

Phe Tyr Glu Ile Leu His Leu Pro Asn Leu Asn Glu Glu Gln Arg Asn
            20                  25                  30

Ala Phe Ile Gln Ser Leu Lys Asp Asp Pro Ser Gln Ser Ala Asn Leu
        35                  40                  45

Leu Ala Glu Ala Lys Lys Leu Asn Asp Ala Gln Ala Pro Lys Val Asp
    50                  55                  60

Asn Lys Phe Asn Lys Glu Gln Gln Asn Ala Phe Tyr Glu Ile Leu His
65                  70                  75                  80

Leu Pro Asn Leu Asn Glu Glu Gln Arg Asn Ala Phe Ile Gln Ser Leu
                85                  90                  95

Lys Asp Asp Pro Ser Gln Ser Ala Asn Leu Leu Ala Glu Ala Lys Lys
            100                 105                 110

Leu Asn Asp Ala Gln Ala Pro Lys Val Asp Ala Asn His Gln
        115                 120                 125


<210> SEQ ID NO 28
<211> LENGTH: 4731
<212> TYPE: DNA
<213> ORGANISM: Artificial Sequence
<220> FEATURE:
<223> OTHER INFORMATION: Synthetic Construct
```

<400> SEQUENCE: 28

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggtcgcca ccatggtgag caagggcgag gagctgttca ccggggtggt gcccatcctg    660
gtcgagctgg acggcgacgt aaacggccac aagttcagcg tgtccggcga gggcgagggc    720
gatgccacct acggcaagct gaccctgaag ttcatctgca ccaccggcaa gctgcccgtg    780
ccctggccca ccctcgtgac caccctgacc tacggcgtgc agtgcttcag ccgctacccc    840
gaccacatga agcagcacga cttcttcaag tccgccatgc ccgaaggcta cgtccaggag    900
cgcaccatct tcttcaagga cgacggcaac tacaagaccc gcgccgaggt gaagttcgag    960
ggcgacaccc tggtgaaccg catcgagctg aagggcatcg acttcaagga ggacggcaac   1020
atcctggggc acaagctgga gtacaactac aacagccaca acgtctatat catggccgac   1080
aagcagaaga acggcatcaa ggtgaacttc aagatccgcc acaacatcga ggacggcagc   1140
gtgcagctcg ccgaccacta ccagcagaac acccccatcg gcgacggccc cgtgctgctg   1200
cccgacaacc actacctgag cacccagtcc gccctgagca aagaccccaa cgagaagcgc   1260
gatcacatgg tcctgctgga gttcgtgacc gccgccggga tcactctcgg catggacgag   1320
ctgtacaagt ccggactcag atctcgagct caagcttcga attctgcagt cgacggtacc   1380
gcgggcccgg gatccaccgg atctagataa ctgatcataa tcagccatac cacatttgta   1440
gaggttttac ttgctttaaa aaacctccca cacctccccc tgaacctgaa acataaaatg   1500
aatgcaattg ttgttgttaa cttgtttatt gcagcttata atggttacaa ataaagcaat   1560
agcatcacaa atttcacaaa taaagcattt ttttcactgc attctagttg tggtttgtcc   1620
aaactcatca atgtatctta acgcgtaaat tgtaagcgtt aatattttgt taaaattcgc   1680
gttaaatttt tgttaaatca gctcattttt taaccaatag gccgaaatcg gcaaaatccc   1740
ttataaatca aaagaataga ccgagatagg gttgagtgtt gttccagttt ggaacaagag   1800
tccactatta aagaacgtgg actccaacgt caaagggcga aaaaccgtct atcagggcga   1860
tggcccacta cgtgaaccat caccctaatc aagttttttg gggtcgaggt gccgtaaagc   1920
actaaatcgg aaccctaaag ggagcccccg atttagagct tgacggggaa agccggcgaa   1980
cgtggcgaga aaggaaggga agaaagcgaa aggagcgggc gctagggcgc tggcaagtgt   2040
agcggtcacg ctgcgcgtaa ccaccacacc cgccgcgctt aatgcgccgc tacagggcgc   2100
gtcaggtggc acttttcggg gaaatgtgcg cggaacccct atttgtttat ttttctaaat   2160
acattcaaat atgtatccgc tcatgagaca ataaccctga taaatgcttc aataatattg   2220
aaaaaggaag agtcctgagg cggaaagaac cagctgtgga atgtgtgtca gttagggtgt   2280
ggaaagtccc caggctcccc agcaggcaga agtatgcaaa gcatgcatct caattagtca   2340
```

```
gcaaccaggt gtggaaagtc cccaggctcc ccagcaggca gaagtatgca aagcatgcat   2400
ctcaattagt cagcaaccat agtcccgccc ctaactccgc ccatcccgcc cctaactccg   2460
cccagttccg cccattctcc gccccatggc tgactaattt tttttattta tgcagaggcc   2520
gaggccgcct cggcctctga gctattccag aagtagtgag gaggcttttt tggaggccta   2580
ggcttttgca aagatcgatc aagagacagg atgaggatcg tttcgcatga ttgaacaaga   2640
tggattgcac gcaggttctc cggccgcttg ggtggagagg ctattcggct atgactgggc   2700
acaacagaca atcggctgct ctgatgccgc cgtgttccgg ctgtcagcgc aggggcgccc   2760
ggttcttttt gtcaagaccg acctgtccgg tgccctgaat gaactgcaag acgaggcagc   2820
gcggctatcg tggctggcca cgacgggcgt tccttgcgca gctgtgctcg acgttgtcac   2880
tgaagcggga agggactggc tgctattggg cgaagtgccg gggcaggatc tcctgtcatc   2940
tcaccttgct cctgccgaga aagtatccat catggctgat gcaatgcggc ggctgcatac   3000
gcttgatccg gctacctgcc cattcgacca ccaagcgaaa catcgcatcg agcgagcacg   3060
tactcggatg gaagccggtc ttgtcgatca ggatgatctg gacgaagagc atcaggggct   3120
cgcgccagcc gaactgttcg ccaggctcaa ggcgagcatg cccgacggcg aggatctcgt   3180
cgtgacccat ggcgatgcct gcttgccgaa tatcatggtg gaaaatggcc gcttttctgg   3240
attcatcgac tgtggccggc tgggtgtggc ggaccgctat caggacatag cgttggctac   3300
ccgtgatatt gctgaagagc ttggcggcga atgggctgac cgcttcctcg tgctttacgg   3360
tatcgccgct cccgattcgc agcgcatcgc cttctatcgc cttcttgacg agttcttctg   3420
agcgggactc tggggttcga aatgaccgac caagcgacgc ccaacctgcc atcacgagat   3480
ttcgattcca ccgccgcctt ctatgaaagg ttgggcttcg gaatcgtttt ccgggacgcc   3540
ggctggatga tcctccagcg cggggatctc atgctggagt tcttcgccca ccctaggggg   3600
aggctaactg aaacacggaa ggagacaata ccggaaggaa cccgcgctat gacggcaata   3660
aaaagacaga ataaaacgca cggtgttggg tcgtttgttc ataaacgcgg ggttcggtcc   3720
cagggctggc actctgtcga taccccaccg agaccccatt ggggccaata cgcccgcgtt   3780
tcttcctttt ccccacccca ccccccaagt tcgggtgaag gcccagggct cgcagccaac   3840
gtcggggcgg caggccctgc catagcctca ggttactcat atatacttta gattgattta   3900
aaacttcatt tttaatttaa aaggatctag gtgaagatcc tttttgataa tctcatgacc   3960
aaaatccctt aacgtgagtt ttcgttccac tgagcgtcag accccgtaga aaagatcaaa   4020
ggatcttctt gagatccttt ttttctgcgc gtaatctgct gcttgcaaac aaaaaaacca   4080
ccgctaccag cggtggtttg tttgccggat caagagctac caactctttt tccgaaggta   4140
actggcttca gcagagcgca gataccaaat actgtccttc tagtgtagcc gtagttaggc   4200
caccacttca agaactctgt agcaccgcct acatacctcg ctctgctaat cctgttacca   4260
gtggctgctg ccagtggcga taagtcgtgt cttaccgggt tggactcaag acgatagtta   4320
ccggataagg cgcagcggtc gggctgaacg gggggttcgt gcacacagcc cagcttggag   4380
cgaacgacct acaccgaact gagataccta cagcgtgagc tatgagaaag cgccacgctt   4440
cccgaaggga gaaaggcgga caggtatccg gtaagcggca gggtcggaac aggagagcgc   4500
acgagggagc ttccaggggg aaacgcctgg tatctttata gtcctgtcgg gtttcgccac   4560
ctctgacttg agcgtcgatt tttgtgatgc tcgtcagggg ggcggagcct atggaaaaac   4620
gccagcaacg cggccttttt acggttcctg gccttttgct ggccttttgc tcacatgttc   4680
tttcctgcgt tatcccctga ttctgtggat aaccgtatta ccgccatgca t            4731
```

<210> SEQ ID NO 29
<211> LENGTH: 108
<212> TYPE: DNA
<213> ORGANISM: Artificial Sequenec
<220> FEATURE:
<223> OTHER INFORMATION: Synthetic Construct

<400> SEQUENCE: 29
ctgtacaagt ccggactcag atctcgagct caagcttcga attctgcagt cgacggtacc 60
gcgggcccgg gatccaccgg atctagataa ctgatcataa tcagccat 108

<210> SEQ ID NO 30
<211> LENGTH: 8
<212> TYPE: PRT
<213> ORGANISM: Artificial
<220> FEATURE:
<223> OTHER INFORMATION: Synthetic Construct

<400> SEQUENCE: 30

Asp Tyr Lys Asp Asp Asp Asp Lys
1 5

<210> SEQ ID NO 31
<211> LENGTH: 11
<212> TYPE: PRT
<213> ORGANISM: Artificial sequence
<220> FEATURE:
<223> OTHER INFORMATION: Synthetic Construct

<400> SEQUENCE: 31

Lys Pro Pro Thr Pro Pro Pro Glu Pro Glu Thr
1 5 10

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Tyr Pro Tyr Asp Val Pro Asp Tyr Ala
1 5

<210> SEQ ID NO 33
<211> LENGTH: 5427
<212> TYPE: DNA
<213> ORGANISM: Artificial Sequence
<220> FEATURE:
<223> OTHER INFORMATION: Synthetic Construct

<400> SEQUENCE: 33
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattcc    960
accacactgg actagtggat ccgagctcgg taccaagctt aagtttaaac cgctgatcag   1020
cctcgactgt gccttctagt tgccagccat ctgttgtttg cccctccccc gtgccttcct   1080
tgaccctgga aggtgccact cccactgtcc tttcctaata aaatgaggaa attgcatcgc   1140
attgtctgag taggtgtcat tctattctgg ggggtggggt ggggcaggac agcaaggggg   1200
aggattggga agacaatagc aggcatgctg gggatgcggt gggctctatg gcttctgagg   1260
cggaaagaac cagctggggc tctagggggt atccccacgc gccctgtagc ggcgcattaa   1320
gcgcggcggg tgtggtggtt acgcgcagcg tgaccgctac acttgccagc gccctagcgc   1380
ccgctccttt cgctttcttc ccttcctttc tcgccacgtt cgccggcttt ccccgtcaag   1440
ctctaaatcg ggggctccct ttagggttcc gatttagtgc tttacggcac ctcgacccca   1500
aaaaacttga ttagggtgat ggttcacgta gtgggccatc gccctgatag acggtttttc   1560
gccctttgac gttggagtcc acgttcttta atagtggact cttgttccaa actggaacaa   1620
cactcaaccc tatctcggtc tattcttttg atttataagg gattttgccg atttcggcct   1680
attggttaaa aaatgagctg atttaacaaa aatttaacgc gaattaattc tgtggaatgt   1740
gtgtcagtta gggtgtggaa agtccccagg ctccccagca ggcagaagta tgcaaagcat   1800
gcatctcaat tagtcagcaa ccaggtgtgg aaagtcccca ggctccccag caggcagaag   1860
tatgcaaagc atgcatctca attagtcagc aaccatagtc ccgcccctaa ctccgcccat   1920
cccgccccta actccgccca gttccgccca ttctccgccc catggctgac taattttttt   1980
tatttatgca gaggccgagg ccgcctctgc ctctgagcta ttccagaagt agtgaggagg   2040
cttttttgga ggcctaggct tttgcaaaaa gctcccggga gcttgtatat ccattttcgg   2100
atctgatcaa gagacaggat gaggatcgtt tcgcatgatt gaacaagatg gattgcacgc   2160
aggttctccg gccgcttggg tggagaggct attcggctat gactgggcac aacagacaat   2220
cggctgctct gatgccgccg tgttccggct gtcagcgcag gggcgcccgg ttctttttgt   2280
caagaccgac ctgtccggtg ccctgaatga actgcaggac gaggcagcgc ggctatcgtg   2340
gctggccacg acgggcgttc cttgcgcagc tgtgctcgac gttgtcactg aagcgggaag   2400
ggactggctg ctattgggcg aagtgccggg gcaggatctc ctgtcatctc accttgctcc   2460
tgccgagaaa gtatccatca tggctgatgc aatgcggcgg ctgcatacgc ttgatccggc   2520
tacctgccca ttcgaccacc aagcgaaaca tcgcatcgag cgagcacgta ctcggatgga   2580
agccggtctt gtcgatcagg atgatctgga cgaagagcat caggggctcg cgccagccga   2640
actgttcgcc aggctcaagg cgcgcatgcc cgacggcgag gatctcgtcg tgacccatgg   2700
cgatgcctgc ttgccgaata tcatggtgga aaatggccgc ttttctggat tcatcgactg   2760
tggccggctg ggtgtggcgg accgctatca ggacatagcg ttggctaccc gtgatattgc   2820
tgaagagctt ggcggcgaat gggctgaccg cttcctcgtg ctttacggta tcgccgctcc   2880
```

-continued

```
cgattcgcag cgcatcgcct tctatcgcct tcttgacgag ttcttctgag cgggactctg   2940
gggttcgaaa tgaccgacca agcgacgccc aacctgccat cacgagattt cgattccacc   3000
gccgccttct atgaaaggtt gggcttcgga atcgttttcc gggacgccgg ctggatgatc   3060
ctccagcgcg gggatctcat gctggagttc ttcgcccacc ccaacttgtt tattgcagct   3120
tataatggtt acaaataaag caatagcatc acaaatttca caaataaagc atttttttca   3180
ctgcattcta gttgtggttt gtccaaactc atcaatgtat cttatcatgt ctgtataccg   3240
tcgacctcta gctagagctt ggcgtaatca tggtcatagc tgtttcctgt gtgaaattgt   3300
tatccgctca caattccaca caacatacga gccggaagca taaagtgtaa agcctggggt   3360
gcctaatgag tgagctaact cacattaatt gcgttgcgct cactgcccgc tttccagtcg   3420
ggaaacctgt cgtgccagct gcattaatga atcggccaac gcgcggggag aggcggtttg   3480
cgtattgggc gctcttccgc ttcctcgctc actgactcgc tgcgctcggt cgttcggctg   3540
cggcgagcgg tatcagctca ctcaaaggcg gtaatacggt tatccacaga atcaggggat   3600
aacgcaggaa agaacatgtg agcaaaaggc cagcaaaagg ccaggaaccg taaaaaggcc   3660
gcgttgctgg cgtttttcca taggctccgc ccccctgacg agcatcacaa aaatcgacgc   3720
tcaagtcaga ggtggcgaaa cccgacagga ctataaagat accaggcgtt tccccctgga   3780
agctccctcg tgcgctctcc tgttccgacc ctgccgctta ccggatacct gtccgccttt   3840
ctcccttcgg gaagcgtggc gctttctcat agctcacgct gtaggtatct cagttcggtg   3900
taggtcgttc gctccaagct gggctgtgtg cacgaacccc ccgttcagcc cgaccgctgc   3960
gccttatccg gtaactatcg tcttgagtcc aacccggtaa gacacgactt atcgccactg   4020
gcagcagcca ctggtaacag gattagcaga gcgaggtatg taggcggtgc tacagagttc   4080
ttgaagtggt ggcctaacta cggctacact agaagaacag tatttggtat ctgcgctctg   4140
ctgaagccag ttaccttcgg aaaaagagtt ggtagctctt gatccggcaa acaaaccacc   4200
gctggtagcg gtttttttgt ttgcaagcag cagattacgc gcagaaaaaa aggatctcaa   4260
gaagatcctt tgatcttttc tacggggtct gacgctcagt ggaacgaaaa ctcacgttaa   4320
gggattttgg tcatgagatt atcaaaaagg atcttcacct agatcctttt aaattaaaaa   4380
tgaagtttta aatcaatcta aagtatatat gagtaaactt ggtctgacag ttaccaatgc   4440
ttaatcagtg aggcacctat ctcagcgatc tgtctatttc gttcatccat agttgcctga   4500
ctccccgtcg tgtagataac tacgatacgg gagggcttac catctggccc cagtgctgca   4560
atgataccgc gagacccacg ctcaccggct ccagatttat cagcaataaa ccagccagcc   4620
ggaagggccg agcgcagaag tggtcctgca actttatccg cctccatcca gtctattaat   4680
tgttgccggg aagctagagt aagtagttcg ccagttaata gtttgcgcaa cgttgttgcc   4740
attgctacag gcatcgtggt gtcacgctcg tcgtttggta tggcttcatt cagctccggt   4800
tcccaacgat caaggcgagt tacatgatcc cccatgttgt gcaaaaaagc ggttagctcc   4860
ttcggtcctc cgatcgttgt cagaagtaag ttggccgcag tgttatcact catggttatg   4920
gcagcactgc ataattctct tactgtcatg ccatccgtaa gatgcttttc tgtgactggt   4980
gagtactcaa ccaagtcatt ctgagaatag tgtatgcggc gaccgagttg ctcttgcccg   5040
gcgtcaatac gggataatac cgcgccacat agcagaactt taaaagtgct catcattgga   5100
aaacgttctt cggggcgaaa actctcaagg atcttaccgc tgttgagatc cagttcgatg   5160
taacccactc gtgcacccaa ctgatcttca gcatctttta ctttcaccag cgtttctggg   5220
tgagcaaaaa caggaaggca aaatgccgca aaaaagggaa taagggcgac acggaaatgt   5280
```

tgaatactca tactcttcct ttttcaatat tattgaagca tttatcaggg ttattgtctc 5340
atgagcggat acatatttga atgtatttag aaaaataaac aaataggggt tccgcgcaca 5400
tttccccgaa aagtgccacc tgacgtc 5427

<210> SEQ ID NO 34
<211> LENGTH: 21
<212> TYPE: RNA
<213> ORGANISM: Artificial Sequence
<220> FEATURE:
<223> OTHER INFORMATION: Synthetic Construct

<400> SEQUENCE: 34
ccaguuggau ggacacuaau u 21

<210> SEQ ID NO 35
<211> LENGTH: 21
<212> TYPE: RNA
<213> ORGANISM: Artificial Sequence
<220> FEATURE:
<223> OTHER INFORMATION: Synthetic Construct

<400> SEQUENCE: 35
uuacgaaggu accauagaau u 21

<210> SEQ ID NO 36
<211> LENGTH: 21
<212> TYPE: RNA
<213> ORGANISM: Artificial Sequence
<220> FEATURE:
<223> OTHER INFORMATION: Synthetic Construct

<400> SEQUENCE: 36
ggacagaagc cuuguacuau u 21

<210> SEQ ID NO 37
<211> LENGTH: 21
<212> TYPE: RNA
<213> ORGANISM: Artificial Sequence
<220> FEATURE:
<223> OTHER INFORMATION: Synthetic Construct

<400> SEQUENCE: 37
ccauugcugg ugccuacuau u 21

<210> SEQ ID NO 38
<211> LENGTH: 21
<212> TYPE: RNA
<213> ORGANISM: Artificial Sequence
<220> FEATURE:
<223> OTHER INFORMATION: Synthetic Construct

<400> SEQUENCE: 38 guuucacuc cagcuaacac a 21

<210> SEQ ID NO 39
<211> LENGTH: 21
<212> TYPE: RNA
<213> ORGANISM: Artificial Sequence
<220> FEATURE:
<223> OTHER INFORMATION: Synthetic Construct

<400> SEQUENCE: 39
uucaaaagug aggucgauug u 21

<210> SEQ ID NO 40

<211> LENGTH: 25
<212> TYPE: RNA
<213> ORGANISM: Artificial Sequence
<220> FEATURE:
<223> OTHER INFORMATION: Synthetic Construct

<400> SEQUENCE: 40
gcucacggaa cuaugagcug aguuu 25

<210> SEQ ID NO 41
<211> LENGTH: 1671
<212> TYPE: DNA
<213> ORGANISM: Homo sapiens

<400> SEQUENCE: 41
gcagtctgcg cgcggatggc cgcagcggcg atggcggcag cggcaggtgg aggggctggc 60
gcggcccgct ccctctcgcg cttccgaggc tgcctggctg gcgcgctgct cggggactgc 120
gtgggctcct tctacgaggc ccacgacacc gtcgacctga cgtcagtcct gcgtcatgtc 180
cagagtctgg agccggaccc cggcacgccc gggagtgagc ggacagaagc cttgtactac 240
acagatgaca cagccatggc cagggccctg gtgcagtccc tgctagccaa ggaggccttt 300
gacgaggtgg acatggctca cagatttgct caggagtaca agaaagaccc tgacaggggc 360
tatggtgctg gagtagtcac tgtcttcaag aagctcctga accccaaatg tcgcgatgtc 420
tttgagcctg cccgggccca gtttaacggg aaaggctcct atggcaatgg aggtgccatg 480
cgggtggctg gcatctccct ggcctatagc agtgtccagg atgtgcagaa gtttgcccgg 540
ctctcggccc agctgacaca cgcctcctcc ctgggttaca atggcgccat cctgcaggcc 600
ctggctgtgc acctggcctt gcagggcgag tcttccagcg agcactttct caagcaactc 660
ctgggccaca tggaggatct ggagggtgat gcccagtccg tcttggatgc cagggagttg 720
ggcatggagg agcgtccata ctccagccgc ctgaagaaga ttggagagct tctagaccag 780
gcatcggtga ccagggagga agtggtgtct gagctaggga atggcattgc tgcctttgag 840
tcggtaccca ccgccatcta ctgcttccta cgctgcatgg agccagaccc tgagatccct 900
tctgccttca atagcctcca aaggactctc atttattcca tctcacttgg tggggacaca 960
gacaccattg ccaccatggc tggggccatt gctggtgcct actatgggat ggatcaggtg 1020
ccagagagct ggcagcaaag ctgtgaaggc tacgaggaga cagacatcct ggcccaaagc 1080
ctgcaccgtg tcttccagaa gagttgatga gggctacagc tgttggggct ctgccaggtc 1140
ccctgggacc aactacagct ccaatcagaa accctgcgct tccttgagtg tggcttccca 1200
cttttcctgc attgtggagc tgactgagta caccggtgag gctggggtct ctgcagggga 1260
ggtcactgga acagcgagca agggactggt gcctcgctgg tgctgggtct ctggtttgct 1320
gcagagccgt aggacactcc tggctcctca gtaggacaga cagacgcagg cgggtttatt 1380
ttggaggggt acttgtggca ttttcctgta ttgtcttgga catgggatgt ggggaggtgg 1440
aaatgatgag cagtagcatc atttctccct gttgggtttt agccagtttg ccagcaagcg 1500
catcctagca gggtccccga gcagcaggtt gtgtggatga agggacaggc acttgcatcc 1560
agctgatcta ggtcacacct ggctcttggc tgccatgtgg cttattaaca gcttccagtg 1620
gaagtcgcaa taaacagttt ttggtaaatc tcaaaaaaaa aaaaaaaaaa a 1671

<210> SEQ ID NO 42
<211> LENGTH: 4276
<212> TYPE: DNA
<213> ORGANISM: Homo sapiens

<400> SEQUENCE: 42

```
cggtggtggg aaagtgaacg aatcccgaat caaagcggcg cattgaggca ggtggggtgc     60
cagtggaaga gagaaagcag gcgagtgttt acggcctgac ttgggaggcc ggcggatcag    120
caattgcaga agcaggcagc ggcagagagg gaatggtgca ggcaggcgct gagaaggacg    180
cgcagtccat ctctctcagg ttagtgaaat gaggctctcc gcccggggcc ggcccgggga    240
cagtgcgctg ctggtcccag catgaatgcg ggcccccggct gtgaaccctg caccaagcga    300
ccccgctggg gcgccgctac aacttcgccg gctgcttcgg acgcccggag ctttcccagc    360
aggcagaggc gcgtcctcga ccccaaggac gctcacgtgc agttcagggt cccaccgtcc    420
tcgccagcct gcgtcccagg gcgggcggga cagcacagag gcagcgccac ctcgcttgtt    480
ttcaaacaaa agactattac cagttggatg gacactaaag gaatcaagac agcggaatca    540
gaaagtttgg atagtaaaga aaacaacaat acaagaatag aatccatgat gagttctgta    600
caaaaagata acttttacca acataatgta gaaaaattag aaaatgtttc tcagctaagt    660
cttgataagt cacccactga aaaaagtaca cagtatttga accagcatca gactgcagca    720
atgtgtaagt ggcaaaatga agggaaacac acggagcagc ttttggaaag tgaacctcaa    780
acagtaaccc tggtaccaga gcagtttagt aatgctaaca ttgatcggtc acctcaaaat    840
gatgatcaca gtgacacaga tagtgaagag aatagagaca atcaacagtt tctcacaact    900
gtaaagcttg caaatgcaaa gcagactacg gaagatgaac aggccagaga agccaaaagc    960
caccagaagt gcagcaagtc ttgcgatcct ggggaagact gtgcaagttg tcagcaagat   1020
gagatagatg tggtgccaga gagtccattg tcagatgttg gctctgagga tgttggtact   1080
gggccaaaaa atgacaacaa attgactaga caagaaagtt gcctaggaaa ttctcctcca   1140
tttgagaagg aaagtgaacc cgagtcaccg atggatgtgg ataattctaa aaatagttgt   1200
caagactcag aagcagatga ggagacaagt ccaggttttg atgaacaaga agatggtagt   1260
tcctcccaaa cagcaaataa accttcaagg ttccaagcaa gagacgctga cattgaattt   1320
aggaaacggt actctactaa gggcggtgaa gttagattac atttccaatt tgaaggagga   1380
gagagtcgca ctggaatgaa tgatttaaat gctaaactac ctggaaatat ttctagcctg   1440
aatgtagaat gcagaaattc taagcaacat ggaaaaaagg attctaaaat cacagatcat   1500
ttcatgagac tgcccaaagc agaggacaga agaaaagaac agtgggaaac caaacatcaa   1560
agaacagaaa ggaagatccc taaatacgtt ccacctcacc tttctccaga taagaagtgg   1620
cttggaactc ccattgagga gatgagaaga atgcctcggt gtgggatccg gctgcctctc   1680
ttgagaccat ctgccaatca cacagtaact attcgggtag atcttttgcg agcaggagaa   1740
gttcctaaac cttttccaac acattataaa gatttgtggg ataacaagca tgttaaaatg   1800
ccttgttcag aacaaaattt gtacccagtg gaagatgaga atggtgagcg aactgcgggg   1860
agccggtggg agctcattca gactgcactt ctcaacaaat ttacacgacc ccaaaacttg   1920
aaggatgcta ttctgaaata caatgtggca tattctaaga aatgggactt tacagctttg   1980
atcgatttct gggataaggt acttgaagaa gcagaagctc aacatttata tcagtccatc   2040
ttgcctgata tggtgaaaat tgcactctgt ctgccaaata tttgcaccca gccaatacca   2100
ctcctgaaac agaagatgaa tcattccatc acaatgtcgc aggaacagat tgccagtctt   2160
ttagctaatg ctttcttctg cacatttcca cgacgaaatg ctaagatgaa atcggagtat   2220
tctagttacc cagacattaa cttcaatcga ttgtttgagg gacgttcatc aaggaaaccg   2280
gagaaactta aaacgctctt ctgctacttt agaagagtca cagagaaaaa acctactggg   2340
```

```
ttggtgacat ttacaagaca gagtcttgaa gattttccag aatgggaaag atgtgaaaaa   2400
cccttgacac gattgcatgt cacttacgaa ggtaccatag aagaaaatgg ccaaggcatg   2460
ctacaggtgg attttgcaaa tcgttttgtt ggaggtggtg taaccagtgc aggacttgtg   2520
caagaagaaa tccgcttttt aatcaatcct gagttgatta tttcacggct cttcactgag   2580
gtgctggatc acaatgaatg tctaattatc acaggtactg agcagtacag tgaatacaca   2640
ggctatgctg agacatatcg ttggtcccgg agccacgaag atgggagtga aagggacgac   2700
tggcagcggc gctgcactga gatcgttgcc atcgatgctc ttcacttcag acgctacctc   2760
gatcagtttg tgcctgagaa aatgagacgc gagctgaaca aggcttactg tggatttctc   2820
cgtcctggag tttcttcaga gaatctttct gcagtggcca caggaaactg ggctgtggt    2880
gcctttgggg gtgatgccag gttaaaagcc ttaatacaga tattggcagc tgctgcagct   2940
gagcgagatg tggtttattt cacctttggg gactcagaat tgatgagaga catttacagc   3000
atgcacattt tccttactga aaggaaactc actgttggag atgtgtataa gctgttgcta   3060
cgatactaca atgaagaatg cagaaactgt tccacccctg gaccagacat caagctttat   3120
ccattcatat accatgctgt cgagtcctgt gcagagaccg ctgaccattc agggcaaagg   3180
acagggacct gaggagccga gcgaatagca tctcctccca cctcccacca gagacgtcct   3240
gtttgagctg tcaggtgtaa tatatgaatt gacttaagtt aatataaatg tgtacataat   3300
ccacatttgt agtcaaggac gcaatctctt ccacacatgt gcagttgtca gttggtacat   3360
ctaaactccc tccatcctga ctcacgtgga cttagatatg ttttgtttct attttcttct   3420
atttcagttt ttcattcttt gatgtttatt tcttttgtcc atcagatctc ttgtgaaatc   3480
ccatggaagg ttgtgctcag cctgtcgggt ctctttcttc ctgcccatat attataccag   3540
ttgcttctgc agcccgcaga tgccagcgat gccaggaaac aagttgaaat ccaggaatct   3600
ctttaactga ttttgctaaa aatctccctg tgagccttcc actcaactct taatatgctt   3660
gcattgttta agtttttaaa ttctgaaaat taataattag ggtttttttc atatgtgttg   3720
cataatgcaa acctcctagg ttaaaatagt ttctttattt aagatagaat aatttccaga   3780
aattgtactt ttgaggtatc atttttatct gtaatggttt gtctgtcttt tttcctctga   3840
tcagtatttt tttataccag ttttggagac tggctgagat gaaaggaaat gtggaataaa   3900
aggaggtttt cctgatgtgg tgtaaagaaa acagattcaa gagaattgaa gatttttttt   3960
gtttcttggt actttttttct ttttaaatta ggactaatgt ttcttttgtg gtgcttgagg  4020
catattcata taaccaaagt ttgagaactg ggaacttcat gctgatttgt acatattgaa   4080
gtttctctgg tattcaaagg ttatatagtg aatgaatttt cattaataaa tcactttgtc   4140
agaaactccc atatcatcta tattttatat atgtatatat aaacgtatgc tctttaagtg   4200
tgtctatatg tgagcacata aaatctaaat aaaattggac tggtgggaaa caaaaaaaaa   4260
aaaaaaaaaa aaaaaa                                                   4276
```

<210> SEQ ID NO 43
<211> LENGTH: 25
<212> TYPE: RNA
<213> ORGANISM: Artificial Sequence
<220> FEATURE:
<223> OTHER INFORMATION: Synthetic Construct

<400> SEQUENCE: 43

```
cccaaguacu ucguggucac caaua                                         25
```

COMPOSITIONS AND METHODS FOR IDENTIFICATION OF PARP FUNCTION, INHIBITORS, AND ACTIVATORS

STATEMENT AS TO FEDERALLY FUNDED RESEARCH

This invention was made with government support under Grant Nos. R01 CA133404 and P01 CA42063, awarded by the NIH. The government has certain rights in this invention.

FIELD OF THE INVENTION

The present invention relates to the field of biochemistry and molecular biology.

BACKGROUND OF THE INVENTION

Poly-adenosine diphosphate (ADP)-ribose (PAR) polymers are the product of post-translational modifications carried out by PAR polymerases (PARPs). PAR is polymerized by PARPs onto acceptor proteins using nicotinamide adenine dinucleotide ($NAD^+$) as substrate (FIG. 1). PAR polymers are localized to distinct cellular structures in different phases of the cell cycle and localize to the mitotic spindle during mitosis (FIG. 2). There are at least 18 PARPs in the human genome, the domain structure for several PARPs is depicted in FIG. 3. However, the specific biological function and protein substrates of these PARPs are not fully characterized (Ame et al., *Bioessays* 26:882-893, 2004). The identification of the function and the substrates of each member of this family of proteins has been difficult to date.

PAR polymers are required for normal cell division and PARP knockouts in *Drosophila melanogaster* are embryonic lethal (Tulin et al., *Genes Dev.* 16:2108-2119, 2002). The concentration, length, and extent of PAR branching are regulated by a balance of activities of the PARPs and PAR glycohydrolase (PARG), a highly specific, processive endo- and exo-glycosidase (Hatakeyama et al., *J. Biol. Chem.* 261: 14902-14911, 1986). Poly-ADP-ribose polymers have generally been implicated for a role in several different human diseases including cancer, ischemic injury, inflammatory diseases, cardiovascular diseases, and neurodegenerative disorders.

We have discovered a role for several PARP proteins in the formation, nucleation, and disassembly of stress granules. Stress granules are distinct cellular structures that form in the cytosol upon exposure of a cell to stress conditions. Stress granules are composed of both proteins and RNA molecules. The RNA molecules present in stress granules are mRNA molecules stalled in translation pre-initiation complexes. Stress granules are typically 100 to 200 nM in size and are commonly associated with the endoplasmic reticulum.

Additional research tools to characterize the biological activities and substrates of each PARP and to aid in the understanding of the cellular pathways, substrate proteins, and nucleic acids regulated by poly-ADP-ribose are desired.

SUMMARY OF THE INVENTION

The present invention provides a nucleic acid encoding a PARP fusion protein comprising a nucleic acid sequence containing a nucleic acid sequence having at least 80% (e.g., at least 85%, 90%, 95%, 96%, 97%, 98%, 99%, or 100%) sequence identity to a PARP selected from PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5a (SEQ ID NO: 8 or 9), PARP 5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24), and a nucleic acid sequence encoding a polypeptide tag. In one embodiment of a nucleic acid of the invention, the polypeptide tag is positioned at the 5'-end of the nucleic acid sequence having at least 80% sequence identity to a PARP.

In another embodiment of the invention, the nucleic acid sequence encoding the polypeptide tag contains a nucleic acid sequence encoding a fluorescent protein (e.g., a green fluorescence protein having at least 95% sequence identity to SEQ ID NO: 25). In a different embodiment, the nucleic acid encoding the polypeptide tag contains a nucleic acid sequence that encodes at least one protease recognition sequence (e.g., at least one TEV protease recognition sequence of Glu-X-X-Tyr-X-Gln-Ser (SEQ ID NO: 26)). In another embodiment, the polypeptide tag contains a nucleic acid sequence that encodes a ZZ-domain having a sequence at least 80% identical (e.g., at least 85%, 90%, 95%, 99%, or 100% identical) to SEQ ID NO: 27. In an additional embodiment, the nucleic acid sequence encoding the polypeptide tag comprises a nucleic acid encoding a ZZ domain having a sequence at least 80% identical (e.g., at least 85%, 90%, 85%, 99%, or 100% identical) to SEQ ID NO: 27 and a nucleic acid sequence encoding at least one (e.g., 1, 2, 3, 4, 5, 6, or 7) TEV protease recognition sequence of SEQ ID NO: 26, wherein the sequence encoding the at least one TEV protease recognition sequence is located 3' of the sequence encoding the ZZ-domain.

The invention further provides a PARP fusion protein encoded by any of the above nucleic acids. The invention additionally provides antibodies (e.g., monoclonal or polyclonal antibodies) that specifically bind to one or more of the above PARP fusion proteins.

The invention also provides a transgenic cell (e.g., a mammalian cell) expressing one or more of the above nucleic acids. In one embodiment of a transgenic cell, one or more nucleic acids encoding a PARP fusion protein are positioned 3' of an inducible promoter. The invention also provides a cell lysate produced by one or more of the above transgenic cells. Another aspect of the invention provides kits containing one or more (e.g., 1, 2, 3, 4, 5, 6, 7, 8, 9, 10, 11, 12, 13, 14, 15, 16, 17, 18, 19, or 20 or more) of the above-described nucleic acids, PARP fusion proteins, antibodies, and/or transgenic cells, and optionally, one or more (e.g., 1, 2, 3, 4, or 5) labeled $NAD^+$ substrates.

The invention further provides a method for identifying an agent as a specific PARP inhibitor requiring the steps of: providing one or more of the above PARP fusion proteins; contacting the one or more PARP fusion proteins with the agent and a labeled nicotinamide adenine dinucleotide ($NAD^+$) substrate; and measuring the amount of labeled ADP-ribose covalently attached to the one or more PARP fusion proteins, whereby the label on the ADP-ribose is the same label on the $NAD^+$ substrate, and whereby an agent that decreases the amount of labeled ADP-ribose covalently attached to the one or more PARP fusion proteins is identified as a specific PARP inhibitor.

In an additional embodiment of the above methods, the agent specifically decreases the amount of labeled ADP-ribose covalently attached to one or more of a PARP1 fusion protein, a PARP2 fusion protein, a PAR5A fusion protein, a PARP5B fusion protein, a PARP7 fusion protein, a PARP8 fusion protein, a PARP14 fusion protein, and a PARP16 fusion protein of the invention. In another embodiment, the agent specifically decreases the amount of labeled ADP-ribose covalently attached to one or more of a PARP5A fusion protein, a PARP12 fusion protein, a PARP13.1 fusion protein, a PARP13.2 fusion protein, and a PARP15 fusion protein of the invention. In another embodiment, the agent specifically decreases the amount of labeled ADP-ribose covalently attached to a PARP13.1 fusion protein or a PARP11 fusion protein of the invention.

In additional embodiments of the above-described methods, the agent is a nucleic acid (e.g., a short RNA or DNA aptamer). In another embodiment, the test agent is an RNAi molecule.

In one embodiment of the method, an agent that results in at least a 5% (e.g., at least a 10%, 15%, 20%, 25%, 30%, 35%, 40%, 45%, 50%, 60%, 70%, 80%, 85%, 90%, 95%, 98, or even 100%) decrease in the amount of labeled ADP-ribose covalently attached to one or more (e.g., 1, 2, 3, 4, 5, 6, 7, 8, 9, 10, 11, 12, 13, 14, 15, 16, 17, or 18) PARP fusion proteins of the invention is identified as a specific PARP inhibitor.

The invention also provides methods for identifying an agent as a specific PARP activator requiring the steps of: providing one or more of the above-described PARP fusion proteins; contacting the one or more PARP fusion proteins with the agent and a labeled $NAD^+$ substrate; and measuring the amount of labeled ADP-ribose covalently attached to the one or more PARP fusion proteins, whereby the label on the ADP-ribose is the same label on the $NAD^+$ substrate, and whereby an agent that increase the amount of labeled ADP-ribose covalently attached to said one or more PARP fusion proteins is identified as a specific PARP activator.

In one embodiment of the above method, the agent specifically increases the amount of ADP-ribose covalently attached to one or more of a PARP1 fusion protein, a PARP2 fusion protein, a PAR5A fusion protein, a PARP5B fusion protein, a PARP7 fusion protein, a PARP8 fusion protein, a PARP14 fusion protein, and a PARP16 fusion protein of the invention. In another embodiment of the above method, the agent specifically increases the amount of labeled ADP-ribose covalently attached to one or more or a PARP5A fusion protein, a PARP12 fusion protein, a PARP13.1 fusion protein, a PARP13.2 fusion protein, and a PARP15 fusion protein of the invention. In another embodiment of the above method, the agent specifically increases the amount of labeled ADP-ribose covalently attached to a PARP13.1 fusion protein or a PARP11 fusion protein. In another embodiment of the above method, the agent is a nucleic acid.

In one embodiment of the method, an agent that results in at least a 5% (e.g., at least a 10%, 15%, 20%, 25%, 30%, 35%, 40%, 45%,50%, 55%, 60%, 70%, 80%, 85%, 90%, 95%, 98%, 100%, 150%, or 200%) increase in the amount of labeled ADP-ribose covalently attached to one or more (e.g., 1, 2, 3, 4, 5, 6, 7, 8, 9, 10, 11, 12, 13, 14, 15, 16, 17, or 18) PARP fusion proteins of the invention is identified as a specific PARP activator.

The invention further provides methods for identifying an agent that specifically binds one or more PARP fusion proteins requiring the steps of providing one or more (e.g., 1, 2, 3, 4, 5, 6, 7, 8, 9, 10, 11, 12, 13, 14, 15, 16, 17, 18, 19, or 20 or more) of the above-described PARP fusion proteins, contacting the one or more PARP fusion proteins with the agent, and determining whether the agent binds to the one or more PARP fusion proteins, wherein an agent that binds to the one or more PARP fusion proteins is deemed an agent that specifically binds one or more PARP fusion proteins. In additional embodiments of the method, the agent that specifically binds to one or more PARP fusion proteins is an inhibitor or activator of one or more PARP fusion proteins. In another embodiment, the method further requires one or more washing steps following said contacting of the one or more PARP fusion proteins with the agent.

In an additional embodiment of the method, the one or more PARP fusion proteins are attached to a bead that is present in a column. In desirable embodiments of the method, the agent specifically binds to one or more (e.g., 1, 2, 3, 4, 5, 6, 7, or 8) of a PARP1 fusion protein, a PARP2 fusion protein, a PARP5A fusion protein, a PARP5B fusion protein, a PARP7 fusion protein, a PARP8 fusion protein, a PARP14 fusion protein, and a PARP16 fusion protein of the invention. In another embodiment, the agent specifically binds to one or more (e.g., 1, 2, 3, 4, or 5) of a PARP5A fusion protein, a PARP12 fusion protein, a PARP13.1 fusion protein, a PARP13.2 fusion protein, and a PARP15 fusion protein of the invention. In additional embodiments of the method, the agent specifically binds to a PARP13.1 fusion protein or a PARP11 fusion protein of the invention. In an additional embodiment of the invention, the PARP fusion protein is purified from a cell lysate, a biological sample, or an extracellular medium using one or more (e.g., 1, 2, 3, 4, 5, 6, 7, 8, 9, or 10) antibodies of the invention (e.g., one or more antibodies that bind to one or more of the above-described PARP fusion proteins).

The invention also provides methods for determining the levels of one or more (e.g., 1, 2, 3, 4, 5, 6, 7, 8, 9, 10, 11, 12, 13, 14, 15, 16, 17, or 18) PARP proteins in a cell, cell lysate, biological sample, or extracellular medium requiring the steps of contacting a cell, cell lysate, biological sample, or extracellular medium with one or more (e.g., 1, 2, 3, 4, 5, 6, 7, 8, 9, or 10) antibodies of the invention, and detecting the binding of the one or more antibodies to one or more PARP proteins in the cell, cell lysate, biological sample, or extracellular medium. In another embodiment of the method, the one or more antibodies are polyclonal antibodies. In another embodiment, the one or more antibodies are washed one or more (e.g., 1, 2, 3, 4, or 5) times following contacting of the antibodies with the cell, cell lysate, biological sample, or extracellular medium.

In additional embodiments of the method, the binding of the one or more antibodies of the invention to the one or more PARP proteins is determined by immunoblotting, immunofluorescence microscopy, immunofluorescence-assisted cell sorting, enzyme-linked immunosorbent assay, or BIAcore. In additional embodiments of the method, the one or more antibodies of the invention are attached to a substrate (e.g., a bead) or a solid surface. In one embodiment, the one or more antibodies of the invention are attached to a bead that is present in a column.

In a desirable embodiment of the method, the one or more antibodies specifically bind to one or more (e.g., 1, 2, 3, 4, 5, 6, 7, or 8) of a PARP1 fusion protein, a PARP2 fusion protein, a PARP5A fusion protein, a PARP5B fusion protein, a PARP7 fusion protein, a PARP8 fusion protein, a PARP14 fusion protein, and a PARP16 fusion protein of the invention. In another embodiment of the method, the one or more antibodies specifically bind to one or more (e.g., 1, 2, 3, 4, or 5) of a PARP5A fusion protein, a PARP12 fusion protein, a PARP13.1 fusion protein, a PARP13.2 fusion protein, a PARP15 fusion protein of the invention. In another embodiment of the method, the one or more antibodies specifically bind to a PARP13.1 fusion protein or a PARP11 fusion protein.

In additional embodiments of the method, the one or more antibodies are contacted with a cell lysate and/or the antibodies are attached to the surface of a multi-well plate. In another embodiment of the method, the level of the one or more PARP proteins in a cell lysate, biological sample, or extracellular medium is compared to a control standard curve of the purified one or more PARP proteins or one or more purified PARP fusion proteins of the invention.

In all the above methods, the polypeptide tag of the one or more PARP fusion proteins contains a fluorescent protein (e.g., green fluorescence protein), an antigenic peptide sequence recognized by a specific monoclonal or polyclonal antibody (e.g., FLAG tag, DYKDDDDK (SEQ ID NO: 30); glutathione-S-transferase (GST) tag; KT3 flag, KPPTPPPEPET (SEQ ID NO: 31); and hemagglutinin tag, YPYDVPDYA (SEQ ID NO: 32)), or a specific peptide substrate recognized by a partner protein (e.g., biotin and streptavidin). In all the above methods, the one or more PARP fusion proteins may contain a polypeptide tag containing at least one (e.g., 1, 2, 3, 4, 5, 6, or 7) TEV protease recognition sequence of SEQ ID NO: 26 or a ZZ-domain having a sequence at least 95% identical to SEQ ID NO: 27. In all the above methods, the one or more PARP fusion proteins may contain a ZZ-domain having a sequence at least 95% identical to SEQ ID NO: 27 and at least one (e.g., 1, 2, 3, 4, 5, 6, or 7) TEV protease recognition site of SEQ ID NO: 26, wherein the TEV protease recognition sequence is located 3' of the ZZ-domain.

In each of the above methods of the invention, the labeled $NAD^+$ substrate is labeled with a radioisotope (e.g., $^{32}P$) or fluorophore, or is biotinylated. In any of the above methods, the one or more PARP fusion proteins may be purified or present in a cell lysate.

In any of the above methods, the agent may be a small molecule (e.g., a small molecule from a chemical library) or a polypeptide or peptide fragment (e.g., a polypeptide or peptide fragment present in a cell lysate). In any of the above methods, the one or more PARP fusion proteins may be attached to a substrate (e.g., a bead or a magnetic bead) or solid surface. In another embodiment of all the above methods, the method is performed in a multi-well plate or the one or more PARP fusion proteins are attached to the surface of a multi-well plate. In another embodiment of all the above methods, the one or more PARP fusion proteins are contacted with a bead, wherein the bead is covalently attached to a protein containing an Fc domain (e.g., IgG).

In an additional embodiment of all the above methods, the one or more PARP fusion proteins may be treated with a TEV protease, e.g., treated with a TEV protease following binding to a bead (e.g., a bead covalently attached to a protein containing an Fc domain).

By the term "biotinylated" is meant the covalent attachment of a biotin molecule to a small molecule, surface, or protein. A biotin molecule may be attached to a small molecule, surface, or protein using methods known in the art including, but not limited to, attachment to primary amines (e.g., epsilon-amines and N-terminal α-amines of a protein), as well as attachment at a sulfhydryl group, and a carboxyl group. Small molecules (e.g., $NAD^+$) and proteins (e.g., one or more of the PARP fusion proteins described herein) may be biotinylated. Biotinylated $NAD^+$ is available from a number of commercial sources including R & D Systems, Gentaur, and Trevigen (e.g., 6-biotin-17-NAD). Biotinylated small molecules and substrates may be specifically bound and/or purified using streptavidin, a protein that has a high affinity for biotin ($Ka{\sim}10^{13}\ M^{-1}$), or surfaces covalently attached to streptavidin (e.g., streptavidin-coated beads).

By the term "cell lysate" is meant the contents of the cell once the plasma membrane has been disrupted or permeabilized. Cell lysate also includes the contents of the intracellular organelles (e.g., endoplasmic reticulum, nucleus, mitochondria, chloroplasts, Golgi apparatus, and lysosome) upon disruption of their respective membranes. Cell lysate contains an unpurified mixture of proteins, small molecule metabolites, and nucleic acids (e.g., DNA and RNA). Cell lysate may be prepared from any type of cell, e.g., a mammalian cell (e.g. human, mouse, rat, and monkey cell), a bacterial cell, fungal cell, and a yeast cell. Cell lysate may be obtained by any methods known in the art including physical disruption (e.g., sonication, homogenization, or freeze/thaw procedures) or chemical disruption (e.g., treatment with a detergent (e.g., Triton-X-100 and NP-40)). Cell lysate may be prepared from a cell expressing one or more of the nucleic acid(s) of the invention that encode a one or more PARP fusion protein(s). Cell lysate may also be prepared from a cell arrested in a specific stage of the cell cycle (e.g., mitosis or S-phase) or may be prepared from asynchronous cells.

By the term "constitutive promoter" is meant a promoter that is placed 5' relative to a nucleic acid sequence encoding a protein, wherein the promoter regulates the consistent expression of a nucleic acid encoding a protein. The sequence of the constitutive promoter may be directly (no extraneous nucleotides) 5' to the first nucleotide of the sequence encoding the protein (e.g., a PARP fusion protein as described herein) or may be between 1-20 nucleotides, 1-100 nucleotides, 10-260 nucleotides, 100-700 nucleotides, or 100 to 2,000 nucleotides from the first nucleotide of the sequence encoding the protein. Examples of constitute promoters include, but are not limited to, bacterial promoters (e.g., *E. coli* $\sigma^{70}$, $\sigma^{S}$, $\sigma^{32}$, or $\sigma^{54}$ promoters; *B. subtilis* $\sigma^{A}$ or $\sigma^{B}$ promoters; T7 RNA polymerase-based promoters; and bacteriophage SP6 promoter), yeast promoters (e.g., pCyc, pAdh, pSte5, ADH1, cyc100, cyc70, cyc43, cyc28, cyc16, pPGK1, pCYC, GPD (TDH3), and CLB1 promoters), and mammalian promoters (e.g., cytomegalovirus immediate early gene-based promoters, SV40 early promoter, and Rous sarcoma virus promoter). A constitutive promoter may be used to mediate the expression of a nucleic acid (e.g., one or more nucleic acids encoding a PARP fusion protein as described herein) in a transgenic mammalian, bacterial, or yeast cell.

By "labeled nicotinamide adenine dinucleotide" or "labeled $NAD^+$" is meant a molecule of nicotinamide adenine dinucleotide ($NAD^+$) that is covalently labeled with a fluorescent molecule, labeled with a colorimetric molecule, labeled with a molecule that is recognized by a specific partner protein (e.g., biotinylation), or labeled with a radioisotope. One example of a labeled $NAD^+$ is biotinylated $NAD^+$ (e.g., 6-biotin-14-NAD). Examples of radiolabeled $NAD^+$ include, but are not limited to, $^{14}C$-adenine-$NAD^+$, $^{32}P$-$NAD^+$, and $^{3}H$-$NAD^+$. Additional examples of labeled $NAD^+$ are known in the art.

By the term "short RNA or DNA aptamer" is meant a short sequence of DNA or RNA nucleotides that bind to a specific target molecule (e.g., a protein or a target RNA or DNA molecule). A DNA or RNA aptamer that specifically binds to its target molecule (e.g., one or more of the nucleic acids encoding a PARP fusion protein or one or more of the PARP fusion proteins described herein) may decrease or increase the activity of the respective target molecule. For example, a specific DNA or RNA aptamer may bind to one or more of the above-described PARP fusion proteins and increase or decrease the poly-ADP ribosylation activity of the protein or the amount of poly-ADP ribose attached to the protein, or the levels of one or more PARP fusion proteins. The specific DNA aptamer may also bind to one or more nucleic acids (e.g., DNA or RNA) that encode a specific PARP protein (e.g., a nucleic acid that encodes a protein having at least 95% identity to PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24)), and mediate an increase or decrease in the expression of the PARP (e.g., mRNA and/or protein levels). A specific example of an RNA aptamer is an inhibitory RNA (RNAi) molecule. Methods for the design of RNAi molecules are known in the art.

By the term "fluorescent protein" is meant a protein that absorbs light of a specific wavelength (e.g., absorption wavelength) and emits light with a longer wavelength (e.g., emission wavelength). The term fluorescent protein encompasses natural fluorescent proteins (i.e., the natural form of the fluorescent protein without any genetic manipulations) and genetically mutated fluorescent proteins (e.g., fluorescent proteins engineered to change the identity of one or more amino acid residues). Several different examples of fluorescent proteins are known in the art, including, but limited to, green fluorescent proteins (e.g., GFP, Emerald, Superfolder GFP, Azami Green, mWasabi, TagGFP, TurboGFP, AcGFP, ZsGreen, T-Sapphire, and T-Sapphire), blue fluorescent proteins (e.g., EBFP, EBFP2, Azurite, mTagBFP), cyan fluorescent proteins (e.g., ECFP, mECFP, Cerulean, CyPet, AmCyan1, Midori-Ishi Cyan, TagCFP, mTFP1 (Teal)), yellow fluorescent proteins (e.g., EYFP, Topaz, Venus, mCitrine, YPet, TanYFP, PhiYFP, ZsYellow1, and mBanana), orange fluorescent proteins (e.g., Kusabira Orange, Kurabira Orange2, mOrange, mOrange2, dTomato, dTomato-Tandem, TagRFP, TagRFP-T, DsRed, DsRed2, DsRed-Express (T1), DsRed-Monomer, and mTangerine), and red fluorescent proteins (e.g., mRuby, mApple, mStrawberry, AsRed2, mRFP1, JRed, mCherry, HcRed1, mRaspberry, dKeima-Tandem, HcRed-Tandem, mPlum, and AQ143). Fluorescent proteins may be attached to the N- and/or C-terminus of a target protein (e.g., one or more of the PARP fusion proteins described herein). Fusion proteins tagged with a fluorescent protein (e.g., one or more of the PARP fusion proteins described herein) may be analyzed using fluorescence-based techniques known in the art (e.g., fluorescence microscopy, fluorescence plate readers, fluorescence assisted cell sorting, and use of a second antibody specific for the fluorescent protein).

By the term "inducible promoter" is meant a promoter that is placed 5' relative to a nucleic acid sequence encoding a protein, wherein the promoter induces (or represses) the expression of a nucleic acid upon addition (or removal) of a specific molecule or protein. The sequence of the inducible promoter may be directly (no extraneous nucleotides) 5' to the first nucleotide of the sequence encoding the protein (e.g., a PARP fusion protein as described herein) or may be between 1-20 nucleotides, 1-100 nucleotides, 10-260 nucleotides, 100-700 nucleotides, or 100 to 2,000 nucleotides from the first nucleotide of the sequence encoding the protein. Examples of inducible promoters include, but are not limited to alcohol dehydrogenase I gene promoters, tetracycline-responsive promoter systems, glucocorticoid receptor promoters, estrogen receptor promoter, ecdysone receptor promoters, metallothionein-based promoters, and T7-polymerase based promoters. An inducible promoter may be used to regulate the expression of a nucleic acid (e.g., one or more nucleic acids encoding a PARP fusion protein as described herein) in a transgenic mammalian, bacterial, or yeast cell.

By the term "nuclear lysate" is meant the contents of a nucleus upon disruption of the nuclear membrane. Nuclear lysate contains an unpurified mixture of proteins, small molecule metabolites, and nucleic acids (e.g., DNA and RNA). Nuclear lysate may be prepared from any type of nucleated cell, e.g., a mammalian cell (e.g. human, mouse, rat, and monkey cell), a fungal cell, and a yeast cell. Nuclear lysate may be obtained by any methods known in the art including stepped lysis using two different concentrations of detergents (e.g., NP-40) or a combination of physical treatment to rupture the plasma membrane and chemical treatment to rupture the nuclear membrane. Nuclear lysate may be prepared from a cell expressing one or more of the nucleic acid(s) of the invention that encode a one or more PARP fusion protein(s).

By "PAR" or "poly-ADP ribose" is meant a chain of two or more ADP-ribose molecules. The two or more molecules of ADP-ribose making up PAR may occur in a single linear chain or as a branched chain with one or more branches (e.g., at least 1, 2, 3, 4, 5, 6, 7, 8, 9, or 10 branches). Poly-ADP ribose may be attached to a specific substrate (e.g., protein, lipid, DNA, RNA, or small molecule) by the activity of one or more PARPs (e.g., one or more (e.g., 1, 2, 3, 4, 5, 6, 7, 8, 9, or 10, 11, 12, 13, 14, 15, 16, 17, 18, 19, 20, 21, or 22) of PARP1, PARP2, PARP3, PARP3.2, PARP3.3, PARP4, PARP5A, PARP5B, PARP6, PARP7, PARP8, PARP9, PARP10, PARP11, PARP12, PARP13.1, PARP13.2, PARP14, PARP15.1, PARP15.2, and PARP16) or removed by the activity of poly-ADP-ribose glycosidase or ARH3. Attachment of poly-ADP-ribose to a substrate protein may affect the biological activity of the protein, localization of the protein, or the identity and number of proteins that bind to the target substrate (e.g., protein). PARPs may also be modified by the covalent attachment of poly-ADP-ribose. The addition of poly-ADP ribose to a PARP may occur by "auto-modification" or "auto-modulation" (i.e., a specific PARP catalyzes the attachment of poly-ADP ribose to itself) or may occur by the activity of one or more (e.g., 1, 2, 3, 4, 5, 6, 7, 8, 9, or 10) other PARPs.

By the term "peptide fragment" is meant a protein having at least 2 amino acids (e.g., at least 5, 10, 15, 20, 25, 30, 35, 40, 45, 50, 55, 60, 65, 70, 75, 80, 85, 90, 95, or 100 amino acids), but having fewer amino acids than the wild-type protein. Non-limiting examples of peptide fragments have between 2 to 250 amino acids, 5 to 200 amino acids, between 5 to 150 amino acids, or between 5 to 100 amino acids. A peptide fragment may also represent a protein that has been processed to remove one or more (e.g., 1, 2, or 3) post-translational targeting sequences (e.g., nuclear localization sequence, ER-signal peptide, mitochondrial targeting signal, nuclear export sequence, or N-terminal secretion sequence).

By "poly-ADP ribose polymerase nucleic acid" or "PARP nucleic acid" is meant any nucleic acid containing a sequence that has at least 80% sequence identity (e.g., at least 85%, 90%, 95%, 96%, 97%, 98%, 99%, or even 100% sequence identity) to one or more of PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11

(SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24). A PARP nucleic acid encodes a protein that has a catalytic activity of attaching an ADP-ribose to a substrate (e.g., protein, DNA, RNA, lipid, or small molecule) or attaching one or more ADP-ribose molecules to a ADP-ribose molecule already attached to the substrate (e.g., protein, DNA, RNA, lipid, or small molecule) to create poly-ADP ribose.

By "poly-ADP ribose polymerase protein" or "PARP protein" is meant polypeptide containing a sequence having at least 80% identity (e.g., at least 85%, 90%, 95%, 96%, 97%, 98%, 99%, or even 100% identity) to a protein encoded by one or more of PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24). A PARP protein may contain one or more (e.g., 1, 2, 3, 4, 5, 6, 7, 8, 9, or 10) post-translational modifications, e.g., phosphorylation and ADP-ribosylation (e.g., at least 1, 2, 3, 4, 5, 6, 7, 8, 9, or 10 ADP-ribose molecules) on one or more amino acid residues. Post-translation modification of a PARP protein may occur within a cell (e.g., a transgenic cell described above) or in vitro using purified enzymes. PARP protein activity assays may be performed as described herein.

By "poly-ADP ribose polymerase fusion protein" or "PARP fusion protein" is meant a polypeptide containing a polypeptide tag and a sequence having at least 80% identity (e.g., at least 85%, 90%, 95%, 96%, 97%, 98%, 99%, or even 100% identity) to a protein encoded by one or more of PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24). The polypeptide tag of a PARP fusion protein may be located at the N- and/or C-terminus of the protein. The polypeptide tag may contain one or more of a fluorescent protein (e.g., a green fluorescence protein), a peptide epitope recognized by specific antibodies, a protein that is bound by a partner binding protein with high affinity (e.g., biotin and streptavidin), a $His_6$-tag, or one or more (e.g., 1, 2, 3, 4, 5, 6, or 7) protease recognition sequence(s) (e.g., one or more of a TEV protease or Factor Xa protease recognition sequence). The fusion proteins of the invention may be purified using antibodies specific for the polypeptide tag. For example, antibodies specific for the polypeptide tag or proteins that bind specifically to the protein sequence in the polypeptide tag may bound to a bead (e.g., a magnetic bead) or polymer surface in order to allow for the purification of the PARP fusion protein. A PARP fusion protein may also be purified and subsequently treated with one or more (e.g., 1, 2, or 3) protease(s) to remove the polypeptide tag from the PARP fusion protein. A PARP fusion protein preferably has the same cellular localization and biological activity as the wild-type PARP protein. Methods for the generation and purification of PARP fusion proteins are described herein.

By "PARP biological activity" is meant one or more (e.g., 1, 2, 3, 4, or 5) of the ability of a PARP fusion protein to catalyze the attachment of a single ADP-ribose to a target substrate (e.g., a protein, DNA, RNA, or lipid), the ability to attach one or more ADP-ribose molecules to a ADP-ribose molecule already attached to a substrate, the ability to add a branched ADP-ribose molecule to a pre-existing poly-ADP-ribose, the ability to localize to the cell nucleus, the ability to localize to stress granules, the ability to catalyze the formation or nucleate stress granules, the ability to catalyze the disassembly of stress granules, the ability to promote cell division or progression through mitosis, or the ability to activate or inhibit RNAi activity in the cell. Specific PARP proteins have a different subset of biological activities. For example, PARP1, PARP2, PARP5A, PARP5B, PARP7, PARP8, PARP14, and PARP16 have the ability to localize to the nucleus and play a role in mitosis and cell division. PARP5A, PARP12, PARP13.1, PARP13.2, and PARP-15 have the ability to localize to stress granules and play a role in the formation or nucleation of stress granules. PARP11 has the ability to localize to stress granules and plays a role in inhibiting stress granule formation or increasing the disassembly of stress granules. PARP13 inhibits the activity of RNAi in the cell. An additional PARP activity is "auto-modification" or "auto-modulation," that is, attachment of one or more ADP-ribose molecules to itself. Such auto-modulation of a PARP may result in an increase or decrease in any of the above-listed PARP activities. Assays for the measurement of the activity of each specific PARP are described herein.

By "polypeptide tag" is meant a protein sequence that is located at the 5' and/or 3' end of a polypeptide sequence of an expressed protein (e.g., one or more PARP proteins as described herein). A polypeptide tag may include one or more of a protease recognition sequence (e.g., 1, 2, 3, 4, 5, or 6 of the same or different protease recognition sequences), a epitope tag (e.g., 1, 2, 3, 4, or 5 epitope tags), a peptide that has a high affinity binding partner (e.g., biotin and streptavidin), or one or more (e.g., 1, 2, 3, or 4) tag(s) which aids in protein purification (e.g., a $His_6$ tag). The polypeptide tag may later be cleaved from the purified fusion protein by incubation with one or more (e.g., 1, 2, 3, or 4) protease(s) which cleaves the fusion protein at one or more protease recognition sequence(s) (e.g., 1, 2, 3, 4, 5, 6, or 7) within the sequence of the polypeptide tag. Examples of polypeptide tags are described herein.

By "positioned 3'" is meant a second nucleic acid sequence that is located after the 3' terminus of a first nucleic acid sequence (the second nucleotide sequence starts at the nucleotide following the 3' terminus of the first sequence) or the second nucleic acid sequence begins at a nucleotide that follows the 3' terminus of the first nucleic acid (e.g., the second nucleotide sequence starts at least 1, 2, 3, 4, 5, 6, 7, 8, 9, 10, 15, 20, 25, 30, 35, 40, 45, 50, 60, 70, 80, 90, 100, 200, 300, or 400 nucleotides following the 3' terminus of the first nucleic acid).

By "positioned 5'" is meant a second nucleic acid sequence that is located before the 5' terminus of a first nucleic acid sequence (the second nucleotide sequence ends at the nucleotide preceding the 5' terminus of the first sequence) or the second nucleic acid sequence ends at a nucleotide that precedes the 5' terminus of the first nucleic acid (e.g., the second nucleotide sequence ends at least 1, 2, 3, 4, 5, 6, 7, 8, 9, 10, 15, 20, 25, 30, 35, 40, 45, 50, 60, 70, 80, 90, 100, 200, 300, or 400 nucleotides before the 5' terminus of the first nucleic acid).

By the term “protease recognition sequence” is meant a short peptide sequence that is recognized as a substrate and cleaved by one or more proteases. Protease target sequences are often 3-20 amino acids in length and often require certain amino acids to be located at specific positions within the target sequence, while any amino acid may be placed at other positions within the target sequence. For example, the protease recognition sequence for TEV protease is Glu-X-X-Tyr-X-Gln-Ser (SEQ ID NO: 26), where X represents a position that may be filled by any amino acid. Additional examples of protease recognition sequences are known in the art and include, without limitation, factor Xa (Ile-Glu/Asp-Gly-Arg), Ala-64 subtilisin (Gly-Ala-His-Arg), clostripain (Arg and Lys-Arg), collagenase (Pro-Val-Gly-Pro), enterokinase (Asp-Asp-Asp-Asp-Lys), renin (Pro-Phe-His-Leu-Leu), and α-thrombin (Leu-Val-Pro-Arg-Gly-Ser). One or more of the same or different protease recognition sequence(s) may be included in the polypeptide tag of any of the PARP fusion proteins described herein. A protease recognition sequence may be placed 5' or 3' to an amino acid sequence to be removed from the protein. The polypeptide sequence of the protease recognition sequence may directly abut the sequence encoding a PARP or may be separated from the remaining coding sequence by one or more amino acids (e.g., 1, 2, 3, 4, 5, 6, 7, 8, 9, 10, 11, 12, 13, 14, 15, 16, 17, 18, 19, 20, 25, 30, 40, or 50 amino acids). An amino acid sequence that may be removed from the protein may include an antigenic sequence, $His_6$-tag, a fluorescent protein, a peptide sequence that has high affinity to a second protein that was used to purify the protein (e.g., $His_6$ tag or hemagglutinin tag), or a peptide sequence that was used to stabilize the protein during purification (e.g., albumin).

By the term “purified” is meant purified from other common components normally present within the cell. For example, a purified protein is purified away from the other cellular proteins, nucleic acids, and small metabolites present within the cell. A purified protein is at least 85% pure by weight (e.g., at least 90%, 95%, 96%, 97%, 98%, 99%, or even 100% pure) from other proteins, nucleic acids, or small metabolites present in the cell. A purified nucleic acid is at least 85% free of other contaminating nucleic acid molecules or adjoining sequences found in the cell.

By the term “RNAi” is meant a short double-stranded RNA molecule that mediates the down-regulation of a target mRNA in a cell. An RNAi molecule is typically 15 to 32 nucleotides in length. RNAi molecules are also known as siRNAs, small RNAs, or microRNAs. The design and therapeutic effectiveness of RNAi molecules is described in McCaffrey et al. (*Nature* 418:38-39, 2002). The RNAi molecules are at least 15 nucleotides, preferably, 17, 18, 19, 20, 21, 22, 23, 24, 25, 26, 27, 28, 29, 30, 31, 32, 33, 34, or 35 nucleotides in length and even up to 50 or 100 nucleotides in length (inclusive of all integers in between). Non-limiting examples of RNAi molecules are at least 80% identical (e.g., at least 85%, 90%, 95%, 96%, 97%, 98%, 99%, or even 100% identical) to or complementary to the translational start sequence or the nucleic acid sequence encoding the first 10, 20, 30, 40, 50, 60, 70, 80, 90, or 100 amino acids of a PARP selected from PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24). An RNAi molecule may target any part of the sequence encoding the target protein (e.g., any part of an mRNA encoding one of the above listed PARP proteins).

The specific requirements and modifications of small RNA are known in the art and are described, for example in PCT Publication No. WO01/75164, and U.S. Application Publication Nos. 20060134787, 20050153918, 20050058982, 20050037988, and 20040203145, the relevant portions of which are herein incorporated by reference. siRNAs can also be synthesized or generated by processing longer double-stranded RNAs, for example, in the presence of the enzyme dicer under conditions in which the dsRNA is processed to RNA molecules of about 17 to about 26 nucleotides. siRNAs can also be generated by expression of the corresponding DNA fragment (e.g., a hairpin DNA construct). Generally, the siRNA has a characteristic 2- to 3-nucleotide 3' overhanging ends, preferably these are (2'-deoxy) thymidine or uracil. The siRNAs typically comprise a 3' hydroxyl group. Single stranded siRNAs or blunt ended dsRNA may also be used. In order to further enhance the stability of the RNA, the 3' overhangs may be stabilized against degradation. For example, the RNA may be stabilized by including purine nucleotides, such as adenosine or guanosine. Alternatively, substitution of pyrimidine nucleotides by modified analogs, e.g., substitution of uridine 2-nucleotide overhangs by (2'-deoxy)thymidine is tolerated and does not affect the efficiency of RNAi. The absence of a 2' hydroxyl group significantly enhances the nuclease resistance of the overhang in tissue culture medium.

siRNA molecules can also be obtained through a variety of protocols including chemical synthesis or recombinant production using a *Drosophila* in vitro system. They can be commercially obtained from companies such as Dharmacon Research Inc. or Xeragon Inc., or they can be synthesized using commercially available kits such as the Silencer™ siRNA Construction Kit from Ambion (catalog number 1620) or HiScribe™ RNAi Transcription Kit from New England BioLabs (catalog number E2000S).

Alternatively siRNA can be prepared using standard procedures for in vitro transcription of RNA and dsRNA annealing procedures such as those described in Elbashir et al. (*Genes & Dev.,* 15:188-200, 2001), Girard et al. (*Nature* 442:199-202, 2006), Aravin et al. (*Nature* 442:203-207, 2006), Grivna et al. (*Genes Dev.* 20:1709-1714, 2006), and Lau et al. (*Science* 313:305-306, 2006). siRNAs may also be obtained by incubation of dsRNA that corresponds to a sequence of the target gene in a cell-free *Drosophila* lysate from syncytial blastoderm *Drosophila* embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs and the RNAs can then be eluted from the gel slices. In addition, chromatography (e.g., size exclusion chromatography), glycerol gradient centrifugation, and affinity purification with antibody can be used to isolate the small RNAs.

Short hairpin RNAs (shRNAs), as described in Yu et al. (*Proc. Natl. Acad. Sci USA,* 99:6047-6052, 2002) or Paddison et al. (*Genes & Dev,* 16:948-958, 2002), incorporated herein by reference, may also be used. shRNAs are designed such that both the sense and antisense strands are included within a single RNA molecule and connected by a loop of nucleotides (3 or more). shRNAs can be synthesized and purified using standard in vitro T7 transcription synthesis as described above and in Yu et al. (supra). shRNAs can also be subcloned into an expression vector that has the mouse U6 promoter sequences which can then be transfected into cells and used for in vivo expression of the shRNA.

A variety of methods and reagents are available for transfection, or introduction, of dsRNA into mammalian cells including but not limited to: TransIT-TKO™ (Mirus, Cat. # MIR 2150), Transmessenger™ (Qiagen, Cat. # 301525), Oligofectamine™ and Lipofectamine™ (Invitrogen, Cat. # MIR 12252-011 and Cat. #13778-075), siPORT™ (Ambion, Cat. #1631), and DharmaFECT™ (Fisher Scientific, Cat. # T-2001-01). Agents are also commercially available for electroporation-based methods for transfection of siRNA, such as siPORTer™ (Ambion Inc. Cat. # 1629). Microinjection techniques can also be used. The small RNA can also be transcribed from an expression construct introduced into the cells, where the expression construct includes a coding sequence for transcribing the small RNA operably-linked to one or more transcriptional regulatory sequences. Where desired, plasmids, vectors, or viral vectors can also be used for the delivery of dsRNA or siRNA and such vectors are known in the art. Protocols for each transfection reagent are available from the manufacturer. Additional methods are known in the art and are described, for example in U.S. Patent Application Publication No. 20060058255.

By the term "specifically binds" is meant a protein, nucleic acid (e.g., DNA or RNA), or molecule that binds one or more target molecules (e.g., polypeptides, DNA molecules, or RNA molecules) present in a cell, while not binding the majority of other proteins, DNA molecules, RNA molecules, or small molecules present within a cell, cell lysate, extracellular medium, or biological sample. For example, an antibody provided by the invention may bind to a single PARP-fusion protein or PARP protein, or may bind more than one (e.g., 2, 3, 4, 5, 6, 7, 8, 9, 10, 11, 12, 13, 14, 15, 16, 17, 18, 19, or 20 or more) PARP fusion proteins or PARP proteins in a cell, cell lysate, extracellular medium, or biological sample.

By "substrate" or "solid surface" is meant a surface on which a moiety or protein is covalently attached which allows for the binding and/or purification of a PARP fusion protein. The PARP fusion protein will bind to the substrate or solid surface through its polypeptide tag. Moieties or peptides covalently attached to the substrate or solid surface include, but are not limited to, monoclonal or polyclonal antibodies specific for an antigenic peptide in the polypeptide tag (e.g., anti-GFP antibody binding to GFP in the polypeptide tag), specific metal complexes bound by a peptide located in the polypeptide tag (e.g., $Ni^+$ binding to a $His_6$ polypeptide tag), or a specific binding protein for a peptide located in the polypeptide tag (e.g., IgG binding to a ZZ-domain in the polypeptide tag). Examples of a substrate or solid surface include, but are not limited to, a bead (e.g., a magnetic bead), a surface in a multi-well plate, and beads in column (e.g., column chromatography). A PARP fusion protein may be bound to a substrate or solid surface and eluted from the substrate or solid surface by contacting the substrate or solid surface with an elution buffer (e.g., a high salt elution buffer), a ligand that competes for binding to the substrate or solid surface or competes for binding to the polypeptide tag (e.g., a non-bound antibody that specifically binds to the protein in the polypeptide tag), or by treating the bound fusion protein with a protease that recognizes the one or more (e.g., 1, 2, 3, 4, 5, 6, or 7) specific cleavage recognition sequence(s) found in the polypeptide tag.

By the term "transgenic cell" is a meant a cell expressing one or more nucleic acids introduced by recombinant DNA technology. For example, a transgenic cell may express a nucleic acid encoding one or more (e.g., 1, 2, 3, 4, 5, 6, 7, 8, 9, 10, 11, 12, 13, 14, 15, 16, 17, or 18) of the presently described PARP fusion proteins. A transgenic cell may be a mammalian cell (e.g., a mouse, rat, monkey, or human cell), a bacterial cell, a fungal cell, or yeast cell. The transgenic cell may express the introduced nucleic acids from an inducible promoter or a constitutive promoter. The transgenic cell may also be located within a transgenic animal or may be cultured in tissue culture. The introduced one or more nucleic acid(s) may be integrated in the chromosome of a cell or may be expressed from a plasmid.

By "ZZ-domain" is meant a polypeptide sequence encoded by a nucleic acid having at least 80% identity (e.g., at least 85%, 90%, 95%, 96%, 97%, 98%, 99%, or even 100% identity) to the *Staphylcoccus aureus* protein A domain encoded by SEQ ID NO: 27. The ZZ domain has the ability to bind to Fcγ (the constant region of IgG involved in effector functions) and Fab (the Ig fragment responsible for antigen recognition). The specific structure and binding properties of the ZZ-domain are described in Graille et al. (*Proc. Natl. Acad. Sci. U.S.A.* 97:5399-5404, 2000) and Roben et al. (*J. Immunol.* 154:6437-6445, 1995). Expression of the ZZ-domain in the polypeptide tag allows for the purification of a fusion protein (e.g., one or more PARP fusion proteins as described herein) by the use of an Fc-containing protein (e.g., IgG).

Other features and advantages of the invention will be apparent from the following description of the preferred embodiments thereof, and from the claims.

BRIEF DESCRIPTION OF THE DRAWINGS

The application file contains at least one drawing executed in color (FIGS. 2, 9-11, 16-18, and 20-22). Copies of this patent or patent application with color drawings will be provided by the Office upon payment of the necessary fee.

FIG. 15 is a picture of the Bio-Gel P-6 structure and a picture of a Coomassie Blue-stained SDS-PAGE gel showing the use of Bio-Gel P-6 for the purification of proteins from a crude HeLa Kyoto cell extract. The SDS-PAGE gel shows the proteins present in cell extract (Extract), in cell extract following lectin clarification (Lectin Clarification), in the lysate prior to passing over the Bio-Gel P-6 resin (Input), in the pellet following centrifugation of the resin (Pellet), and in the eluate following treatment with poly-ADP-ribose glycohydrolase ARH3 (ARH3 Release).

FIG. 26A is picture of an immunoblot of a 4-12% SDS-PAGE gel containing proteins immunoprecipitated with an anti-GFP antibody from lysate from HeLa S3 cells transfected with a pEGFP-C1 plasmid expressing TIA1-GFP, PABP-GFP, G3BP-GFP, or Ago2-GFP following treatment with 0 or 20 nM pateamine A for 30 minutes. The immunoblot was developed using a polyclonal anti-poly-ADP-ribose antibody.

FIG. 26B is a picture of an immunoblot of an SDS-PAGE gel containing proteins immunoprecipitated from lysate from untransfected HeLa S3 cells using anti-G3BP and anti-Ago2 antibodies following treatment with 0 or 250 μM sodium arsenite for 60 minutes. The immunoblot was developed using a polyclonal anti-poly-ADP-ribose antibody.

FIG. 26C is a picture of an immunoblot of an SDS-PAGE gel containing proteins immunoprecipitated from lysate from HeLa S3 cells transfected with a pEGFP-C1 plasmid expressing G3BP1-GFP (full-length), G3BP1-A-GFP (domain A), G3BP1-ABC-GFP (domains A, B, and C), G3BP1-BC-GFP (domains B and C), G3BP1-BCD-GFP (domains B, C, and D), and G3BP1-D-GFP (domain D) following treatment with 0 or 250 μM sodium arsenite for 60 minutes. The immunoblot was developed using a polyclonal anti-poly-ADP-ribose antibody.

FIG. 26D is a picture of an immunoblot of an SDS-PAGE gel containing proteins immunoprecipitated from lysate from HeLa S3 cells transfected with a pEGFP-C1 plasmid expressing TIA1-GFP (full-length) or TIA1ΔRRM (mutant lacking RRM domain) following treatment with 0 or 250 μM sodium arsenite for 60 minutes. The immunoblot was developed using a polyclonal anti-poly-ADP-ribose antibody.

DETAILED DESCRIPTION

Figure 1:
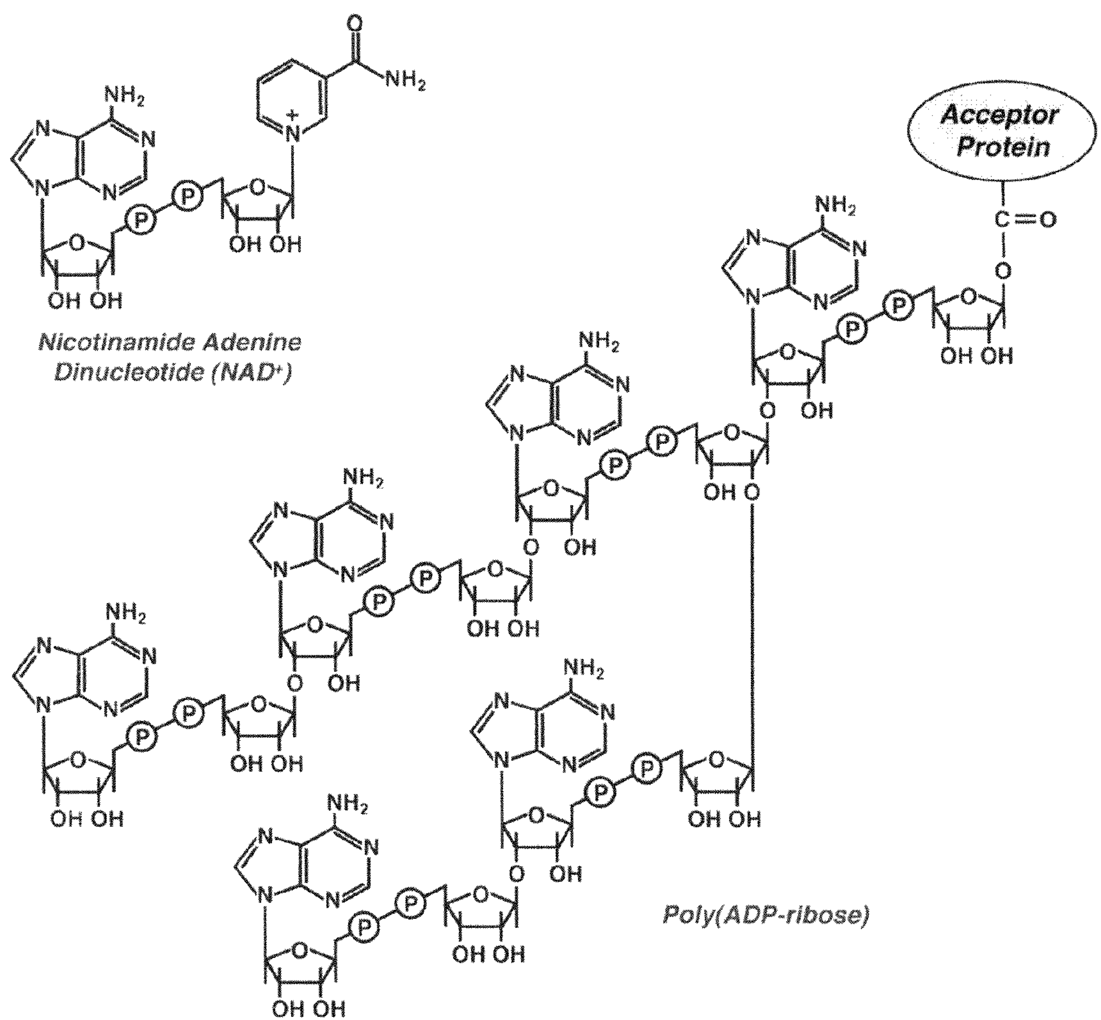
FIG. 1 is a picture of the chemical structure of nicotinamide adenine dinucleotide ($NAD^+$) and poly-ADP ribose.
Figure 2:
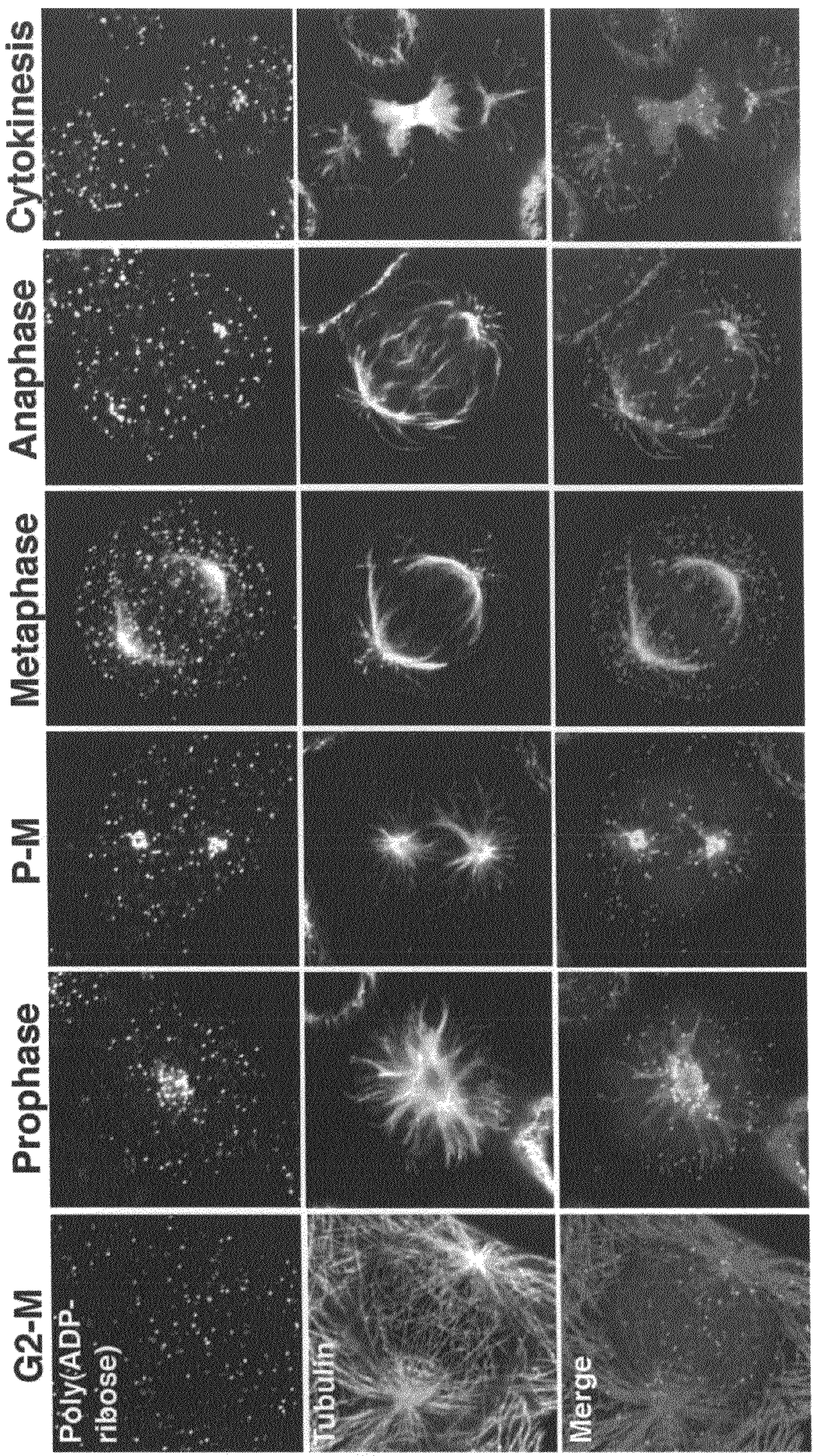
FIG. 2 is a set of micrographs showing the mitotic localization of poly-ADP ribose in HeLa cells during G2-M, prophase, prometaphase (P-M), metaphase, anaphase, and cytokinesis stages of the cell cycle using fluorescence microscopy following staining with rabbit anti-PAR antibodies labeled with Alexa 488 and X-rhodamine NHS esters.

We have discovered that specific PARP proteins or subsets of PARP proteins have unique biological activities in the cell. To address and further study the biological activities of specific PARP proteins, PARP fusion proteins and assays utilizing PARP fusion proteins were created. The PARP fusion proteins and assays provided by the invention allow for the identification of agents that inhibit, activate, or bind specific PARP proteins or subsets of PARPs, while having little (e.g., less than 40%, 30%, 25%, 20%, 15%, 10%, or 5% change (e.g., increase or decrease) in the biological activity) or no effect on one or more (e.g., 1, 2, 3, 4, 5, 6, 7, 8, 9, or 10) non-target PARPs, or fail to bind the one or more non-target PARPs.

For example, agents that specifically bind or inhibit the activity of PARPs involved in mitosis or cell division may be identified (e.g., an agent that specifically binds and/or inhibits the activity or decreases the expression of one or more (e.g., 1, 2, 3, 4, 5, 6, 7, or 8) of PARP1, PARP2, PARP5A, PARP5B, PARP7, PARP8, PARP14, and PARP16). Desirably, an agent that specifically binds and inhibits the activity or expression of PARP16 or a PARP16 fusion protein is identified.

Additional agents that inhibit the formation or nucleation of stress granules may be also identified (e.g., an agent that specifically binds and/or inhibits or decreases the expression of one or more (e.g., 1, 2, 3, 4, or 5) of PARP5A, PARP12, PARP13.1, PARP13.2, and PARP15. An additional agent that inhibits the formation or nucleation of stress granules is an agent that increases the activity and/or expression of PARP11 or a PARP11 fusion protein.

Additional agents that increase the activity of RNAi in a cell may be identified (e.g., an agent that specifically binds and/or inhibits or decreases the expression of PARP13.1 or a PARP13.1 fusion protein).

The PARP fusion proteins and assays provided herein will provide for the identification of additional biological activities of PARP proteins and will allow for the identification and development of therapeutics (e.g., antibodies, RNAi molecules, proteins, and small molecules) for the treatment of cell proliferative disorders (e.g., cancer) and stress granule related disorders. Stress granule-related disorders include the broad class of neurodegenerative diseases (e.g., Alzheimer's disease, Parkinson's disease, and multiple sclerosis), cardiovascular disorders, inflammatory disorders (e.g., autoimmune disorders, rheumatoid arthritis, asthma, glomerulonephritis, inflammatory bowel diseases, pelvic inflammatory disease, transplant rejection, and vasculitis), and ischemia/reperfusion injury. The PARP fusion proteins and assays provided by the invention will also allow for the identification of agents (e.g., agents that specifically bind and/or decrease the expression or activity of PARP13.1) that will increase the effectiveness of molecular therapies (e.g., the use of RNAi as a therapeutic molecule).

PARP Fusion Proteins

General Design

The invention provides PARP fusion proteins for each PARP. The PARP fusion proteins may be used to identify unique biological activities for each PARP protein and to identify specific inhibitors and activators for each PARP protein or subsets of PARP proteins. The invention provides nucleic acid sequences encoding these PARP fusion proteins. The nucleic acids contain a sequence that is at least 80% identical (e.g., at least 85%, 90%, 95%, 96%, 97%, 98%, 99%, or even 100% identical) to the full-length sequence of PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), or PARP16 (SEQ ID NO: 24).

The nucleic acids of the invention further contain nucleic acid sequences encoding one or two polypeptide tags. The nucleic acids encoding a polypeptide tag may be placed at a position 5' or a position 3' to the sequence encoding a PARP protein. For example, the 3' end of a nucleic acid sequence encoding a polypeptide tag may directly abut (i.e., no intervening nucleotides) the 5' end of a nucleic acid sequence encoding a PARP protein. In another example, the 5' end of a nucleic acid sequence encoding a polypeptide tag may directly abut (i.e., no intervening nucleotides) the 3' end of nucleic acid sequence encoding a PARP protein. In another example, one or more nucleotides (e.g., at least 2, 3, 4, 5, 10, 15, 20, 25, 30, 35, 40, 45, 50, 60, 70, 80, 90, 100, 200, 300, or 400 nucleotides) separate the 5' end of the sequence encoding the polypeptide tag from the 3' end of the sequence encoding a PARP protein, or separate the 3' end of the sequence encoding the polypeptide tag from the 5' end of the sequence encoding the PARP protein. Sequences encoding the polypeptide tags are described in further detail below

Polypeptide Tags

Polypeptide tags may be attached to a native protein sequence in order to aid in the purification of the protein, to label the protein for visualization in the cell, and to increase the thermodynamic stability or half-life of a protein. Nucleic acids encoding a polypeptide tag(s) may include one or more of the following sequences: a sequence encoding an epitope which may be recognized by a specific antibody recognizing the epitope (e.g., 1, 2, 3, 4 or 5 antigenic peptide sequences); a sequence encoding a protein that is bound with high affinity by a specific binding partner; one or more (e.g., 1, 2, 3, 4, or 5) sequence(s) encoding a peptide sequence that aids in purification (e.g., a $His_6$ tag); one or more (e.g., 1, 2, 3, 4, 5, 6, or 7) sequence(s) encoding a protease recognition sequence; and one or more (e.g., 1, 2, 3, or 4) sequences encoding a protein or a domain of a protein which increases the thermodynamic stability or half-life of the protein. The size of the nucleic acid sequence encoding the polypeptide tag may be between 1-50 nucleotides, 1-100 nucleotides, 1-200 nucleotides, 1-300 nucleotides, 1-400 nucleotides, 1-500 nucleotides, 200-500 nucleotides, 1-1,000 nucleotides, 1-5,000 nucleotides, 1-8,000 nucleotides, 1-10,000 nucleotides, or 1-20,000 nucleotides. Several polypeptide tags and sequences encoding polypeptide tags are known in the art. Non-limiting examples of sequences that may be incorporated in polypeptide tags are described below.

The nucleic acids encoding a polypeptide tag may contain sequences for one or more (e.g., 1, 2, 3, 4, or 5) epitopes or antigenic peptide sequences. Epitopes incorporated into polypeptide tags may be used to aid in the purification of a fusion protein, for e.g., by use of an antibody that specifically binds to the epitope. Examples of epitope sequences include, but are not limited to, a FLAG peptide (DYKDDDDK; SEQ ID NO: 30); a glutathione-S-transferase (GST) peptide; a KT3 peptide (KPPTPPPEPET; SEQ ID NO: 31); a hemagglutinin peptide (YPYDVPDYA; SEQ ID NO: 32), a calmodulin-binding peptide (*Methods in Molecular Biology: E. coli Gene Expression Protocols*, volume 205, Humana Press, 2003, pp. 79-97), a R-tag peptide (Jones et al., *Protein Expr. Purif.* 53:404-410, 2007), a V5 peptide, a c-myc peptide, and peptides derived from chitin-binding protein (CBP), CYD, Strep II, HPC, and maltose binding protein (MBP), as described in Lichty et al. (*Protein Expr. Purif.* 41:98-105, 2005).

Nucleic acids encoding a polypeptide tag may contain sequences for one or more (e.g., 1, 2, 3, 4, or 5) proteins with specific binding partners. Desirably, the specific binding partner has a high affinity (e.g., $K_D$<150 nM) to the peptide sequence in the polypeptide tag. Non-limiting examples of sequences that encode a protein with a high-affinity binding partner is biotin and the ZZ-domain of *S. aureus* protein A (e.g., a nucleic acid sequence with at least 80% identity to SEQ ID NO: 27). Additionally, the polypeptide tag may contain one or more peptide sequences that aid in the purification of the protein. Non-limiting examples of peptide sequences that aid in the purification of a protein include a $His_6$ tag, chitin-binding protein (CBP), maltose-binding protein (MBP), and glutathione-S-transferase (GST). For example, a protein containing a polypeptide tag containing a $His_6$ tag may be purified by passing a crude cellular lysate over a metal matrix (e.g., a $Ni^+$-Sepharose resin).

A polypeptide tag may also contain a sequence encoding a protein that increases the thermodynamic stability, half-life, or solubility of a protein. Non-limiting examples of peptides that increase the solubility of a protein include thioredoxin and poly(NANP). Additional non-limiting examples of proteins that increase the thermodynamic stability or half-life of a protein include the Fc domain of an antibody and albumin. A polypeptide tag may also contain one or more (e.g., 1, 2, 3, or 4) sequences encoding a protein that allows for the visualization of the fusion protein in the cell (e.g., a polypeptide tag containing a sequence encoding a fluorescent protein, such as green fluorescence protein).

A polypeptide tag may also contain one or more (e.g., 1, 2, 3, 4, 5, 6, or 7) protease recognition sequences. A fusion protein may be treated with one or more (e.g., 1, 2, 3, or 4) specific proteases that cleave the fusion protein at the one or more specific protease recognition sequences at any step in the purification process (e.g., after being bound to a resin or solid surface) to remove the polypeptide tag(s) from the remainder of the fusion protein. Non-limiting examples of protease recognition sequences include TEV protease (Glu-X-X-Tyr-X-Gln-Ser; SEQ ID NO: 26), factor Xa (Ile-Glu/Asp-Gly-Arg), Ala-64 subtilisin (Gly-Ala-His-Arg), clostripain (Arg and Lys-Arg), collagenase (Pro-Val-Gly-Pro), enterokinase (Asp-Asp-Asp-Asp-Lys), renin (Pro-Phe-His-Leu-Leu), and α-thrombin (Leu-Val-Pro-Arg-Gly-Ser). When a polypeptide tag is present at the N-terminus of a fusion protein, a protease recognition sequence is preferably located at a position 3' to a peptide sequence encoding an epitope, a sequence encoding a protein that is bound with high affinity by a specific binding partner, or a sequence encoding a peptide sequence that aids in purification. When a polypeptide tag is present at the C-terminus of a fusion protein, a protease recognition sequence is preferably located at a position 5' to a peptide sequence encoding an epitope, a sequence encoding a protein that is bound with high affinity by a specific binding partner, or a sequence encoding a peptide sequence that aids in purification. A polypeptide tag may contain one or more (e.g., 1, 2, 3, 4, 5, 6, or 7) of the same or different protease recognition sequences in tandem (i.e., without intervening amino acids) or with one or more (e.g., 1, 2, 3, 4, 5, 6, 7, 8, 9, or 10) intervening amino acids between each protease recognition sequence. Methods for the treatment of a fusion protein containing a protease recognition sequence in the polypeptide tag with a protease are known in the art.

Expression Vectors

A number of expression vectors for the expression of a nucleic acid encoding one or more nucleic acids encoding a PARP fusion protein of the invention are known in the art. Different examples of expression vectors are available for expression of the PARP fusion proteins in mammalian cells, insect cells, yeast cells, and bacterial cells. For example, the pEGFP-C1 mammalian vector (Invitrogen) contains a CMV promoter sequence, a nucleic acid sequence encoding green fluorescence protein, a multiple cloning site for insertion of nucleic acid sequence encoding a PARP nucleic acid (e.g., a sequence with 80% to one or more of SEQ ID NOS: 1-24). Additional non-limiting examples of publicly-available mammalian expression vectors include constitutive expression vectors Gateway® pDEST™26, pDEST™27, pDEST™40, and pDEST™47 (Invitrogen); adenoviral expression vectors (e.g., pAd/CM/V5-Dest Gateway® Vector Kit (Invitrogen); episomal expression vectors pCEP4 and pEBNA DEST (Invitrogen); lentiviral expression vectors (e.g., ViraPower™ Bsd; Invitrogen); and regulated expression vectors Gateway® pT-Rex™-DEST 30 and pT-Rex™-DEST 31 (Invitrogen). Non-limiting examples of bacterial expression vectors include Gateway® pDEST™14; Gateway® pDEST™15; Gateway® pDEST™17; Gateway® pDEST™24; Gateway® pET-DEST42; pEM7/Bsd; pEM7/Zeo; pRSET A, B, & C; pRSET-BFP; pRSET-CFP; pRSET-EmGFP; pTrcHIs A, B, & C; and pTrcHIs2 A, B, & C vectors (Invitrogen). Non-limiting examples yeast expression vectors include pAO815; pGAPZ A, B, & C; pPIC3.5K; pPIC9K; pTEF1/Bsd; pTEF1/Zeo; pYC2/CT; pYES2; pYES2/CT; and pYES3/CT (Invitrogen). Non-limiting examples of insect and baculovirus expression vectors include Gateway® pDEST™10; Gateway® pDEST™20; Gateway® pDEST™8; Gateway® pMT-DEST™48; pAC5.1/V5-His A, B, & C; pFastBac Dual; and pIB/V5-His-DEST (Invitrogen).

The expression vectors used to express a fusion protein may include one or more (e.g., 1, 2, 3, 4, or 5) constitutive promoter sequences and/or one or more (e.g., 1, 2, 3, 4, or 5) inducible promoter sequences. Non-limiting examples of constitutive promoter sequences include bacterial promoters (e.g., *E. coli* $\sigma^{70}$, $\sigma^{S}$, $\sigma^{32}$, or $\sigma^{54}$ promoters; *B. subtilis* $\sigma^{A}$ or $\sigma^{B}$ promoters; T7 RNA polymerase-based promoters; and a bacteriophage SP6 promoter), yeast promoters (e.g., pCyc, pAdh, pSte5, ADH1, cyc100, cyc70, cyc43, cyc28, cyc16, pPGK1, pCYC, GPD (TDH3), and CLB1 promoters), and mammalian promoters (e.g., cytomegalovirus immediate early gene-based promoters, SV40 early promoter, and Rous sarcoma virus promoter). Non-limiting examples of inducible promoter sequences include alcohol dehydrogenase I gene promoters, tetracycline-responsive promoter systems, glucocorticoid receptor promoters, estrogen receptor promoter, ecdysone receptor promoters, metallothionein-based promoters, and T7-polymerase based promoters. Several different mammalian expression vectors available that allow for the inducible expression of a nucleic acid sequence (e.g., a PARP fusion protein) are publicly available including pTet-On-Advanced (Clontech), pERV3 (Stratagene), pNEBR-R1 (New England BioLabs), and pCMV5-CymR (Qbiogene).

Transgenic Cells and Mammals

One or more nucleic acids encoding a PARP fusion protein may be introduced into a transgenic cell using methods known in the art, including, but not limited to electroporation, microinjection, lipid-mediated transfection (e.g., liposomal delivery systems), calcium phosphate-mediated transfection, DEAE-dextran mediated transfection, DNA transfection by biolistics, DNA transfection mediated by polybrene, and virus-mediated transduction.

The one or more nucleic acids encoding a PARP fusion protein may be introduced into any type of cell, including, but not limited to, a mammalian cell (e.g., a human, mouse, rat, monkey, or rabbit cell), a yeast cell, a bacterial cell, or an insect cell. A mammalian cell that expresses one or more nucleic acids encoding a PARP fusion protein may include a fibroblast, an epithelial cell, an endothelial cell, a smooth muscle cell, a hepatocyte, a kidney cell, and a lymphocyte. Additional examples of suitable mammalian cell lines include COS-7 monkey kidney cells, CV-1, L cells, C127, 3T3, Chinese hamster ovary (CHO), human embryonic kidney (HEK) cells, HeLa (e.g., HeLa S3 or HeLa Kyoto cells), 293, 293T, and BHK cell lines. One or more nucleic acids may also be expressed in a cell (e.g., a mammalian cell, a bacterial cell, or a yeast cell) that has been engineered to express one or more (e.g., 1, 2, 3, or 4) chaperone proteins, one or more (e.g., 1, 2, 3, or 4) enzymes that promote the post-translational modification of proteins, and/or contain one or more (e.g., 1, 2, 3, or 4) mutations in the nucleic acids encoding one or more (e.g., 1, 2, 3, or 4) proteins that have a negative effect on the expression of a transgenic protein (e.g., a PARP fusion protein), such as a specific RNAse or protease. An example of a bacterial cell that has been engineered to contain a mutation in an RNAse is BL21 Star™ (Invitrogen). A variety of cells are commercially available for the expression of one or more recombinant proteins (e.g., one or more PARP fusion proteins), including, but not limited to, bacterial competent cells (e.g., BL21-AI™ One Shot®, One Shot®-BL21(DE3), and One Shot®-BL21(DE3) pLysE, One Shot® BL21(DE3) pLysS (Invitrogen); and mammalian competent cells (e.g., Espresso Competent Hela S3 Cells, Espresso Competent CH0-K1 cells, and Espresso Competent HEK 293 cells (Neuromics), MaxPAK Competent HeLa S3 cells, MaxPAK Competent CHO-K1 cells, and MaxPAK Competent HEK 293 cells (Genlantis)).

A transgenic cell that contains one or more nucleic acids encoding a PARP fusion protein may a stable cell line (e.g., a cell that has integrated the one or more nucleic acids encoding a PARP fusion protein into one or more of its chromosomes). Alternatively, a transgenic cell may contain the one or more nucleic acids encoding a PARP fusion protein in a plasmid or on an artificial chromosome, which replicates independently of the chromosomes of the cell.

A transgenic mammal may also be produced from a transgenic cell containing one or more nucleic acids encoding a PARP fusion protein. A transgenic animal may be a mouse, a rat, a bovine, an ovine, a caprine, a porcine, a horse, a rabbit, or a monkey. The nucleic acid encoding one or more PARP fusion proteins may contain a tissue-specific promoter that allows the expression of one or more PARP fusion proteins into a biological fluid of the transgenic mammal (e.g., into the milk or serum of the transgenic mammal). For example, a protein may be engineered for expression in the milk of a mammal by placing the sequence encoding the protein downstream of the casein promoter (U.S. Pat. No. 4,873,316). A PARP fusion protein produced in a biological fluid of a transgenic mammal may be purified as described below.

Methods for the production of a transgenic mammal from a transgenic cell are known in the art and include, without limitation, methods that require the transfer of a nucleus from a transgenic cell to an enucleated oocyte and/or the microinjection of one or more nucleic acids (e.g., a plasmid or an artificial chromosome) encoding one or more PARP fusion proteins into an oocyte. Such genetically manipulated oocytes may then be transferred into a recipient female host to produce a transgenic mammal.

Cell Lysates

Cell lysates may be prepared from the transgenic cells containing a nucleic acid encoding one or more PARP fusion proteins of the invention. Cell lysates may be prepared by any methods known in the art, including both physical disruption methods and chemical disruption methods. Physical disruption methods include, but are not limited to sonication, homogenization, and rapid freeze/thaw lysis. Chemical disruption methods include, but are not limited to, the use of lysis buffers (e.g., buffers containing a detergent such as Triton-X-100 and NP-40). Following lysis of the cell membrane using chemical and/or physical disruption methods, the lysate may optionally be centrifuged to remove cellular debris and/or partially purified by one or more (e.g., 1, 2, 3, 4, 5, 6, or 7) of the following steps: salt gradient precipitation (e.g., ammonium sulfate precipitation), size exclusion chromatography or dialysis, and column chromatography (e.g., affinity chromatography, size exclusion chromatography, anion exchange chromatography, and cation exchange chromatography). The cell lysate may also be treated with one or more (e.g., 1, 2, or 3) of a DNAse, RNAse, or lipase prior to further use. One or more (e.g., 1, 2, 3, 4, or 5) protease inhibitors may also be added to the cell lysate prior to use.

PARP Fusion Protein Purification

One or more PARP fusion proteins may be fully or partially purified (e.g., at least 60% pure, at least 70% pure, at least 80% pure, at least 85% pure, at least 90% pure, at least 95% pure, and at least 99% pure from other proteins in the cell) from cell lysates or a biological fluid from a transgenic cell or a transgenic mammal expressing one or more (e.g., 1, 2, 3, 4, 5, 6, 7, 8, 9, 10, 11, 12, 13, 14, 15, 16, 17, 18, 19, or 20 or more) nucleic acids encoding a PARP fusion protein of the invention. Alternatively, one or more (e.g., 1, 2, 3, 4, 5, 6, 7, 8, 9, 10, 11, 12, 13, 14, 15, 16, 17, 18, 19, or 20 or more) PARP fusion proteins may be fully or partially purified from the extracellular medium of a transgenic cell expressing one or more nucleic acids encoding a PARP fusion protein of the invention. In each example, a cell lysate, biological fluid (e.g., milk or serum), or extracellular medium containing one or more PARP fusion proteins is collected.

Methods for the purification of a recombinant protein from a cell lysate, biological fluid, or extracellular medium are known in the art. For example, in instances where the PARP fusion protein contains an epitope, an antibody specific for the epitope (e.g., anti-GFP antibodies, anti-FLAG antibodies, anti-GST antibodies, anti-hemagglutinin antibodies, anti-c-myc antibodies, and anti-V5 antibodies) may be used to purify one or more PARP fusion protein(s). In another example, a PARP fusion protein may contain a polypeptide tag containing a sequence that aids in affinity purification of the protein (e.g., a $His_6$ tag, a calmodulin-binding protein tag, a glutathione S-transferase protein tag, a strep II tag, a HPC tag, a maltose-binding protein tag). In each example, a solid surface, resin, or bead (e.g., magnetic bead) may be covalently attached to a protein or molecule specifically bound by the protein sequence located in the polypeptide tag. In such instances, contacting the one or more PARP fusion protein(s) with the solid surface, resin, or bead will cause the selective binding of the one or more PARP fusion protein(s) with the solid surface, resin, or bead. The remaining non-bound proteins will not bind and may be washed away using an appropriate buffer. Specific methods for the affinity purification of proteins are known in the art.

One or more PARP fusion proteins may also be purified from a cell lysate, biological sample, or a extracellular medium by a purification protocol including, but limited to: salt precipitation (e.g., ammonium sulfate precipitation), pH precipitation, precipitation using organic solvents, high performance liquid chromatography (HPLC), column chromatography, ion exchange chromatography (e.g., cation exchange chromatography and anion exchange chromatography), immobilized metal affinity chromatography, gel filtration, or size exclusion chromatography or dialysis. One or more (e.g., 1, 2, 3, 4, 5, 6, or 7) of these steps may also be used in combination with an affinity purification step as described above.

The one or more purified PARP fusion proteins may be dialyzed to exchange the buffer or concentrated prior to use in one or more of the assays described herein (e.g., PARP activity assays or assays for the identification of a specific PARP activator or inhibitor). The one or more purified PARP fusion proteins may be stored at −70° C. in the presence or absence of one or more (e.g., 1, 2, 3, 4, or 5) stabilizing proteins including, but not limited to, albumin.

PARP Biological Activity

The biological activity of the one or more PARP fusion proteins of the invention include, but are not limited to, one or more (e.g., 1, 2, 3, 4, or 5) of the ability to covalently attach an ADP-ribose molecule to a substrate (e.g., a protein, a RNA molecule, a DNA molecule, or a lipid), the ability to covalently attach an ADP-ribose molecule to a ADP-ribose residue covalently attached to a substrate, the ability to add a branched ADP-ribose molecule to a pre-existing poly-ADP-ribose, the ability to localize to the cell nucleus, the ability to localize to stress granules, the ability to catalyze the formation or nucleation of stress granules, the ability to catalyze the disassembly of stress granules, the ability to promote cell division and mitosis, or the ability to inhibit RNAi activity in the cell. Specific PARP proteins have a different subset of biological activities: PARP1, PARP2, PARP5A, PARP5B, PARP7, PARP8, PARP14, and PARP16 have the ability to localize to the nucleus and/or the ability to promote cell division and mitosis; PARP5A, PARP12, PARP13.1, PARP13.2, and PARP15 have the ability to localize to stress granules and the ability to promote or nucleate stress granule formation; PARP11 has the ability to localize to stress granules and the ability to promote disassembly of stress granules; and PARP13.1 has the ability to decrease the activity of RNAi and the ability to add one or more ADP-ribose molecules to Argonaut.

Assays to measure the ability of one or more PARP fusion protein(s) to covalently attach an ADP-ribose to one or more (e.g., 1, 2, 3, 4, or 5) substrate(s) (e.g., a protein, a RNA, a DNA, or a lipid) involve the incubation of one or more PARP fusion protein(s) with the one or more substrate(s) in the presence of a labeled $NAD^+$ molecule (e.g., radiolabeled, fluorescently-labeled, and colorimetrically-labeled $NAD^+$). A radiolabeled $NAD^+$ substrate may contain one or more radioisotopes including, but not limited to, $^{14}C$ (e.g., $^{14}C$-adenine), $^{32}P$, and $^{3}H$. Additional $NAD^+$ substrates include fluorescently-labeled $NAD^+$ (Putt et al., *Anal. Biochem.* 78:326, 2004), colorimetrically-labeled $NAD^+$ (Nottbohn et al., *Agnew. Chem. Int. Ed.* 46:2066-2069, 2007), and biotinylated $NAD^+$ (6-biotin-17-NAD; R & D Systems). Following incubation of the one or more (e.g., 1, 2, 3, 4, 5, 6, 7, 8, 9, 10, 11, 12, 13, 14, 15, 16, 17, 18, 19, or 20 or more) PARP fusion proteins with the labeled $NAD^+$ and one or more (e.g., 1, 2, 3, 4, or 5) substrate molecules, the specific labeling of the substrate(s) with one or more labeled ADP-ribose molecules is determined by measuring the amount of the label associated with the $NAD^+$ covalently bound to the one or more substrate molecules. An increase in the amount of the label associated with the $NAD^+$ covalently bound to the one or more substrate(s) indicates PARP fusion protein activity.

In another example of a PARP assay, the auto-modification of one or more (e.g., 1, 2, 3, 4, 5, 6, 7, 8, 9, 10, 11, 12, 13, 14, 15, 16, 17, 18, 19, or 20 or more) PARP fusion protein(s) is measured by incubating the one or more PARP fusion proteins of the invention with a labeled $NAD^+$ substrate and subsequently, measuring the amount of the label associated with the $NAD^+$ covalently bound to the one or more PARP fusion proteins. An increase in the amount of the label associated with the $NAD^+$ covalently bound to the one or more PARP fusion proteins indicates PARP fusion protein auto-modification.

In an alternative assay, one or more (e.g., 1, 2, 3, 4, 5, 6, 7, 8, 9, 10, 11, 12, 13, 14, 15, 16, 17, 18, 19, or 20 or more) PARP fusion proteins may be incubated with one or more (e.g.,. 1, 2, 3, 4, or 5) substrates and a non-labeled $NAD^+$. The poly-ADP-ribosylation of the one or more substrates may be measured by contacting the one or more substrates with a poly-ADP-ribose antibody. For example, a sample of substrate proteins may be electrophoresed and immmunoblotted with an anti-poly-ADP-ribose antibody. An increased number of proteins or an increased level of detection using an anti-poly-ADP ribose antibody indicates an increase in the activity of the one or more PARP fusion proteins.

Assays to measure the ability of a PARP fusion protein to localize to a specific cellular structure or organelle using immunofluorescence microscopy are known in the art. For example, antibodies specific for one or more PARP fusion proteins and antibodies specific for one or more proteins or molecules specific for a cellular structure or organelle (e.g., cytoskeleton, mitochondria, trans-Golgi network, endoplasmic reticulum, early endosome, centrosome, GW bodies, nuclear envelope, lysosome, peroxisomes, histones, Cajal bodies, nucleus, and mitochondria) may be used to perform immunofluorescent microscopy. Localization of one or more PARP fusion proteins may be measured in high-throughput experiments by co-localization of one or more PARP fusion proteins with one or more proteins specific for a cellular structure or organelle (e.g., proteins listed in FIG. 10). Localization of one or more PARP fusion proteins in the nucleus may also be demonstrated by co-localization of a dye that stains DNA and an antibody that specifically binds the one or more PARP fusion proteins (e.g., co-localization of an antibody specific for one or more PARP fusion proteins and 4',6-diamindino-2-phenylindole (DAPI)).

Localization of one or more PARP fusion proteins to a specific cell structure or organelle may occur only during one or more (e.g., 1, 2, 3, 4, 5, or 6) specific stages of the cell cycle, including, but not limited to, G2-M, prophase, prometaphase (P-M), metaphase, anaphase, cytokinesis, $G_o$, and $G_1$ stages. For the purposes described herein, a PARP fusion protein is deemed to have the ability to localize to a specific cellular structure or organelle if it localizes to the specific cellular structure or organelle in at least one stage (e.g., mitosis or cytokinesis) of the cell cycle.

The ability of a PARP fusion protein to promote stress granule assembly or to inhibit stress granule assembly may be measured using fluorescence microscopy. In such a method, cells are treated with one or more PARP inhibitors, one or more PARP activators, or a nucleic acid encoding one or more PARP proteins or PARP fusion proteins, and are subsequently fixed and immunostained with antibodies specific for one or more stress granule protein (e.g., one or more of eIF3, eIF1A, eIF2α, eIF3η, eIF4A1, eIF4e, and G3BP). An increase in the number of foci containing one or more stress granule proteins (e.g., intense immunostaining in distinct cellular structures) indicates an increase in the formation of stress granules. A decrease in the number of foci containing one or more stress granule proteins, likewise, indicates a decrease in the formation of stress granules. In such assays, stress granule formation may be induced by exposure to stress conditions, for example, by treatment with sodium arsenite and pateamine A.

The ability of one of more PARP fusion proteins to promote cell division and mitosis may be measured using any method known in the art. For example, cell proliferation assays including, but not limited to, standard cell counting assays, BrdU labeling, and quantitative assays for DNA synthesis such as $^3$H-thymidine incorporation may be used to measure the ability of one or more PARP fusion proteins to promote cell division and mitosis. Likewise, inhibition of one or more PARP fusion proteins with the ability to promote cell division and mitosis may result in cell death. Several assays to measure cell death are known in the art, including, but not limited to Hoechst 33342 staining of chromatin, propidium iodide staining, annexin V staining of phosphoserine, and 3-(4,5-dimethylthiazol-2-yl)-2,5-diphenyl tetrazolium bromide (MTT) staining.

Assays for measuring RNAi activity in a cell are available in the art. For example, psiCHECK™-1 and psiCHECK™-2 assays systems provide methods for the measurement of RNAi activity in a cell. In these assays systems, *Renilla* luciferase is used a primary reporter gene and a target sequence (i.e., the target of one or more RNAi molecules) is cloned a multiple cloning region located downstream of the *Renilla* translational stop codon. Initiation of the RNAi process towards the target gene results in the cleavage and subsequent degradation of the fusion mRNA encoded by the psiCHECK vectors (i.e., upon treatment of the transfected cell with a vector-target RNAi molecule). Measurement of decreased *Renilla* luciferase activity in the psiCHECK™-transfected cells following treatment with the vector-target RNAi indicates the activity of RNAi in the cell. In experiments using the psiCHECK assay system, a cell transfected with the psiCHECK vector is treated with the vector-target RNAi and with an activator or inhibitor of one or more (e.g., 1, 2, 3, 4, 5, 6, 7, 8, 9, or 10) PARP fusion proteins (e.g., 1, 2, 3, 4, or 5 RNAi molecules targeting a specific PARP). Transfected cells treated with the vector-target RNAi and with a PARP inhibitor or activator that demonstrate increased *Renilla* luciferase activity relative to a transfected cell treated with the vector-target RNAi alone indicate that the specific targeted PARP activates or inhibits RNAi activity in the cell, respectively. Cells treated with a PARP inhibitor or activator that demonstrate decreased *Renilla* luciferase activity relative to a cell treated with vector-target RNAi alone indicate that the specific targeted PARP inhibits or activates RNAi activity in the cell, respectively.

Figure 3:
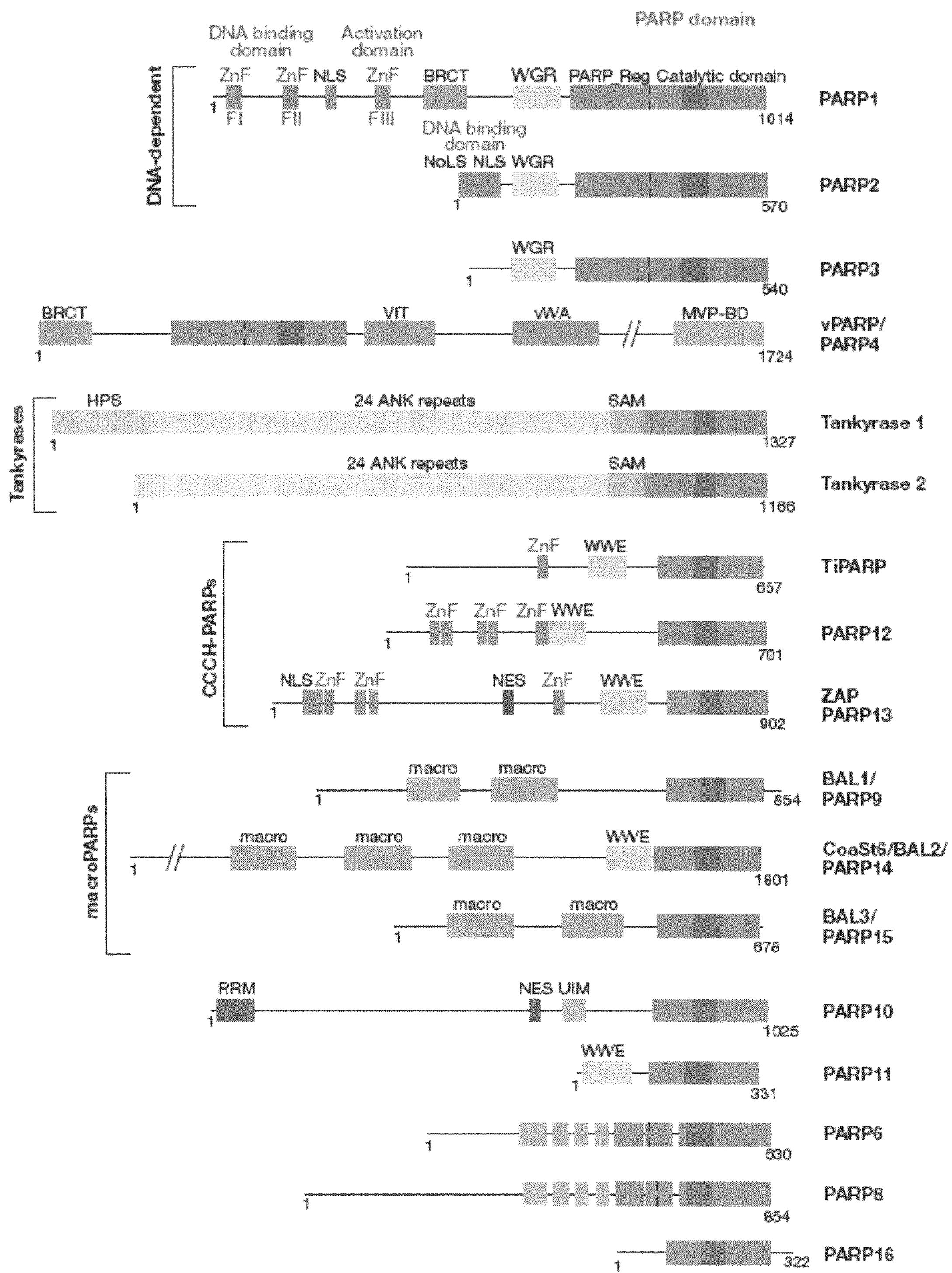
FIG. 3 is a set of schematic diagrams showing the domain organization of PARP1, PARP2, PARP3, PARP4, tankyrase 1 (PARP5A), tankyrase 2 (PARP5B), TiPARP (PARP7), PARP12, PARP13, PARP9, PARP14, PARP15, PARP10, PARP11, PARP6, PARP8, and PARP16.

Any of the above-referenced PARP activity assays may be performed to determine the activity of PARP protein sequence encoded by a nucleic acid having at least 80% sequence identity to one of SEQ ID NOS: 1-24. The domain structure of several PARP proteins are shown in FIG. 3. Preferred mutations in the wild-type sequences of PARP proteins (e.g., SEQ ID NOS: 1-24) do not introduce amino acid changes in any of the conserved domains shown in FIG. 3 (e.g., catalytic domain, nuclear localization sequence, zinc finger domain, nuclear export sequence, WWE domain, RRM domain, and BRCT domain). In addition, the biological activity of a PARP fusion protein containing a sequence having at least 80% sequence identity to one of SEQ ID NOS: 1-24 may be assessed using any of the above-described cellular or in vitro assays.

PARP-Specific Antibodies

Antibodies specific to the one or more (e.g., 1, 2, 3, 4, 5, 6, 7, 8, 9, 10, 11, 12, 13, 14, 15, 16, 17, 18, 19, or 20 or more) PARP fusion proteins of the invention can be generated using standard methods, such as those described herein. Antibodies specific for one or more PARP fusion proteins, PARP proteins, or fragments of PARP proteins or PARP fusion proteins may be used in quantitative assays to measure to amount of one or more (e.g., 1, 2, 3, 4, 5, 6, 7, 8, 9, 10, 11, 12, 13, 14, 15, 16, 17, 18, 19, or 20 or more) PARP proteins present in a cell, cell lysate, biological sample, or extracellular medium. Antibodies specific to the one or more (e.g., 1, 2, 3, 4, 5, 6, 7, 8, 9, 10, 11, 12, 13, 14, 15, 16, 17, 18, 19, or 20 or more) PARP fusion proteins of the invention may also be used to identify specific binding partners or potential inhibitors or activators of the one or more PARP fusion proteins or one or more PARP proteins.

For the preparation of polyclonal antibodies reactive with one or more PARP fusion proteins or PARP proteins, one or more PARP protein(s), PARP fusion protein(s), fragments of PARP protein(s), or fragments of PARP fusion protein(s) can be purified from natural sources (e.g., cultures of cells expressing one or more PARP proteins) or synthesized in, e.g., mammalian, insect, or bacterial cells by expression of corresponding DNA sequences contained in a suitable cloning vehicle (e.g., the nucleic acids encoding PARP proteins and PARP fusion proteins described herein). Fusion proteins are commonly used as a source of antigen for producing antibodies. The antigenic proteins can be optionally purified, and then coupled to a carrier protein, mixed with Freund's adjuvant to enhance stimulation of the antigenic response in an inoculated animal, and injected into rabbits, mice, or other laboratory animals. Primary immunizations are carried out with Freund's complete adjuvant and subsequent immunizations performed with Freund's incomplete adjuvant. Following booster injections at bi-weekly intervals, the inoculated animals are then bled and the sera isolated. The sera is used directly or is purified prior to use by various methods, including affinity chromatography employing reagents such as Protein A-Sepharose, antigen-Sepharose, and anti-horse-Ig-Sepharose. Antibody titers can be monitored by Western blot and immunoprecipitation analyses using one or more PARP proteins, PARP fusion proteins, or fragments of PARP fusion proteins or PARP proteins. Immune sera can be affinity purified using one or more PARP proteins, PARP fusion proteins, or fragments of PARP fusion proteins or PARP proteins coupled to beads. Antiserum specificity can be determined using a panel of proteins, such as one or more PARP proteins, PARP fusion proteins, or fragments of PARP fusion proteins or PARP proteins.

Alternatively, monoclonal antibodies are produced by removing the spleen from the inoculated animal, homogenizing the spleen tissue, and suspending the spleen cells suspended in phosphate buffered saline (PBS). The spleen cells serve as a source of lymphocytes, some of which produce antibody of the appropriate specificity. These cells are then fused with permanently growing myeloma partner cells, and the products of the fusion plated into a number of tissue culture wells in the presence of selective agents, such as hypoxanthine, aminopterine, and thymidine (Mocikat, *J. Immunol. Methods* 225:185-189, 1999; Jonak et al., *Hum. Antibodies Hybridomas* 3:177-185, 1992; Srikumaran et al., *Science* 220:522, 1983). The wells can then be screened by ELISA to identify those containing cells making antibody capable of binding to one or more PARP proteins, PARP fusion proteins, fragments of PARP proteins, or fragments of PARP fusion proteins, or mutants thereof. These cells can then be re-plated and, after a period of growth, the wells containing these cells can be screened again to identify antibody-producing cells. Several cloning procedures can be carried out until over 90% of the wells contain single clones that are positive for specific antibody production. From this procedure, a stable cell line of clones that produce the antibody are established. The-monoclonal antibody can then be purified by affinity chromatography using Protein A Sepharose and ion-exchange chromatography, as well as variations and combinations of these techniques. Once produced, monoclonal antibodies are also tested for specific PARP protein or PARP fusion protein recognition by ELISA, Western blot, and/or immunoprecipitation analysis (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., In Monoclonal Antibodies and T Cell Hybridomas, Elsevier, New York, N.Y., 1981).

As an alternate or adjunct immunogen to a PARP protein or PARP fusion protein, peptides corresponding to relatively unique regions of a PARP protein or PARP fusion protein can be generated and coupled to keyhole limpet hemocyanin (KLH) through an introduced C-terminal lysine. Antiserum to each of these peptides can be similarly affinity-purified on peptides conjugated to BSA, and specificity tested by ELISA and Western blotting using peptide conjugates, and by Western blotting and immunoprecipitation using a PARP protein, PARP fusion protein, or fragment of a PARP protein or PARP fusion protein.

Antibodies of the invention are desirably produced using PARP protein or PARP fusion protein amino acid sequences that do not reside within highly conserved regions, and that appear likely to be antigenic, as evaluated by criteria such as those provided by the Peptide Structure Program (Genetics Computer Group Sequence Analysis Package, Program Manual for the GCG Package, Version 7, 1991) using the algorithm of Jameson et al., *CABIOS* 4:181, 1988. These fragments can be generated by standard techniques, e.g., by PCR, and cloned into any appropriate expression vector. For example, GST fusion proteins can be expressed in *E. coli* and purified using a glutathione-agarose affinity matrix. To minimize the potential for obtaining antisera that is non-specific or exhibits low-affinity binding to one or more PARP proteins, PARP fusion proteins, or fragments of PARP proteins or PARP fusion proteins, two or three PARP fusion proteins may be generated for each fragment injected into a separate animal. Antisera are raised by injections in series, preferably including at least three booster injections.

In addition to intact monoclonal and polyclonal anti-PARP protein or anti-PARP fusion protein antibodies, various genetically engineered antibodies and antibody fragments (e.g., F(ab')2, Fab', Fab, Fv, and sFv fragments) can be produced using standard methods. Truncated versions of monoclonal antibodies, for example, can be produced by recombinant methods in which plasmids are generated that express the desired monoclonal antibody fragment(s) in a suitable host. Ladner (U.S. Pat. Nos. 4,946,778 and 4,704,692) describes methods for preparing single polypeptide chain antibodies. Ward et al., *Nature* 341:544-546, 1989, describes the preparation of heavy chain variable domain which have high antigen-binding affinities. McCafferty et al. (*Nature* 348:552-554, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describes various methods for producing immunoglobulins, and immunologically functional fragments thereof, that include at least the variable domains of the heavy and light chains in a single host cell. Cabilly et al. (U.S. Pat. No. 4,816,567) describes methods for preparing chimeric antibodies. In addition, the antibodies can be coupled to compounds, such as toxins or radiolabels.

Methods for Identification of Specific PARP Inhibitors or Activators

The PARP fusion proteins of the invention may be used to identify one or more (e.g., 1, 2, 3, 4, 5, 6, 7, 8, 9, 10, 11, 12, 13, 14, 15, 16, 17, 18, 19, or 20 or more) specific PARP activators or inhibitors. In the provided assays, one or more (e.g., 1, 2, 3, 4, 5, 6, 7, 8, 9, 10, 11, 12, 13, 14, 15, 16, 17, 18, 19, or 20 or more) PARP fusion proteins are contacted with an agent (e.g., a test agent) and a labeled $NAD^+$ (e.g., a colorimetrically-labeled, fluorescently-labeled, biotinylated-, or radioisotope-labeled $NAD^+$), and measuring the amount of labeled ADP-ribose covalently attached to the one or more PARP fusion proteins of the invention. In a method for identifying an agent that is a specific PARP inhibitor, the agent mediates a decrease (e.g., at least a 5%, 10%, 15%, 20%, 25%, 30%, 35%, 40%, 45%, 50%, 55%, 60%, 65%, 70%, 80%, 90%, 95%, or even 100% decrease) in the amount of labeled ADP-ribose covalently attached to one or more (e.g., 1, 2, 3, 4, 5, 6, 7, 8, 9, 10, 11, 12, 13, 14, 15, 16, 17, 18, 19, or 20) PARP fusion proteins, wherein the label on the PARP-fusion proteins is the same as the label of the $NAD^+$. In a method for identifying an agent that is a specific PARP activator, the agent mediates an increase (e.g., at least a 5%, 10%, 15%, 20%, 25%, 30%, 35%, 40%, 45%, 50%, 55%, 60%, 65%, 70%, 80%, 90%, 95%, or even 100% increase) in the amount of labeled ADP-ribose covalently attached to one or more (e.g., 1, 2, 3, 4, 5, 6, 7, 8, 9, 10, 11, 12, 13, 14, 15, 16, 17, 18, 19, or 20) PARP fusion proteins.

The one or more PARP fusion proteins utilized in each assay may be purified, partially purified (e.g., at least 30% pure, at least 40% pure, at least 50% pure, at least 60% pure, at least 70% pure, at least 80% pure, at least 85% pure) or may be present in a cell lysate (e.g., a bacterial cell lysate, a yeast cell lysate, or a mammalian cell lysate), in a biological fluid from a transgenic animal (e.g., milk or serum), or an extracellular medium. The one or more PARP fusion proteins utilized in the assay may be bound to substrate, such as, but not limited to, a solid surface (e.g., a multi-well plate), a resin, or a bead (e.g., a magnetic bead).

In additional examples of the assays, the one or more PARP fusion proteins may be bound to a solid surface, resin, or bead (e.g., a magnetic bead) and subsequently treated with one or more protease(s) (e.g., a TEV protease) prior to contacting the one or more PARP fusion proteins with the labeled $NAD^+$.

In preferred assays, an activator or inhibitor increases or decreases the amount of labeled ADP-ribose covalently attached to a specific PARP fusion protein or subset of PARP fusion proteins while having no or little (e.g., less than 50%, less than 40%, less than 30%, less than 25%, less than 20%, less than 15%, less than 10%, or less than 5% change (e.g., increase or decrease)) affect on the amount of labeled ADP-ribose covalently attached to other PARP fusion proteins, is identified as a PARP activator or inhibitor, respectively. For example, the assay desirably identifies an agent that specifically inhibits the amount of labeled ADP-ribose covalently attached to one or more (e.g., 1, 2, 3, 4, 5, 6, 7, 8, 9, or 10) PARP5A fusion proteins, PARP12 fusion proteins, PARP13.1 fusion proteins, PARP13.2 fusion proteins, and PARP15 fusion proteins. Another assay desirably identifies an agent that specifically increases the amount of labeled ADP-ribose covalently attached to one or more (e.g., 1, 2, 3, 4, 5, 6, 7, 8, 9, or 10) PARP5A fusion proteins, PARP12 fusion proteins, PARP13.1 fusion proteins, PARP13.2 fusion proteins, and PARP15 fusion proteins. Another example of the assay desirable identifies an activator or inhibitor that specifically increases or decreases, respectfully, the amount of labeled ADP-ribose covalently bound to one or more (e.g., 1, 2, 3, 4, 5, or 6) PARP11 fusion proteins. Another example of the assay desirably identifies an agent that specifically decreases the amount of labeled ADP-ribose covalently attached to one or more (e.g., 1, 2, 3, 4, 5, 6, 7, 8, 9, or 10) PARP1 fusion proteins, PARP2 fusion proteins, PARP5A fusion proteins, PARP5B fusion proteins, PARP7 fusion proteins, PARP8 fusion proteins, PARP14 fusion proteins, and PARP16 fusion proteins. Another example of the assay desirably identifies an agent that specifically increases the amount of labeled ADP-ribose covalently attached to one or more (e.g., 1, 2, 3, 4, 5, 6, 7, 8, 9, or 10) PARP1 fusion proteins, PARP2 fusion proteins, PARP5A fusion proteins, PARP5B fusion proteins, PARP7 fusion proteins, PARP8 fusion proteins, PARP14 fusion proteins, and PARP16 fusion proteins. In another desirable embodiment of the assay, the assay identifies an agent that specifically increases or decreases the amount of labeled ADP-ribose covalently attached to one or more (e.g., 1, 2, 3, 4, 5, or 6) different PARP13.1 fusion proteins.

A variety of different agents may be tested in the above-described assays provided by the invention. For example, a tested agent may be a derived from or present in a crude lysate (e.g., a lysate from a mammalian cell or plant extract) or be derived from a commercially available chemical libraries. Large libraries of natural product or synthetic (or semi-synthetic) extracts or chemical libraries are commercially available and known in the art. The screening methods of the present invention are appropriate and useful for testing agents from a variety of sources for activity as a specific PARP activator or inhibitor. The initial screens may be performed using a diverse library of agents, but the method is suitable for a variety of other compounds and compound libraries. Such compound libraries can also be combinatorial libraries. In addition, compounds from commercial sources can be tested, as well as commercially available analogs of identified inhibitors.

An agent may be a protein, a peptide, a DNA or RNA aptamer (e.g., a RNAi molecule), a lipid, or a small molecule (e.g., a lipid, carbohydrate, a bioinorganic molecule, or an organic molecule).

Agents that may be tested as a specific PARP activator include nucleic acids that contain a sequence encoding one or more (e.g., 1, 2, 3, 4, 5, 6, 7, 8, 9, or 10) domains of a PARP protein (e.g., a domain encoded by part of the nucleic acid sequence having at least 80% sequence identity to any one of SEQ ID NOS: 1-24).

Methods for Identification of an Agent that Specifically Binds One or More PARPs The invention also provides methods for identifying an agent that specifically binds to one or more (e.g., 1, 2, 3, 4, 5, 6, 7, 8, 9, 10, 11, 12, 13, 14, 15, 16, 17, 18, 19, or 20 or more) PARP proteins or PARP fusion proteins. These methods require the contacting of one or more of the PARP fusion proteins of the invention with a test agent and determining whether the test agent specifically binds to the one or more PARP fusion proteins. An agent that specifically binds one or more of the described PARP fusion proteins may act as an activator or inhibitor of the expression or activity of the one or more PARP fusion proteins or PARP proteins in a cell. For example, an agent that specifically binds to one or more PARP fusion proteins may selectively increase the activity or expression of one or more PARP fusion proteins, while at the same time decreasing the activity or expression of one or more other PARP fusion proteins in the same cell or sample.

The one or more PARP fusion proteins used in this method may be attached to a solid surface or substrate (e.g., a bead) and/or may be present in purified form or present in a crude cell lysate, biological fluid, or extracellular medium. The methods may optionally include one or more (e.g., 1, 2, 3, 4, or 5) washing steps following contacting the one or more PARP fusion proteins with the test agent. The test agent may be a small molecule, a lipid, an RNA molecule, a DNA molecule, a protein, or a peptide fragment. The test agent may be purified in form (e.g., at least 70% pure by weight, 80% pure by weight, 85% pure by weight, 90% pure by weight, 95% pure by weight, or 99% pure by weight) or may be present in a crude cell lysate. The test agent may also, optionally be labeled (e.g., a colorimetric label, a radionuclide label, labeled with a biotin molecule, or labeled with a fluorophore).

The binding of the test agent to one of more PARP fusion proteins may detected by any known method including, BIAcore, competitive binding assays (e.g., a competitive binding assay using one or more of the antibodies provided by the invention), and detection of the agent following its release from the one or more PARP fusion proteins (e.g., elution of the bound test agent following exposure to high salt or a high or low pH buffer). The one or more PARP fusion proteins may be any of the example PARP fusion proteins described herein.

In one example of this method, a bead attached to one or more PARP fusion proteins of the invention (e.g., a ZZ-TEV-PARP fusion protein) may be incubated with a crude cell lysate, and the proteins or peptide fragments bound to the one or more PARP fusion proteins may be eluted from the beads by exposure to a high salt buffer, a high detergent buffer, or a high or low pH buffer. The resulting eluted proteins may be electrophoresed onto an SDS-polyacrylamide gel and the specific protein bands cut out from the gel and analyzed using mass spectrometry to identify the specific agent that binds to the one or more PARP fusion proteins.

In another example of the method, a bead attached to one or more PARP fusion proteins of the invention is incubated with a purified protein or peptide fragment. In this instance, a protein or peptide fragment bound to the one or more PARP fusion proteins may be eluted using a high salt buffer, a high detergent buffer, or a high or low pH buffer. The amount of protein in the eluate may be detected by any method known in the art including UV/vis spectroscopy, mass spectrometry, or any colorimetric protein dye (e.g., a Bradford assay).

In specific screening assays for agents that bind one or more PARP fusion proteins, one or more PARP fusion proteins may be placed in individual wells of a multi-well plate (e.g., one or more PARP fusion proteins covalently linked to the plate surface) and incubated with the test agent. Following a washing step, the amount of test agent remaining in each well may be determined and the ability of the test agent to bind one or more PARP fusion protein determined.

The methods desirably identify a test agent that specifically binds one or more of a PARP1 fusion protein, a PARP2 fusion protein, a PARP5A fusion protein, a PARP5B fusion protein, a PARP7 fusion protein, a PARP8 fusion protein, a PARP14 fusion protein, and a PARP16 fusion protein of the invention. The methods also desirably identify a test agent that specifically binds to one or more of a PARP5A fusion protein, a PARP12 fusion protein, a PARP13.1 fusion protein, a PARP13.2 fusion protein, and a PARP15 fusion protein of the invention. The methods also desirably identify a test agent that specifically binds to a PARP13.1 fusion protein or a PARP11 fusion protein of the invention.

Methods for Quantification of the Level of One or More PARPs in a Sample

The present invention further provides methods for quantitating the level of one or more PARP proteins or PARP fusion proteins present in a sample (e.g., a cell, a cell lysate, a biological fluid, or an extracellular medium). In these methods, a cell, cell lysate, biological fluid, or extracellular medium is contacted with one or more (e.g., 1, 2, 3, 4, 5, 6, 7, 8, 9, or 10) antibodies of the invention (e.g., antibodies that specifically bind to one or more PARP fusion proteins described herein) and the level of one or more PARP proteins or fusion proteins is determined by measuring the amount of the one or more PARP proteins or PARP fusion proteins bound to the one or more antibodies.

In these methods, the one or more antibodies may be polyclonal antibodies. The antibodies used in these methods may also be covalently bound to a bead (e.g., a magnetic bead or a bead in a column) or may be covalently bound to the surface of a multi-well plate (e.g., for use in an enzyme-linked immunosorbent assay (ELISA)). The quantitation of the binding of the one or more antibodies to the one or more PARP proteins or PARP fusion proteins may be determined by any method known in the art, including, but not limited to, BIAcore, immunofluorescence microscopy, immunofluorescence-assisted cell sorting, ELISA, immunoblotting, and competitive binding assays (e.g., assays using purified labeled PARP proteins or PARP fusion proteins).

In these assays, the level of one or more PARP proteins or PARP fusion proteins may be compared to a standard curve control generated using one or more purified PARP proteins or PARP fusion proteins as described herein. The level of one or more PARP proteins present in a cell, cell lysate, or biological sample may be used as an indicator of the status or severity of one or more stress granule-related condition (e.g., a neurodegenerative disease, a cardiovascular disease, an inflammatory disease, and ischemia-reperfusion injury). For example, an increase in the level of one or more of PARP5A, PARP12, PARP13.1, PARP13.2, and PARP15 indicates an increased severity or an increase in the likelihood of developing a stress granule related disorder.

Kits

Also provided are kits containing one or more (e.g., 1, 2, 3, 4, 5, 6, 7, 8, 9, 10, 11, 12, 13, 14, 15, 16, 17, 18, 19, or 20 or more) of the above-described PARP fusion proteins (or nucleic acids encoding the PARP fusion proteins), antibodies, cell lysates, and/or transgenic cells of the invention. For example, a kit may contain one or more (e.g., 1, 2, 3, 4, 5, 6, 7, 8, 9, 10, 11, 12, 13, 14, 15, 16, 17, 18, 19, or 20 or more) purified PARP-fusion proteins, cell lysates, and/or transgenic cells of the invention and, optionally, a labeled $NAD^+$. Another example of a kit contains a cell expressing one or more (e.g., 1, 2, 3, 4, 5, 6, 7, 8, 9, 10, 11, 12, 13, 14, 15, 16, 17, 18, 19, or 20 or more) PARP fusion proteins of the invention and instructions for the culture of the cell and/or the preparation of lysate from the cell, and optionally, a labeled $NAD^+$.

EXAMPLES

The features and other details of the invention will now be more particularly described and pointed out in the following examples describing preferred techniques and experimental results. These examples are provided for the purpose of illustrating the invention and should not be construed as limiting.

Example 1

Generation of PARP-GFP Fusion Proteins and Assays

Figure 4:
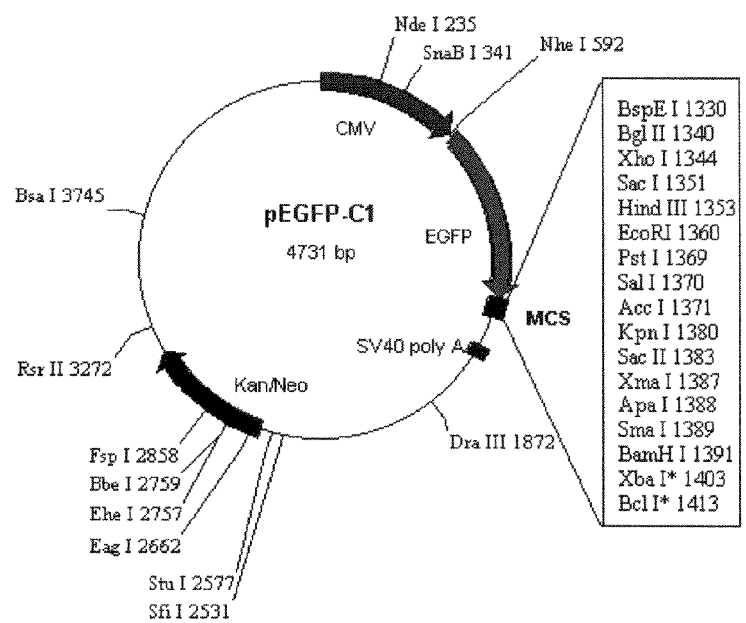
FIG. 4 is a diagram of the pEGFP-C1 vector (SEQ ID NO: 28) (Invitrogen) showing the CMV promoter, the EGFP sequence, the multiple cloning site (MCS), and the SV40 poly A sequence. Also shown is the polylinker sequence (SEQ ID NO: 29).

Fusion proteins containing the sequence of each PARP and green fluorescent protein (GFP) were generated using the pEGFP-C1 vector (Invitrogen) (FIG. 4). For these experiments, the DNA sequences encoding each of PARP1 (SEQ ID NOS: 1 and 2), PARP3 (SEQ ID NOS: 4, 5, and 6), PARP4 (SEQ ID NO: 7), PARP5A (SEQ ID NOS: 8 and 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NOS: 15 and 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15 (SEQ ID NOS: 22 and 23), and PARP16 (SEQ ID NO: 24) were cloned into the pEGFP-C1 vector using the restriction sites indicated in Table 1. Each resulting plasmid contained a nucleic acid sequence encoding a PARP-GFP fusion protein, wherein the nucleic acid sequence encoding GFP was located 5' to the nucleic acid sequence encoding the PARP protein.

TABLE 1

Restriction Sites Used for Cloning PARP Sequences into pEGFP-C1

| PARP | Restriction Sites |
|---|---|
| 1 | BglII, SalI |
| 3 | BglII, SalI |
| 4 | KpnI, ApaI |
| 5a | HinDIII, BglII |
| 5b | SalI, BamHI |
| 6 | SalI, XmaI |
| 7 | BspEI, EcoRI |
| 8 | BspEI, SalI |
| 9 | BspEI, SalI |
| 10 | BamHI, BglII |
| 11 | SalI, BamHI |
| 12 | SalI, ApaI |
| 13 isoform 1 | BspEI, BamHI |
| 13 isoform 2 | BglII, BamHI |
| 14 | XhoI, SacII |
| 15 | SalI, BamHI |
| 16 | BglII, SalI |

Figure 5:
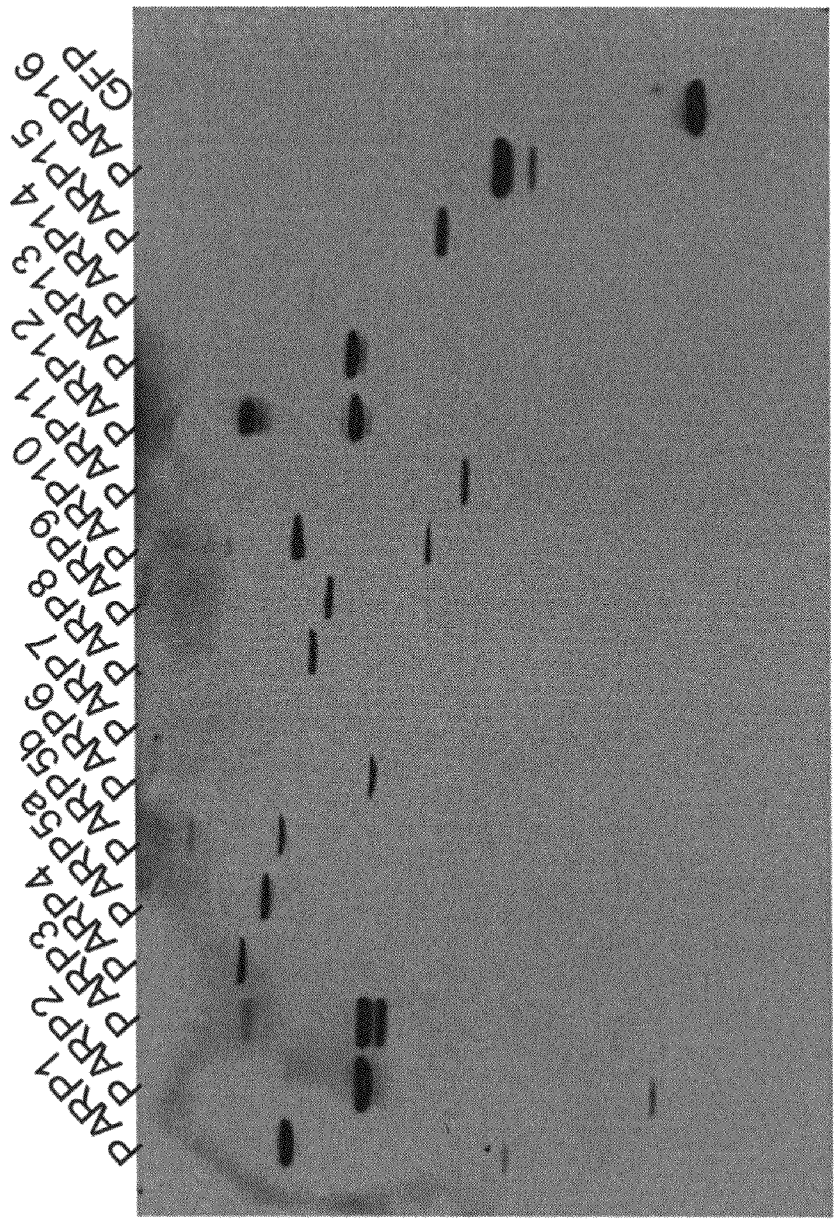
FIG. 5 is an immunoblot showing the expression and relative size of the PARP-GFP fusion proteins of PARP1, PARP2, PARP3, PARP4, PARP5A, PARP5B, PARP6, PARP7, PARP8, PARP9, PARP10, PARP11, PARP12, PARP13, PARP14, PARP15, and PARP16 expressed in HeLa Kyoto cells transfected with pEGFP-C1 plasmids containing a nucleic acid encoding each respective PARP-GFP fusion protein. The immunoblot was developed using a rabbit anti-GFP polyclonal antibody.

Each generated pEGFP-C1 vector was transfected into HeLa Kyoto cells using Lipofectamine 2000, according to the manufacturer's instructions. Cell lysate was prepared from the HeLa cells at 48 hours following transfection. Electrophoresis was performed on the cell lysate using 4-12% SDS- PAGE, and immunoblotting was performed using a rabbit anti-GFP polyclonal antibody (FIG. 5).

Figure 6:
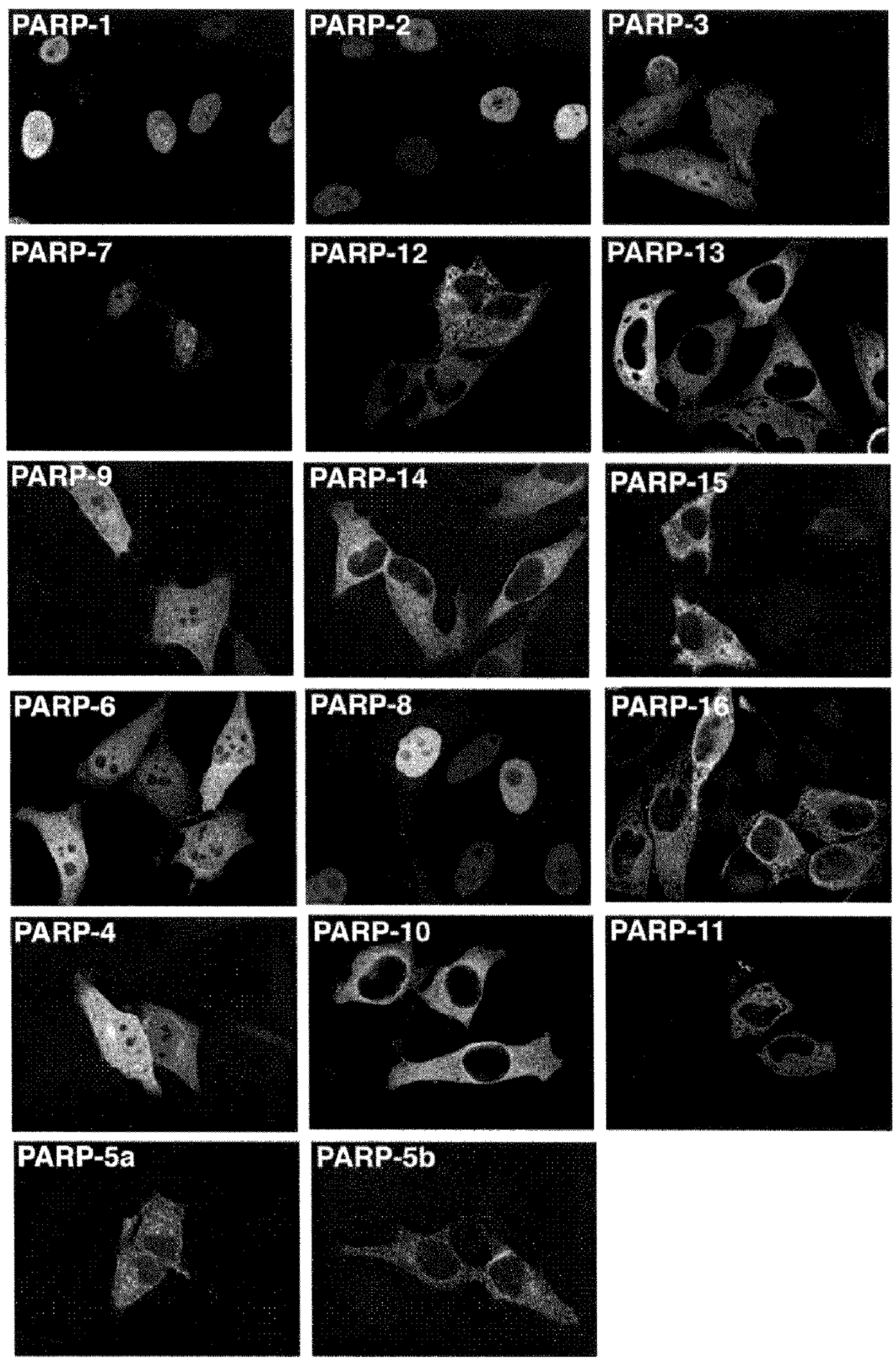
FIG. 6 is a set of micrographs showing the localization of different PARP-GFP fusion proteins in asynchronous HeLa Kyoto cells transfected with a pEGFP-C1 plasmid containing a nucleic acid encoding a PARP-GFP protein. The transfected cells were immunostained with rabbit anti-GFP polyclonal antibody and fluorescently-labeled secondary Alexa Fluor 594 or 488 antibody (Invitrogen), and visualized using fluorescence microscopy. The localization of PARP1-GFP, PARP2-GFP, PARP3-GFP, PARP7-GFP, PARP12-GFP, PARP13-GFP, PARP9-GFP, PARP14-GFP, PARP15-GFP, PARP6-GFP, PARP8-GFP, PARP16-GFP, PARP4-GFP, PARP10-GFP, PARP11-GFP, PARP5A-GFP, and PARP5B-GFP fusion proteins is shown.
Figure 7:
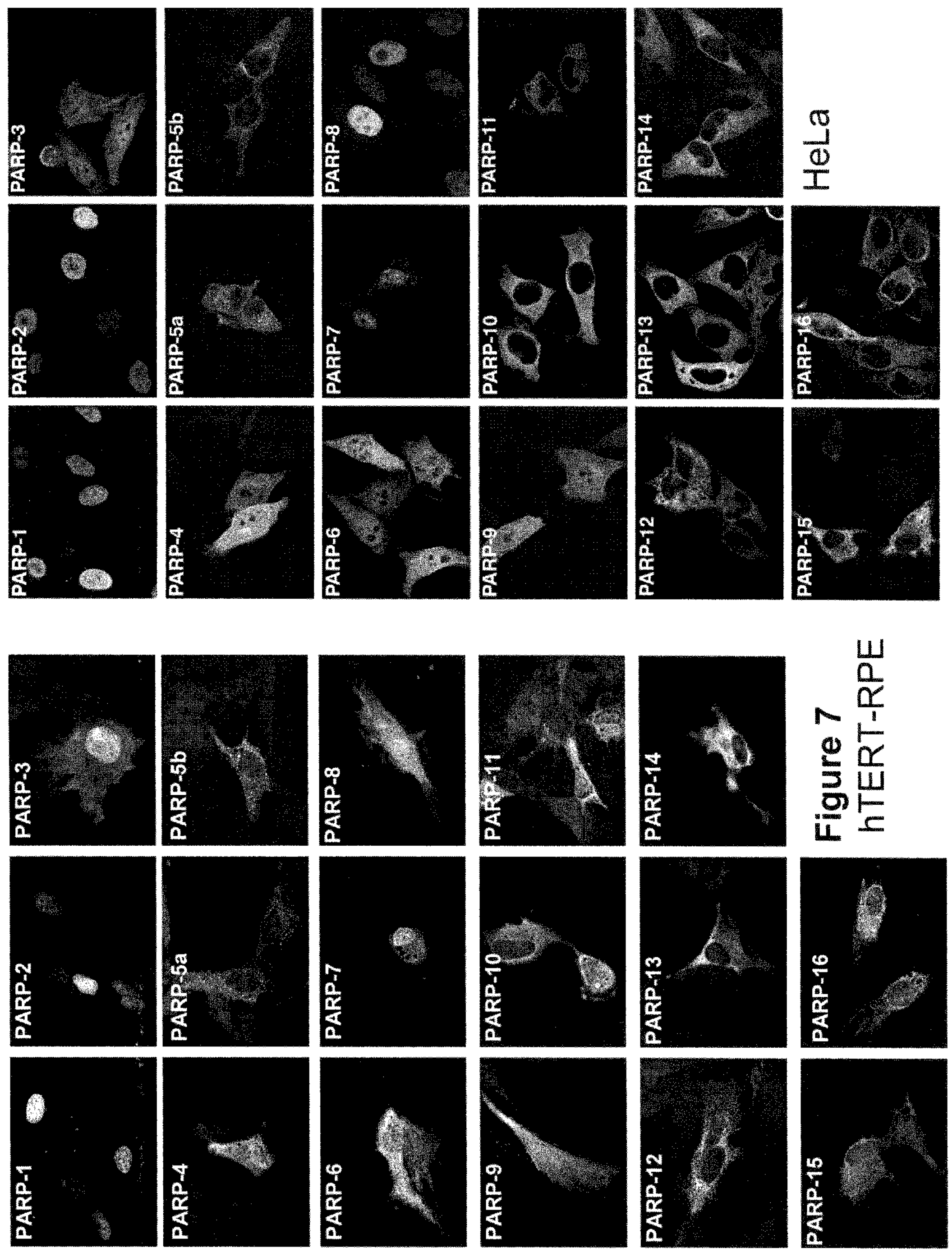
FIG. 7 is two sets of micrographs showing the localization of different PARP-GFP fusion proteins in asynchronous hTERT-RPE and HeLa Kyoto cells transfected with a pEGFP-C1 plasmid containing a nucleic acid encoding a PARP-GFP protein. The transfected cells were immunostained with rabbit anti-GFP polyclonal antibody and fluorescently-labeled Alexa Fluor 594 or 488 antibodies (Invitrogen), and visualized using fluorescence microscopy. The localization of PARP1-GFP, PARP2-GFP, PARP3-GFP, PARP4-GFP, PARP5A-GFP, PARP5B-GFP, PARP6-GFP, PARP7-GFP, PARP8-GFP, PARP9-GFP, PARP10-GFP, PARP11-GFP, PARP12-GFP, PARP13-GFP, PARP14-GFP, PARP15-GFP, and PARP16-GFP fusion proteins is shown for each cell type.

The localization of each PARP-GFP fusion protein in the transfected HeLa Kyoto cells was determined using immunofluorescence microscopy using rabbit anti-GFP polyclonal antibody and a fluorescently-labeled secondary antibody (FIG. 6). The data from this experiment indicate that several PARP-GFP proteins are primarily localized in the nucleus of asynchronous cells, including PARP1-GFP, PARP2-GFP, PARP7-GFP, and PARP8-GFP. The data further indicate that several PARP-GFP fusion proteins are localized in primarily in the cytoplasm of asynchronous cells, including PARP12-GFP, PARP13-GFP, PARP14-GFP, PARP15-GFP, PARP16-GFP, PARP10-GFP, PARP11-GFP, PARP5A-GFP, and PARP5B-GFP. In addition, the data indicate that several PARP-GFP fusion proteins are localized in both the cytoplasm and the nucleus of asynchronous cells, including PARP3-GFP, PARP9-GFP, PARP6-GFP, and PARP4-GFP. The same pattern of cell localization for each PARP-GFP fusion protein was observed in the hTERT-RPE1 cell line (Clontech), a telomerase-immortalized human retinal pigment epithelial (RPE) normal cell line (FIG. 7).

Antibodies specific for each PARP were generated by immunizing rabbits with PARP-specific peptides conjugated to keyhole limpet hemocyanin (KLH) using known methods. The antibodies produced in the rabbit serum were later affinity purified using peptide columns (e.g., columns containing, as substrate, the specific peptide sequence used to inoculate the rabbit).

Figure 8:
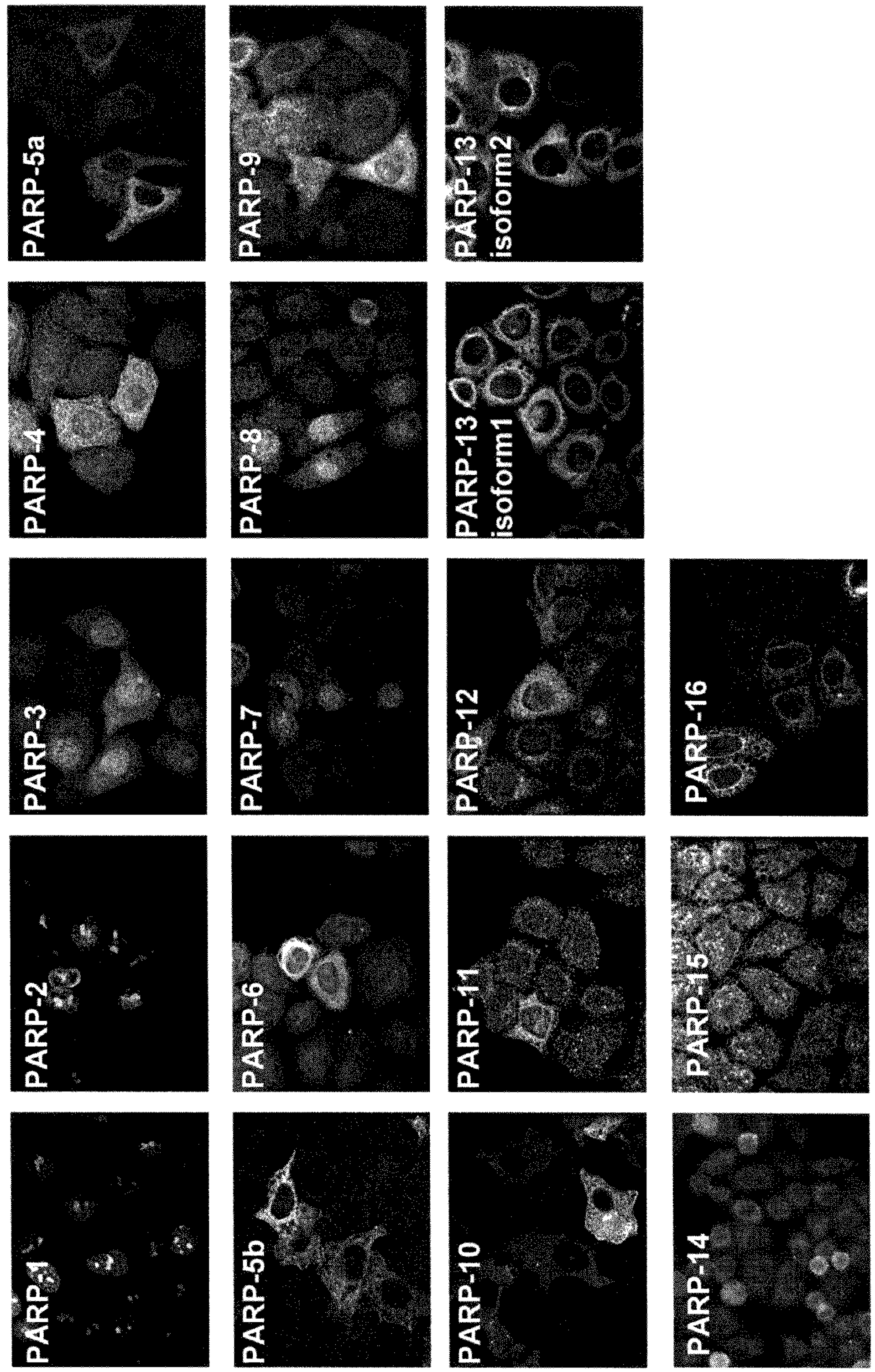
FIG. 8 is a set of micrographs from asynchronous HeLa Kyoto cells transfected with a pEGFP-C1 plasmid containing a nucleic acid encoding a PARP-GFP protein following immunostaining with primary rabbit antibodies raised against each specific PARP and fluorescently-labeled Alexa Fluor 594 or 488 antibodies (Invitrogen). The localization of PARP1, PARP2, PARP3, PARP4, PARP5A, PARP5B, PARP6, PARP7, PARP8, PARP9, PARP10, PARP11, PARP12, PARP13.1, PARP13.2, PARP14, PARP15, and PARP16 is shown.

The antibodies for each PARP and a secondary-fluorescently labeled anti-rabbit polyclonal antibody were used to visualize the location of each PARP in asynchronous HeLa Kyoto cells transfected with a pEGFP-C1 plasmid encoding a PARP-GFP fusion protein (FIG. 8). The data from this experiment confirm that PARP1, PARP2, PARP7, PARP8, and PARP14 are primarily localized in the nucleus of asynchronous cells. The data from this experiment also confirm that PARP3, PARP4, PARP6, PARP9, and PARP15 are localized in the both the nucleus and the cytoplasm of asynchronous cells.

Figure 9:
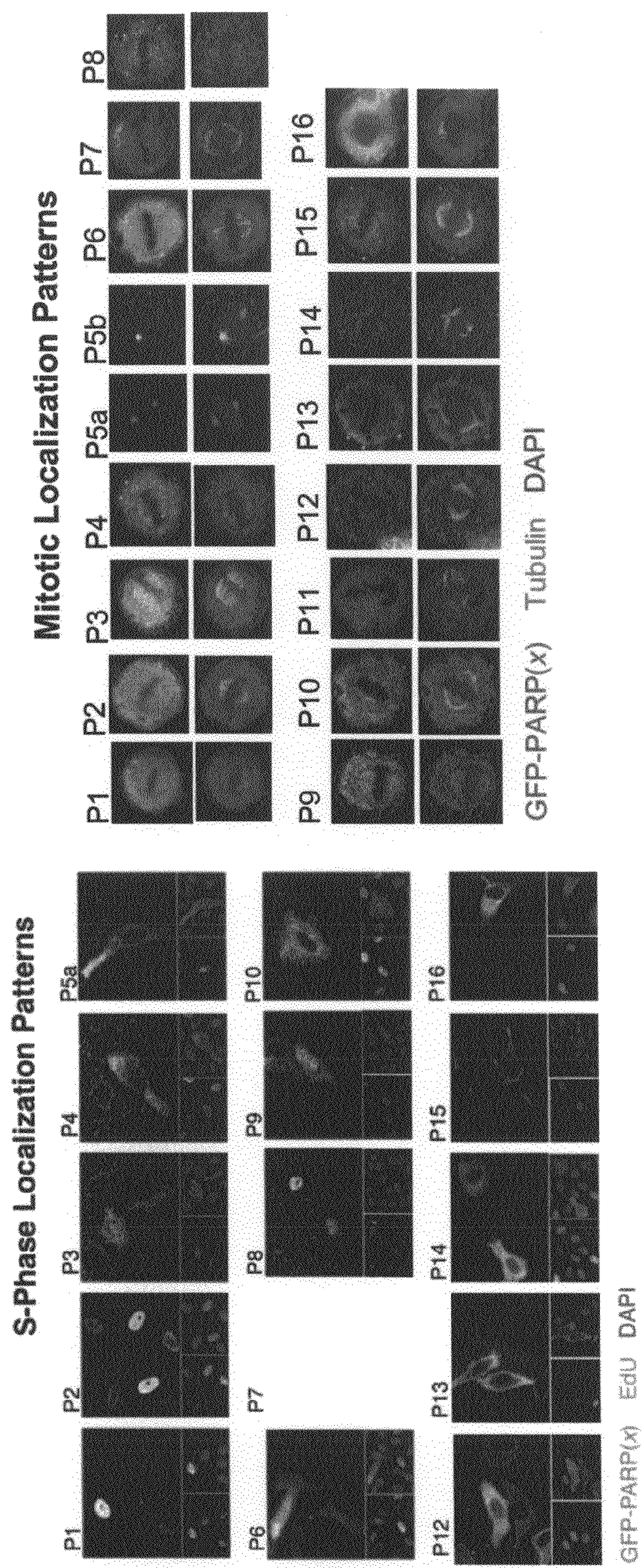
FIG. 9 is a set of micrographs showing the localization of each PARP-GFP fusion protein during S-phase and mitosis in transfected HeLa Kyoto cells. In each experiment, HeLa Kyoto cells were transfected using Lipofectamine 2000 with a specific PARP-GFP expression vector (pEGFP-C1) and were arrested in mitosis or S-phase by treatment with 100 nM nocodazole or 5 μg/mL aphidicolin for 12 hours. The resulting treated cells were immunostained with rabbit anti-GFP polyclonal antibodies and fluorescently-labeled Alexa Fluor 594 or 488 antibodies (Invitrogen), and visualized using fluorescence microscopy. S-phase-arrested cells were also stained with EdU and DAPI, and mitosis-arrested cells were further stained with tubulin and DAPI.

The localization of each PARP-GFP fusion protein (described above) was also determined in HeLa Kyoto cells transfected with a pEGFP-C1 plasmid encoding a PARP-GFP fusion protein following 12-hour treatment with 100 nM nocodazole or 5 μg/mL aphidicolin. Cells treated with nocodazole are arrested in S phase, while cells treated with aphidicolin are arrested in mitotosis. FIG. 9 shows the cellular localization for each PARP-GFP fusion protein following cell arrest in S-phase or mitosis. The data show that the PARP1-GFP, PARP2-GFP, and PARP8-GFP fusion proteins localize to the nucleus during S-phase, and that PARP5A-GFP and PARP5B-GFP localize to the mitotic spindle during mitosis. The localization of these PARP-GFP fusion proteins (e.g., PARP1-GFP, PARP2-GFP, PARP5A-GFP, PARP5B-GFP, and PARP8-GFP) to the nucleus during S-phase and mitosis indicate a role for these PARP proteins in cell division and cell proliferation.

Figure 10:
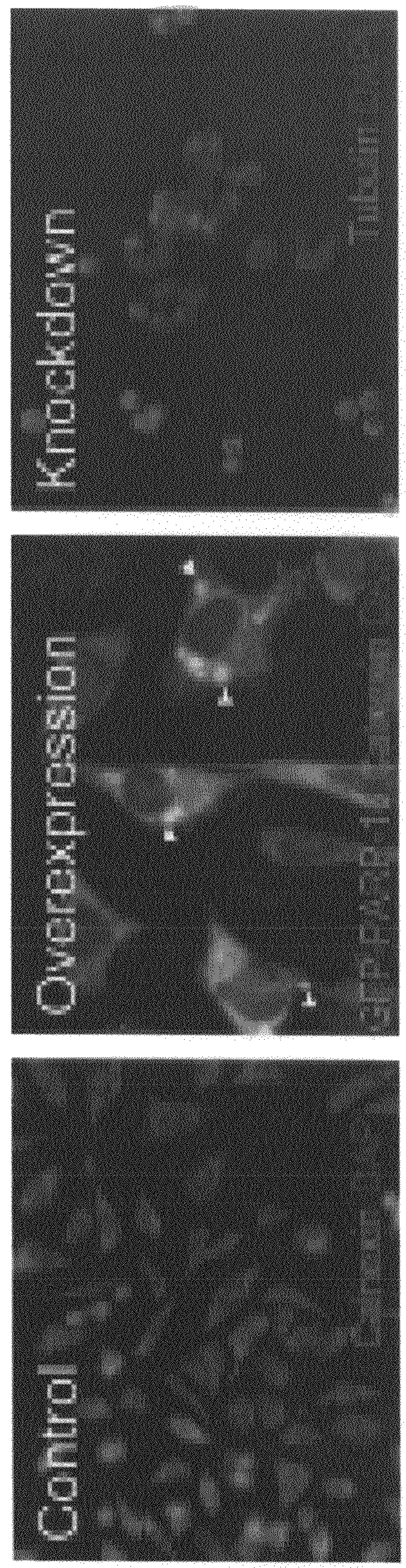
FIG. 10 is a set of micrographs showing the localization of overexpressed PARP16-GFP in the endoplasmic reticulum of HeLa Kyoto cells transfected with a pEGFP-C1 plasmid encoding a PARP16-GFP fusion protein (middle panel) and the phenotype of HeLa Kyoto cells transfected with an RNAi targeting endogenous PARP16 (right panel). The left panel shows untransfected HeLa Kyoto cells stained with anti-calnexin antibodies, secondary fluorescently-labeled antibodies (Alexa Fluor 594 or 488 antibodies (Invitrogen)), and DAPI. The middle panel the localization of PARP16-GFP and calnexin in HeLa Kyoto cells transfected with a pEGFP-C1 plasmid expressing a PARP16-GFP fusion protein following staining with anti-calnexin, anti-GFP, Alexa Fluor 594 or 488 antibodies (Invitrogen), and DAPI. The right panel shows the phenotype of HeLa Kyoto cells following transfection with an RNAi molecule targeting endogenous PARP16 (SEQ ID NO: 43) following staining with an anti-tubulin antibody, Alexa Fluor 594 or 488 antibody (Invitrogen), and DAPI.

In order to study the role of PARP16, additional experiments were performed using RNAi knockdown of endogenous PARP16 or overexpression of PAPR16-GFP fusion proteins to study the effect of PARP16 knockdown and overexpression, respectively on cell morphology. Asynchronous HeLa Kyoto cells overexpressing PARP16-GFP protein had normal cell morphology (FIG. 10; middle panel). In these cells, the PARP16-GFP protein was primarily localized in the endoplasmic reticulum, as demonstrated by its co-localization with calnexin (FIG. 10; middle panel). HeLa Kyoto cells transfected with an RNAi molecule specific for PARP16 demonstrated significant morphological changes, including cell shrinkage and dramatic membrane defects (FIG. 10; right panel).

Figure 11:
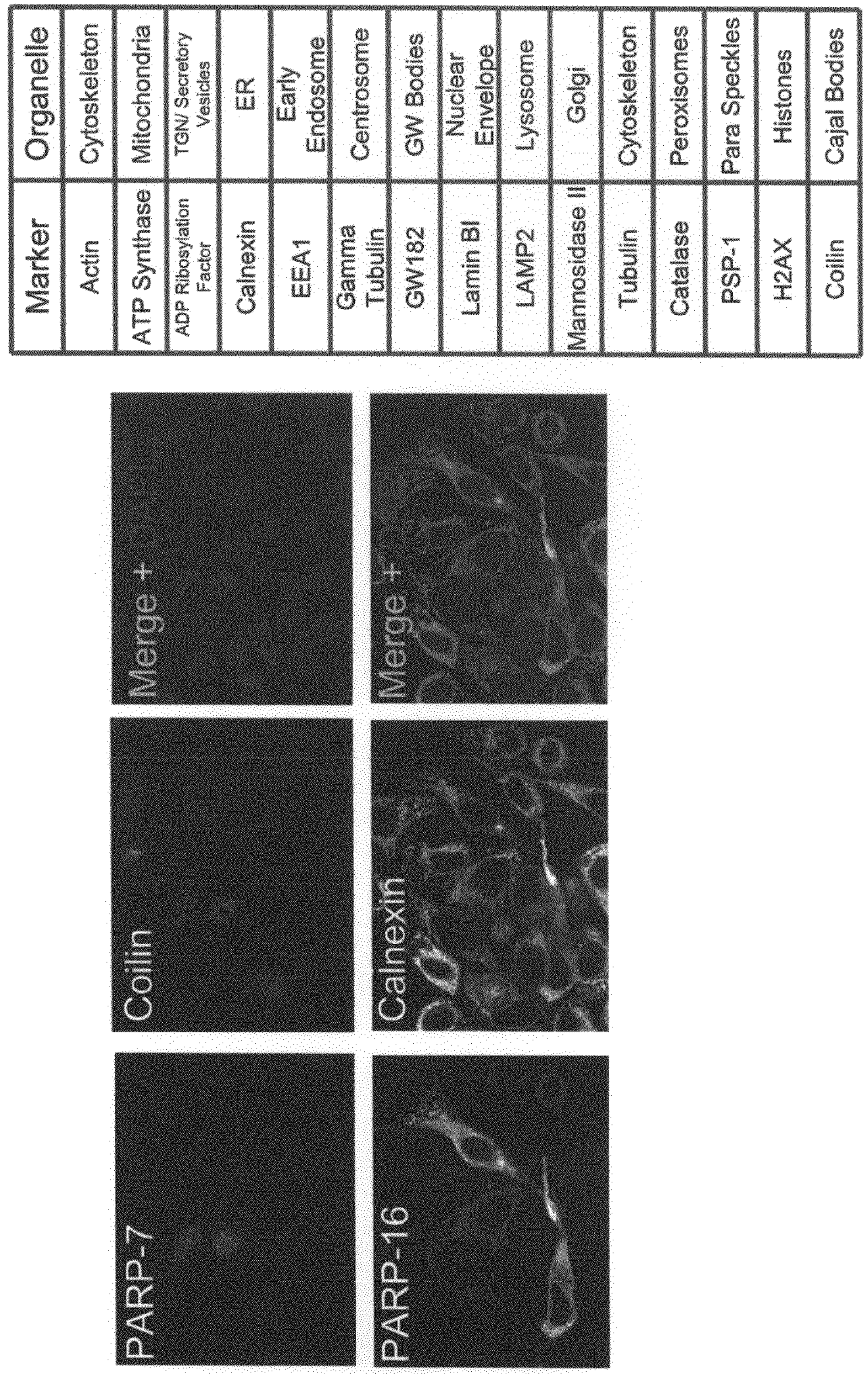
FIG. 11 is a set of micrographs showing the co-localization of PARP7-GFP and coilin, and the co-localization of PARP16-GFP and calnexin. In each experiment, HeLa Kyoto cells transfected with pEGFP-C1 vectors expressing PARP7-GFP or PARP16-GFP were stained with anti-GFP and anti-coilin or anti-calnexin antibodies, and fluorescently labeled secondary antibodies (Alexa Fluor 594 or 488 antibodies). The figure also lists a number of protein markers of specific cellular organelles and structures.

The specific cellular localization of each PARP-GFP fusion protein may be further analyzed by immunofluorescence microscopy using a combination of labeled antibodies specific for the GFP-tag of each PARP-GFP fusion protein and one or more markers of cellular structures or organelles. For example, immunofluorescence staining of asynchronous HeLa Kyoto cells transfected with a pEGFP-C1 vector expressing the PARP7-GFP fusion protein shows co-localization of an anti-GFP antibody and an anti-coilin antibody (a marker of Cajal bodies in the nucleus) (FIG. 11). In another example, asynchronous HeLa Kyoto cells transfected with a pEGFP-C1 vector expressing the PARP16-GFP fusion protein shows co-localization of an anti-GFP antibody and an anti-calnexin antibody (a marker of the endoplasmic reticulum) (FIG. 10). A non-limiting list of marker proteins that may be used to determine the cellular localization of a PARP-GFP fusion protein is also provided in FIG. 11.

Experimental Methods

Kyoto HeLa cells were grown in DMEM supplemented with 10% FCS and penicillin/streptomycin at 37° C. in 5% $CO_2$. Lipofectamine 2000 (Invitrogen) was used to transfect the cells with each pEGFP-C1 vector according to the manufacturer's protocol. Cells were arrested in mitosis and S-phase by treatment with 100 nM nocodazole or 5 μg/mL aphidicolin for 12 hours, respectively. For immunofluorescence imaging, cells on coverslips were fixed in ice-cold methanol for five minutes and rehydrated in phosphate buffered saline (PBS). The cells were blocked in PBS containing 4% bovine serum albumin (BSA) and 0.1% Triton-X 100. All antibodies used for imaging were diluted in blocking buffer. The coverslips were incubated with primary antibodies for 45 minutes and with secondary antibodies for 30 minutes. Images were collected on a Nikon TE2000 confocal microscope equipped with a Yokogawa CSU-X1 spinning disk head, Hamamatsu ORCA ER digital camera, and NIS-Elements imaging software.

Example 2

Generation of ZZ-TEV-PARP Fusion Proteins

Figure 12:
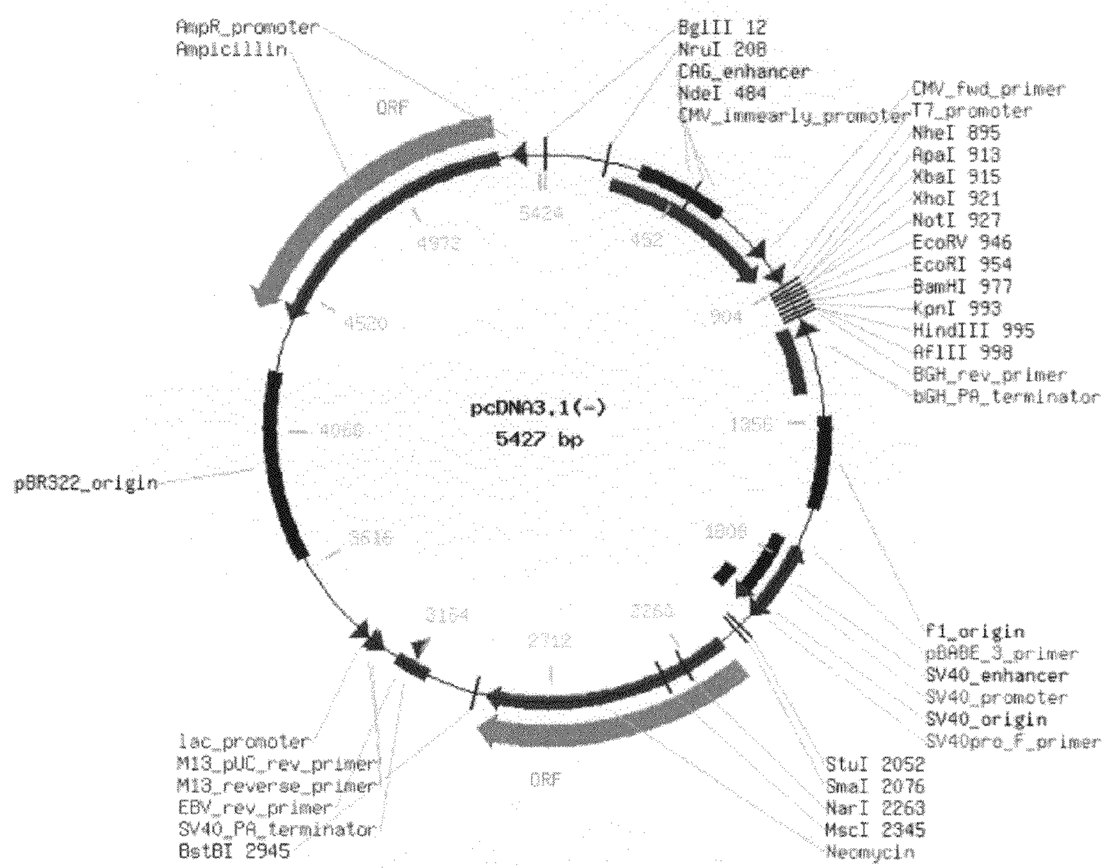
FIG. 12 is a diagram of the pcDNA3.1 vector (Invitrogen) showing the CMV promoter and the restriction sites that may be used for cloning.

Fusion proteins containing the sequence of each PARP, a ZZ-domain of SEQ ID NO: 27, and four TEV protease recognition sequences (SEQ ID NO: 26) were cloned using the pcDNA3.1 vector (SEQ ID NO: 33) (Invitrogen) (FIG. 12) to yield a ZZ-4x-TEV-PARP fusion protein for each PARP. For these experiments, the DNA sequences encoding PARP1 (SEQ ID NOS: 1 and 2), PARP2 (SEQ ID NO: 3), PARP3 (SEQ ID NOS: 4, 5, and 6), PARP4 (SEQ ID NO: 7), PARP5A (SEQ ID NOS: 8 and 9), PARP6 (SEQ ID NO: 11), PARP7 (SEQ ID NO: 12), PARP9 (SEQ ID NO: 14), PARP10 (SEQ ID NOS: 15 and 16), PARP11 (SEQ ID NO: 17), PARP13.1 (SEQ ID NO: 19), PARP13.2 (SEQ ID NO: 20), PARP14 (SEQ ID NO: 21), PARP15 (SEQ ID NOS: 22 and 23), and PARP16 (SEQ ID NO: 24) were cloned into the pcDNA3.1 vector using the restriction sites indicated in Table 2. The sequence encoding the ZZ-domain and the sequence encoding the four TEV protease recognition sequences were cloned into the NheI and HinDIII restriction sites in pcDNA3.1.

TABLE 2

| Restriction Sites Used for Cloning PARP Sequences into pcDNA3.1 | |
|---|---|
| PARP | Restriction Sites |
| 1 | XhoI, PmeI |
| 2 | BamHI, NotI |
| 3 | EcoRV, NotI |
| 4 | KpnI, ApaI |
| 5a | HinDIII, XhoI |
| 6 | EcoRV, NotI |
| 7 | BamHI, NotI |
| 9 | EcoRV, NotI |
| 10 | HinDIII, XbaI |
| 11 | BamHI, XbaI |
| 13 isoform 1 | KpnI, BamHI |
| 13 isoform 2 | BamHI, EcoRV |
| 14 | KpnI, XhoI |
| 15 | KpnI, XhoI |
| 16 | KpnI, XbaI |

Each resulting plasmid contained a nucleic acid sequence encoding a ZZ-TEV-PARP fusion protein, wherein the nucleic acid sequence encoding ZZ domain was located 5' to the nucleic acid sequence encoding the four TEV protease recognition sequences, which in turn, was located 5' to the nucleic acid sequence encoding each PARP.

Nucleic acids encoding each ZZ-TEV-PARP fusion protein may be transfected into target cells (e.g., HeLa Kyoto or HeLa S3 cells) and the resulting ZZ-TEV-PARP fusion proteins purified by binding to magnetic beads coated with a protein containing an Fc domain (e.g., IgG). The resulting ZZ-TEV-PARP fusion proteins may be used in the assays described below for the PARP-GFP fusion proteins and the other assays described herein. Assays utilizing the ZZ-TEV-PARP fusion proteins have the additional advantage of containing an engineered TEV protease recognition sequence, whereby the polypeptide tag on each PARP fusion protein (e.g., the ZZ-domain and the four TEV protease recognition sequences) may optionally be removed from the ZZ-TEV-PARP fusion proteins by treatment with TEV protease. In one example, one or more ZZ-TEV-PARP fusion proteins may be removed from a magnetic bead, resin, or solid surface by treatment with a TEV protease.

Example 3

PARP Activity Assays and Screening Methods

Figure 13:
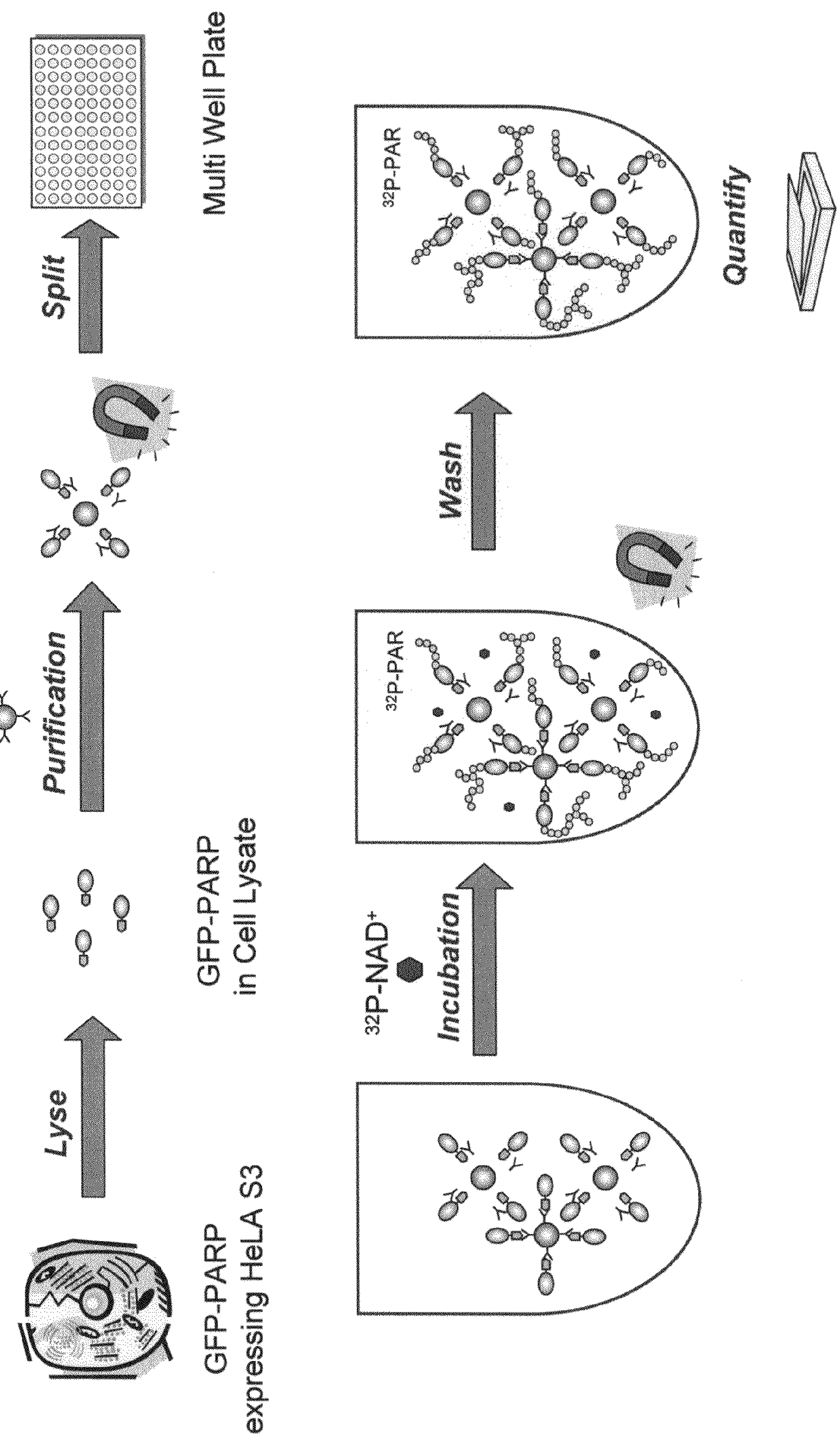
FIG. 13 is a diagram of an example of an activity assay using one or more of the PARP-GFP fusion proteins of the invention.

The above-described PARP fusion proteins may be used in PARP activity assays and in assays to identify an activator or inhibitor for a specific PARP or a specific subset of PARPs. An example of such an activity assay in shown in FIG. 13. In this example, cell lysate is first prepared from a HeLa S3 cell culture expressing one or more PARP-GFP fusion proteins. The cell lysate is then incubated with an anti-GFP polyclonal antibody bound to Dynabead® Protein A beads, and the beads magnetically removed from the cell lysate. The isolated beads bound to one or more PARP-GFP fusion proteins are placed into a multi-well plate and incubated with a labeled $NAD^+$ substrate (e.g., $^{32}P$-$NAD^+$). Following incubation with the labeled $NAD^+$ substrate, the magnetic beads bound with the one or more PARP-GFP proteins are magnetically isolated or washed, and the level of the label (i.e., the label present in the labeled $NAD^+$ substrate) that is covalently attached to the one or more PARP-GFP fusion proteins bound to the magnetic beads is determined (e.g., the amount of $^{32}P$ covalently bound to the one or more PARP-GFP proteins attached to the beads). This assay provides a means of measuring the auto-modulation activity of one or more PARP-GFP fusion proteins (e.g., the ability of a PARP to modify its own structure by catalyzing the covalent attachment of one or more ADP-ribose molecules). The assay may also be designed such that lysate or PARP-GFP fusion proteins isolated from several different transfected HeLa S3 cells, each expressing a different PARP-GFP fusion proteins or subset of PARP-GFP fusion proteins, may be placed in different wells of the multi-well plate. The assay may also be designed such that the lysate from several different transfected HeLa S3 cells is combined, wherein the lysate from each transfected HeLa S3 cell culture contains one or more PARP-GFP fusion proteins. In a different version of the assay, the PARP-GFP fusion proteins may contain a protease recognition site. In this version of the assay, the one or more PARP-GFP fusion proteins bound to the magnetic beads may be treated with a specific protease (i.e., a protease that recognizes a protease recognition sequence in the PARP-GFP fusion protein) to mediate release of the PARP-GFP fusion protein from the magnetic bead.

Figure 14:
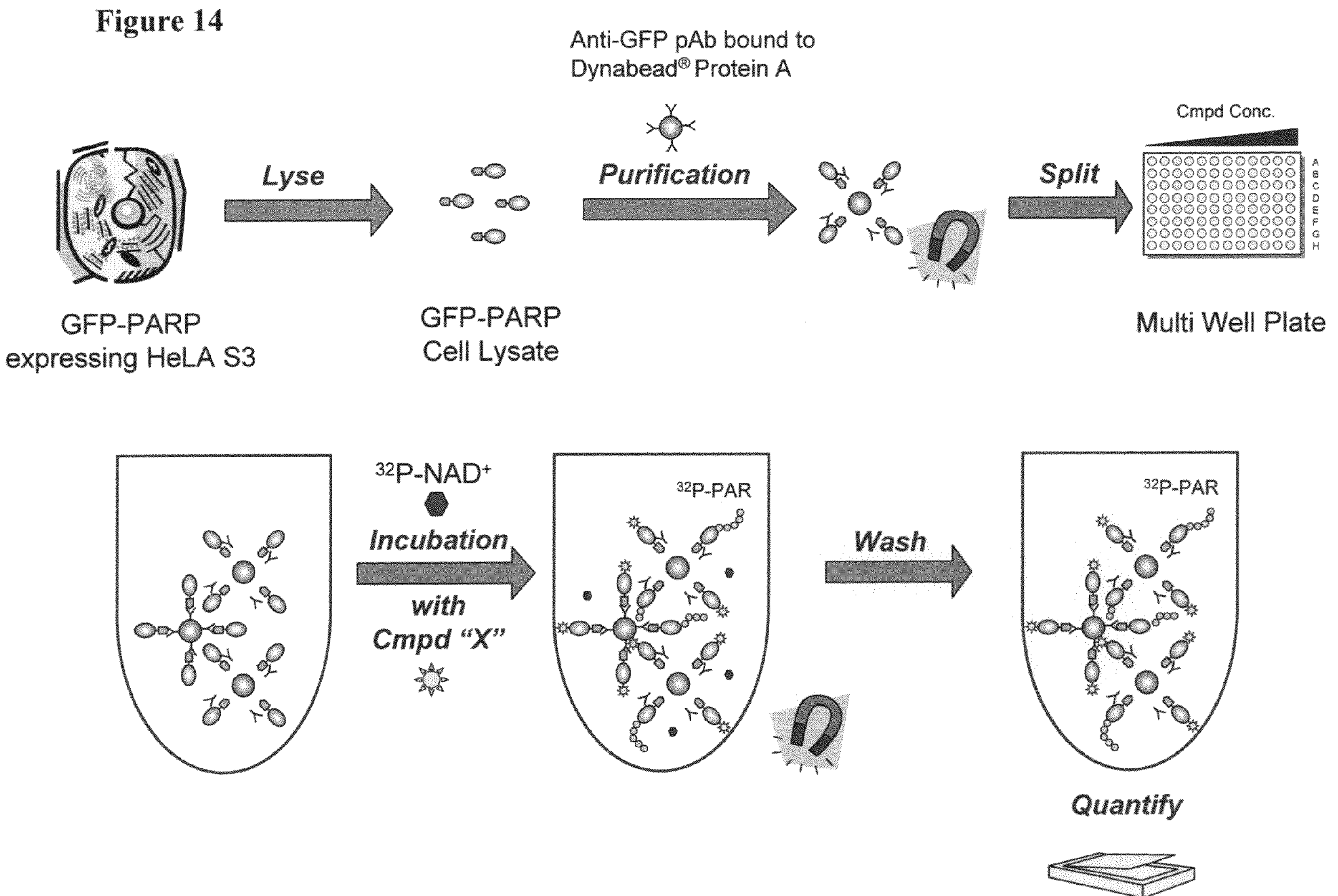
FIG. 14 is a diagram of an example of an assay for identifying an activator of one or more PARP-GFP fusion proteins of the invention.

FIG. 14 provides an example of the use of the PARP-GFP fusion proteins of the invention for the identification of an agent that specifically inhibits the activity of one or more PARPs. This assay is similar to the assay described above, except that the one or more PARP-GFP fusion proteins is incubated with both a test agent and a labeled $NAD^+$ substrate. A specific PARP inhibitor will decrease the amount of the label (i.e., the label present in the labeled $NAD^+$ substrate) covalently attached to the one or more PARP-GFP fusion proteins bound to the magnetic beads relative to the amount of the label attached to the one or more PARP-GFP fusion proteins in the absence of the test agent. In different examples of this assay, lysate or PARP-GFP fusion proteins isolated from two or more different transfected HeLa S3 cells, each expressing a different PARP-GFP fusion protein or subset of PARP-GFP fusion proteins, may be placed in different wells of the multi-well plate. The assay may also be designed such that the lysate from several different transfected HeLa S3 cells is combined, wherein the lysate from each transfected HeLa S3 cells contains one or more PARP-GFP fusion proteins. The assay may also be specifically designed to identify inhibitors of a specific PARP-GFP protein or subset of PARP-GFP proteins including the subsets of: one or more of PARP1-GFP, PARP2-GFP, PARP5A-GFP, PARP5B-GFP, PARP7-GFP, PARP8-GFP, PARP14-GFP, and PARP16-GFP; one or more of PARP5A-GFP, PARP12-GFP, PARP13.1-GFP, PARP13.2-GFP, PARP15-GFP; PARP11-GFP; or PARP13.1-GFP.

Similar to the examples, described above, the PARP-GFP fusion proteins of the invention may be used to identify activators of one or more specific PARPs. In this instance, the assay may be used to identify agents that increase the amount of the label (i.e., the label present in the labeled $NAD^+$ substrate) covalently attached to the one or more PARP-GFP fusion proteins bound to the magnetic beads relative to the amount of the label covalently attached to the one or more PARP-GFP fusion proteins in the absence of the test agent. Preferably, this assay may be designed to identify activators of a specific PARP-GFP fusion protein or subset of PARP-GFP fusion proteins including the subsets of: one or more of PARP1-GFP, PARP2-GFP, PARP5A-GFP, PARP5B-GFP, PARP7-GFP, PARP8-GFP, PARP14-GFP, and PARP16-GFP; one or more of PARP5A-GFP, PARP12-GFP, PARP13.1-GFP, PARP13.2-GFP, and PARP15-GFP; PARP11-GFP; or PARP13.1-GFP.

Example 4

Involvement of PARPs in Stress Granule Formation and Disassembly

We have discovered through a PARP family-wide RNAi screen that several PARP proteins are involved in the cell cycle and are required for progression through mitosis (e.g., PARP16). The identity of the various substrate proteins of the different PARP proteins remains largely unknown. To further identify PARP substrate proteins and/or proteins that bind to poly-ADP-ribose polymers, the Bio-Gel P-6 resin shown in FIG. 15 was used to purify proteins that bind poly-ADP-ribose polymer and/or act as an acceptor of a ADP-ribose molecule or a poly-ADP-ribose polymer. FIG. 15 also shows a Coomassie Blue-stained SDS-PAGE gel showing the proteins present in the HeLa Kyoto cell extract (Extract), in cell extract following lectin clarification (Lectin Clarification), in the lysate prior to passing over the Bio-Gel P-6 resin (Input), in the pellet following centrifugation of the resin (Pellet), and in the eluate following treatment with poly-ADP-ribose glycohydrolase ARH3 (ARH3 Release). The data in FIG. 15 demonstrates the selective purification of proteins bound to the Bio-Gel P-6 resin.

Figure 16:
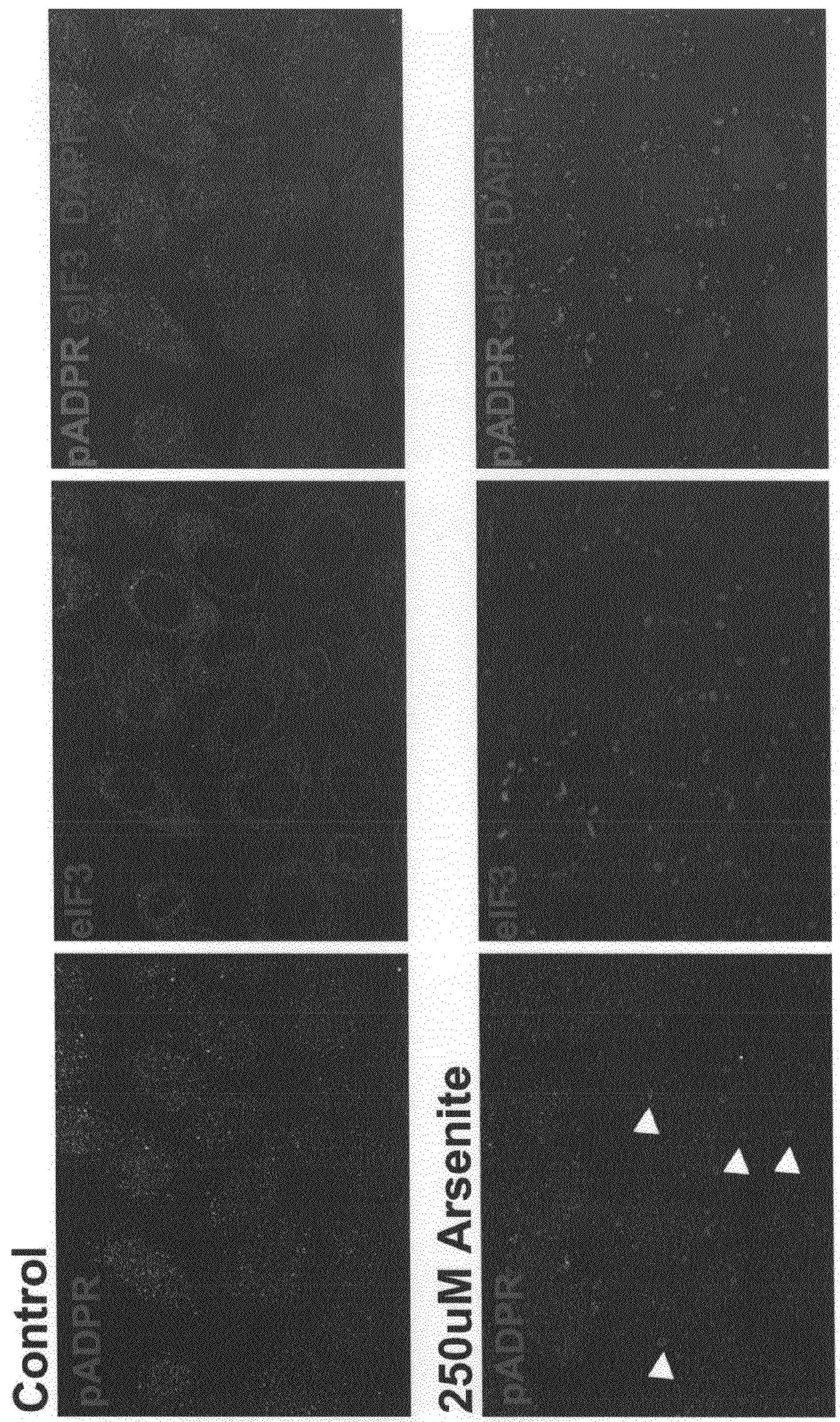
FIG. 16 is a set of micrographs showing the co-localization of poly-ADP ribose polymers (pADPR) and eIF3, a part of the translation initiation complex and a marker of stress granules, in HeLa Kyoto cells following treatment with 0 or 250 μM sodium arsenite for 30 minutes and immunostaining with primary antibodies specific for poly-ADP-ribose polymers and eIF3, and Alexa Fluor 594 or 488 secondary antibodies (Invitrogen).

We have discovered that poly-ADP-ribose polymers are associated with stress granules in cells during exposure to stress conditions. FIG. 16 shows the co-localization of poly-ADP-ribose polymers and eIF3, a marker of stress granules, in HeLa Kyoto cells following treatment with 0 or 250 μM sodium arsenite for 30 minutes and immunostaining with fluorescently-labeled antibodies specific for poly-ADP-ribose polymers and eIF3. The data indicate that stress granules contain proteins modified with poly-ADP-ribose polymers.

Figure 17:
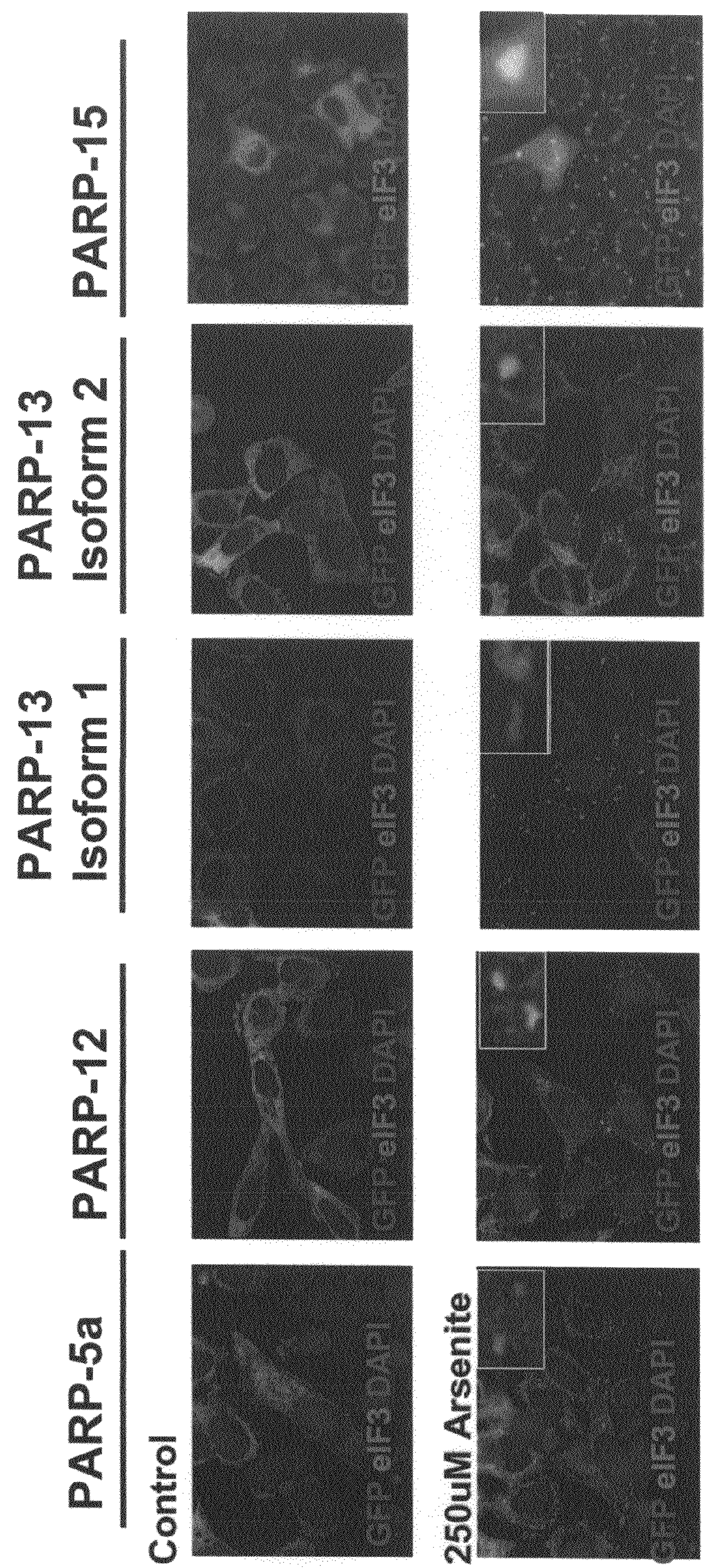
FIG. 17 is a set of micrographs showing the co-localization of PARP-GFP fusion proteins with eIF3 in transfected HeLa Kyoto cells following treatment with 0 or 250 μM sodium arsenite for 30 minutes. In these experiments, HeLa Kyoto cells were transfected with a pEGFP-C1 plasmid expressing PARP5A-GFP, PARP12-GFP, PARP13.1-GFP, PARP13.2-GFP, or PARP15-GFP fusion protein and treated with 0 or 250 μM sodium arsenite. The cells were fixed and stained with anti-GFP and anti-eIF3, and secondary fluorescently-labeled antibodies (Alexa Fluor 594 or 488 antibodies (Invitrogen)) prior to imaging.

In order to identify the specific PARP proteins that mediate the formation of the poly-ADP-ribose polymers present in stress granules, experiments were performed to determine whether the different PARP-GFP fusion proteins localize to stress granules. In these experiments, HeLa Kyoto cells transfected with a pEGFP-C1 plasmid expressing a PARP-GFP fusion protein were visualized using fluorescently-labeled anti-GFP and anti-eIF3 antibodies following treatment with 250 μM sodium arsenite for 30 minutes (FIG. 17). The data indicate that the PARP5A-GFP, PARP12-GFP, PARP13.1-GFP, PARP13.2-GFP, and PARP15-GFP fusion proteins localize to stress granules under stress conditions.

Figure 18:
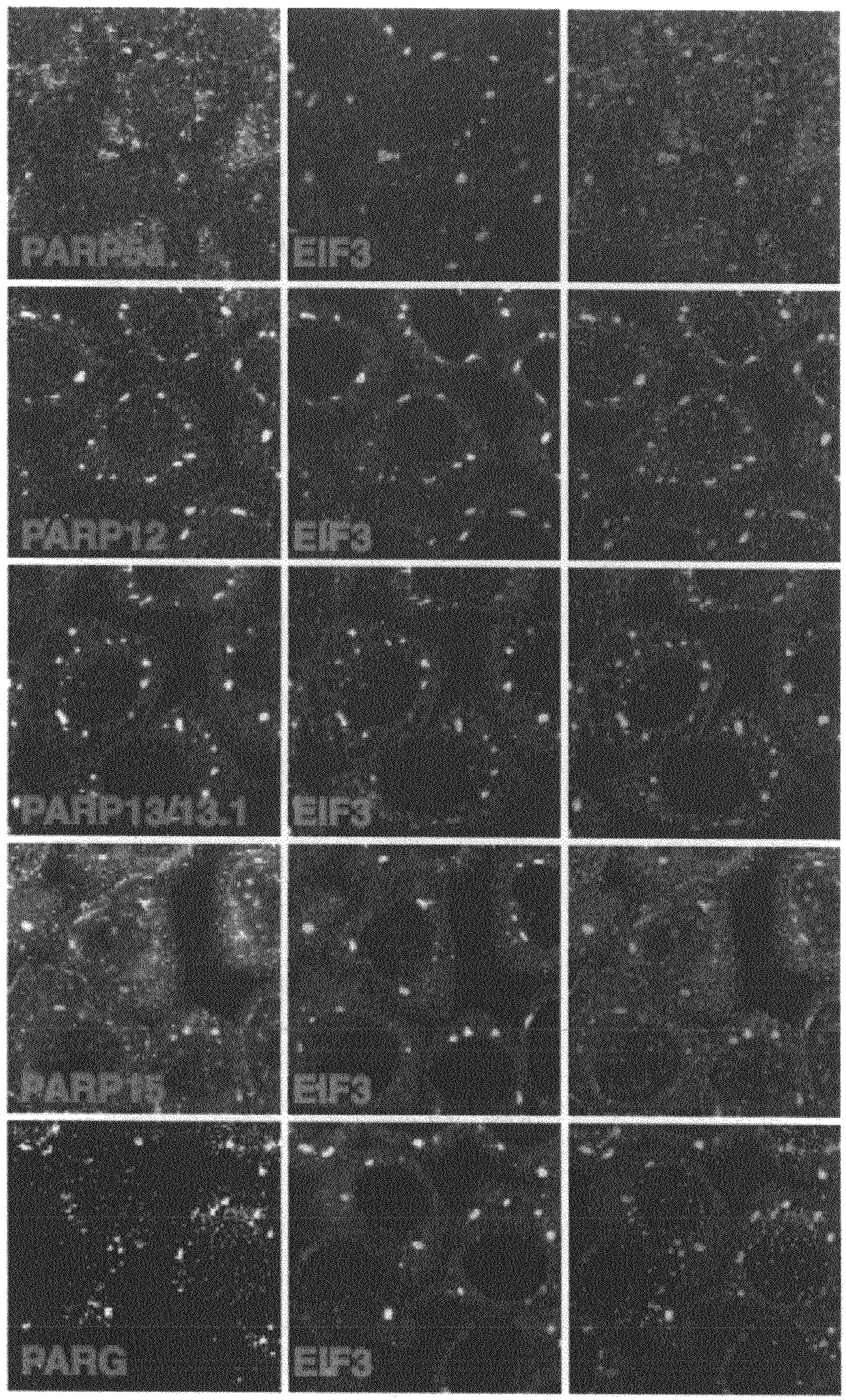
FIG. 18 is a set of micrographs showing the co-localization of endogenous PARP5A, PARP12, PARP13/13.1, PARP15, or poly-ADP-ribose glycohydrolase (PARG), and eIF3 (a stress granule marker) in HeLa Kyoto cells following treatment with 250 μM sodium arsenite for 30 minutes. In these experiments, cells were stained with rabbit antibodies specific for one of PARP5A, PARP12, PARP13/13.1, PARP15, or PARG, and an anti-eIF3 antibody, and fluorescently-labeled secondary antibodies (Alexa Fluor 594 or 488 antibodies (Invitrogen)).
Figure 19:
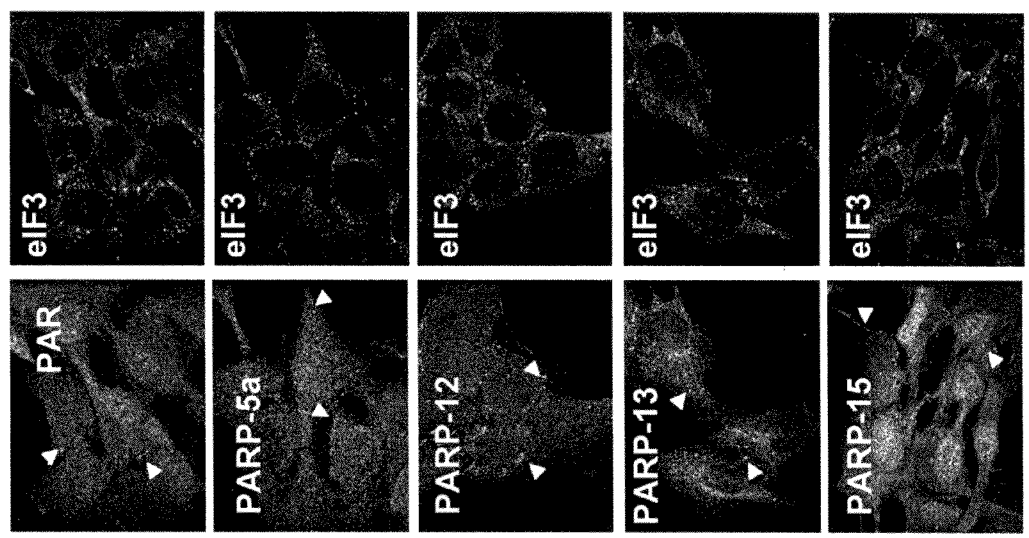
FIG. 19 is a set of micrographs showing the localization of poly-ADP-ribose (PAR), endogenous PARP5A, PARP12, PARP13, and PARP15, and eIF3 (a stress granule marker) in hTERT RPE cells following treatment with 250 μM sodium arsenite for 30 minutes. In these experiments, cells were stained with antibodies specific for one of PAR, PARP5A, PARP12, PARP13, or PARP15, or an anti-eIF3 antibody, and a secondary fluorescently-labeled antibodies (Alexa Fluor 594 or 488 antibodies (Invitrogen)).

Endogenous PARP5A, PARP12, PARP13/13.1, PARP15, and poly-ADP-ribose glycohydrolase (PARG) also localize to stress granules in HeLa Kyoto cells following treatment with 250 μM sodium arsenite for 30 minutes (FIG. 18). In these experiments, the fixed cells were visualized using antibodies specific for one of PAR5A, PARP12, PARP13/13.1, PARP15, or PARG, and an anti-eIF3 antibody, and secondary fluorescently-labeled antibodies. The data indicate that PARG, as well as the endogenous- and fusion protein-forms of PARP5A, PARP12, PARP13/13.1, and PARP15, localize to stress granules under stress conditions. In a similar set of experiments using hTERT RPE cells, endogenous PARP5A, PARP12, PARP13, and PARP15 showed a similar cellular localization following exposure to 250 μM sodium arsenite for 30 minutes, as was observed in HeLa Kyoto cells (FIG. 19).

Experiments using time-lapse immunofluorescence microscopy in live HeLa Kyoto cells further indicate that endogenous PARP12, PARP12-GFP, endogenous PARP13, and PARP13-GFP localize to stress granules at an early point in stress granule assembly and therefore, may play a regulatory role in the formation of stress granules (data not shown).

Figure 20:
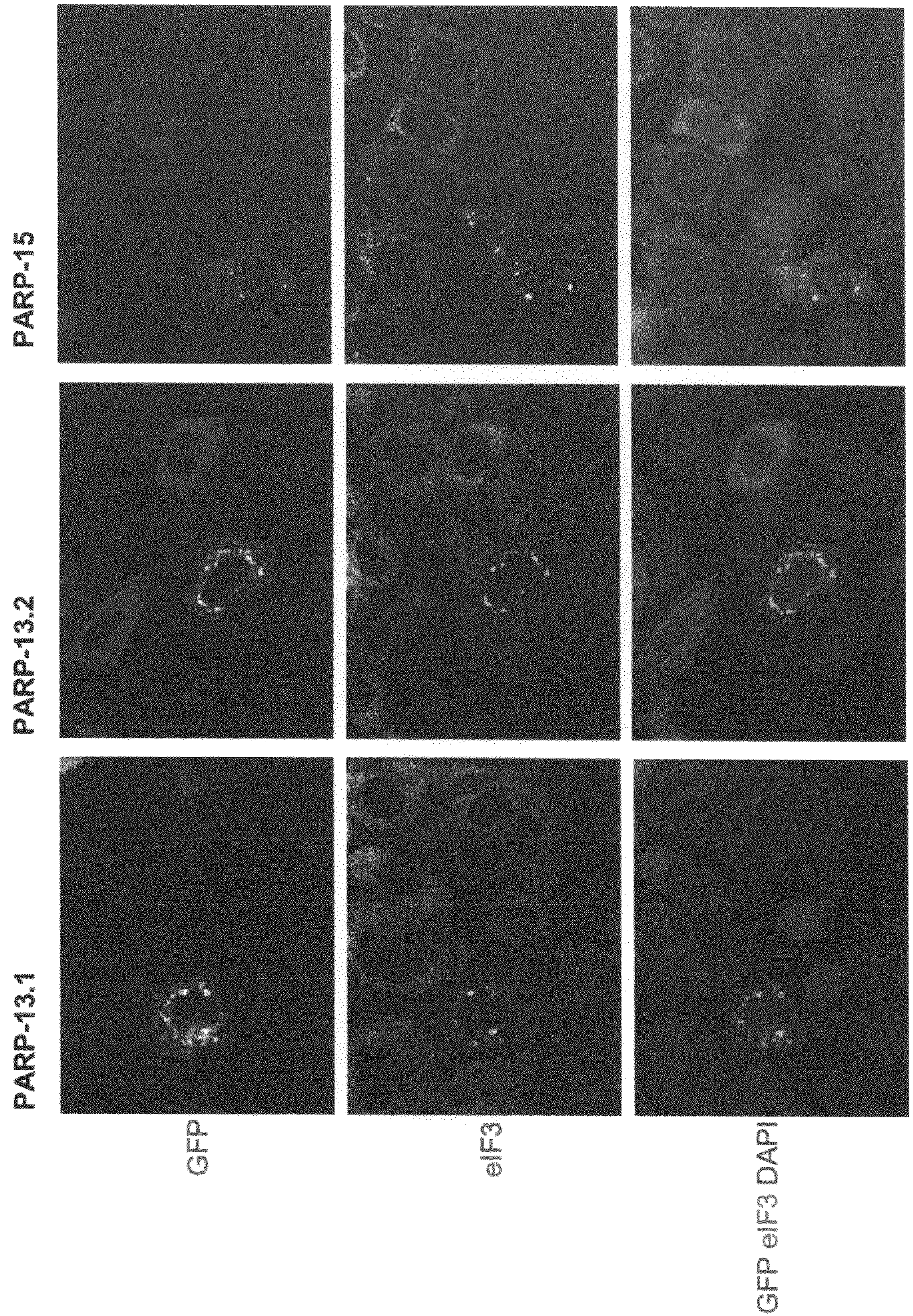
FIG. 20 is a set of micrographs showing the effect of PARP13.1-GFP, PARP13.2-GFP, or PARP15-GFP overexpression on stress granule formation. In these experiments, HeLa Kyoto cells were transfected with a plasmid expressing PARP13.1-GFP, PARP13.2-GFP, or PARP15-GFP. The cells were fixed and stained using rabbit anti-GFP and anti-eIF3 antibodies, and fluorescently-labeled secondary antibodies (Alexa Fluor 594 or 488 antibodies (Invitrogen)). The cells were also co-stained with DAPI.

In an additional set of experiments, the effect of PARP13.1, PARP13.2, and PARP15 on stress granule formation was further studied by measuring the effect of overexpression of PARP13.1-GFP, PARP13.2-GFP, and PARP15-GFP on stress granule formation. In these experiments, HeLa Kyoto cells were transfected with a pEGFP-C1 plasmid encoding PARP13.1-GFP, PARP13.2-GFP, or PARP15-GFP. The transfected cells were stained with anti-GFP antibodies, anti-eIF3 antibodies, and fluorescently-labeled secondary antibodies. These data indicate that overexpression of PARP13.1-GFP, PARP13.2-GFP, or PARP15-GFP fusion protein nucleates stress granule formation (FIG. 20).

Figure 21:
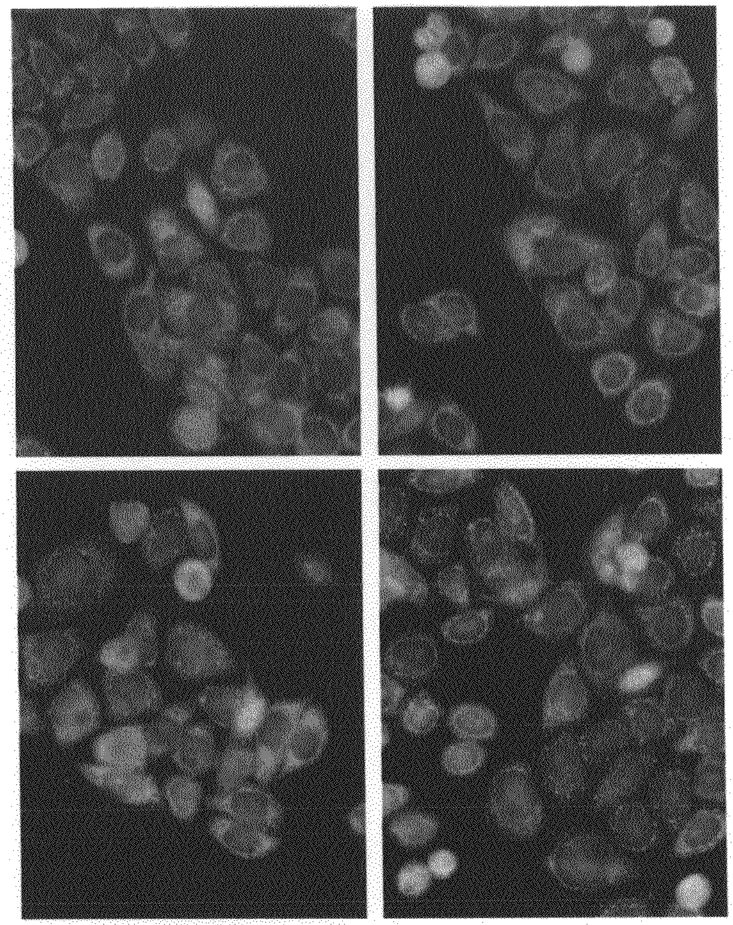
FIG. 21 is a set of micrographs showing the co-localization of PARP11-GFP and eIF3 (a stress granule marker) in HeLa Kyoto cells transfected with a pEGFP-C1 vector expressing PARP11-GFP following treatment with 250 μM sodium arsenite for 30 minutes. Following arsenite treatment, the cells were immediately fixed and stained using rabbit anti-GFP and anti-eIF3 antibodies, and fluorescently-labeled secondary antibodies (Alexa Fluor 594 or 488 antibodies (Invitrogen)). The cells were also stained with DAPI.

In contrast to the effect mediated by overexpression of PARP13.1-GFP, PARP13.2-GFP, or PARP15-GFP fusion protein, overexpression of PARP11-GFP in HeLa Kyoto cells mediates a decrease in stress granule formation following treatment with 250 μM sodium arsenite for 30 minutes (FIG. 21). In this experiment, HeLa Kyoto cells transfected with a pEGFP-C1 vector expressing a PARP11-GFP fusion protein were treated with sodium arsenite, and stained with anti-GFP antibodies, anti-eIF3 antibodies, and fluorescently-labeled secondary antibodies. These data indicate that overexpression of PARP11-GFP suppresses the formation of stress granules in cells exposed to stress conditions.

Experimental Methods

HeLa Kyoto cells were cultured as described above. Lipofectamine 2000 (Invitrogen) was used to transfect the HeLa Kyoto cells with a pEGFP-C1 plasmid encoding a PARP-GFP fusion protein (described above) according to the manufacturer's instructions. For stress granule induction, cells were treated with 250 μM sodium arsenite for 30 minutes. For long-term, real-time imaging of PARP-GFP transfected HeLa cells, the cells were split into 24-well glass bottom plates and imaged every 20 minutes for 48 hours. Images were collected on a Nikon TE2000 confocal microscope equipped with a Yokogawa CSU-X1 spinning disc head, Hamamatsu ORCA ER digital camera, and NIS-Elements imaging software.

Example 5

Involvement of PARG and ARH3 in Stress Granule Disassembly

Figure 22:
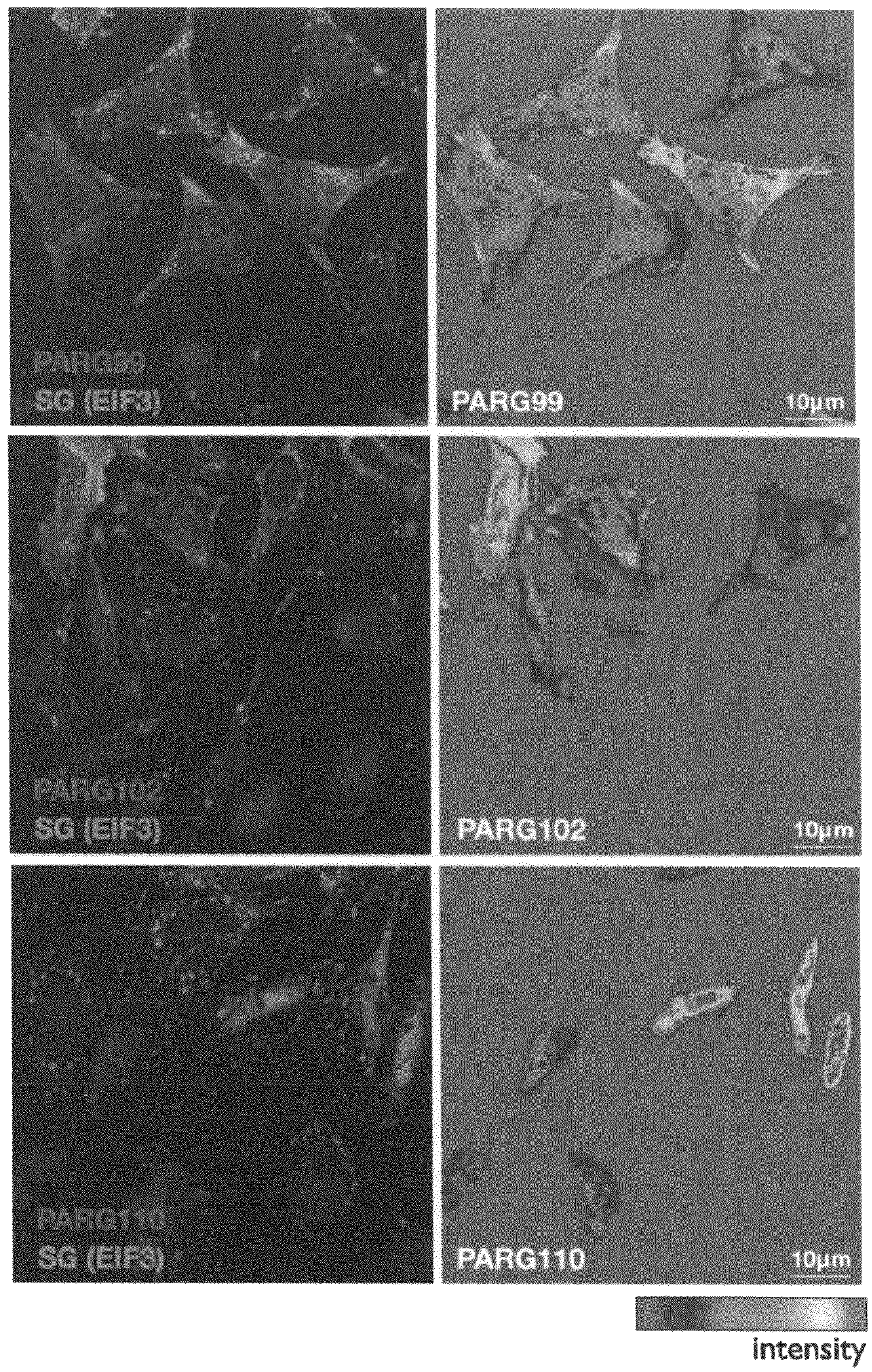
FIG. 22 is a set of micrographs showing the effect of PARG99-GFP, PARG102-GFP, or PARG110-GFP overexpression on stress granule formation in HeLa Kyoto cells transfected with a pEGFP-C1 plasmid containing a nucleic acid sequence encoding each PARG-GFP fusion protein, following treatment with 100 μM sodium arsenite for 30 minutes. Following arsenite treatment, the cells were fixed and stained with rabbit anti-GFP and anti-eIF3 antibodies, and fluorescently-labeled secondary antibodies (Alexa Fluor 594 or 488 antibodies (Invitrogen)). The images shown in the right panels show the same data using a threshold filter.

In order to determine the importance of poly-ADP-ribose polymers on stress granule formation and disassembly, an additional set of experiments were performed to test the effect of PARG and ARH3 activity on stress granule dynamics. In a first set of experiments, HeLa Kyoto cells were transfected with a pEGFP-C1 plasmid encoding PARG99-GFP, PARG102-GFP, or a PARG110-GFP fusion protein. Overexpression of PARG99-GFP, PARG102-GFP, or PARG110-GFP reduces the formation of stress granules in HeLa Kyoto cells following exposure to 100 μM sodium arsenite for 30 minutes (FIG. 22). In these experiments, formation of stress granules was determined by staining the fixed cells with anti-eIF3 antibodies and secondary fluorescently-labeled antibodies. These data indicate that PARG activity (hydrolysis of poly-ADP-ribose) inhibits the formation of stress granules in cells under stress conditions.

Figure 23:
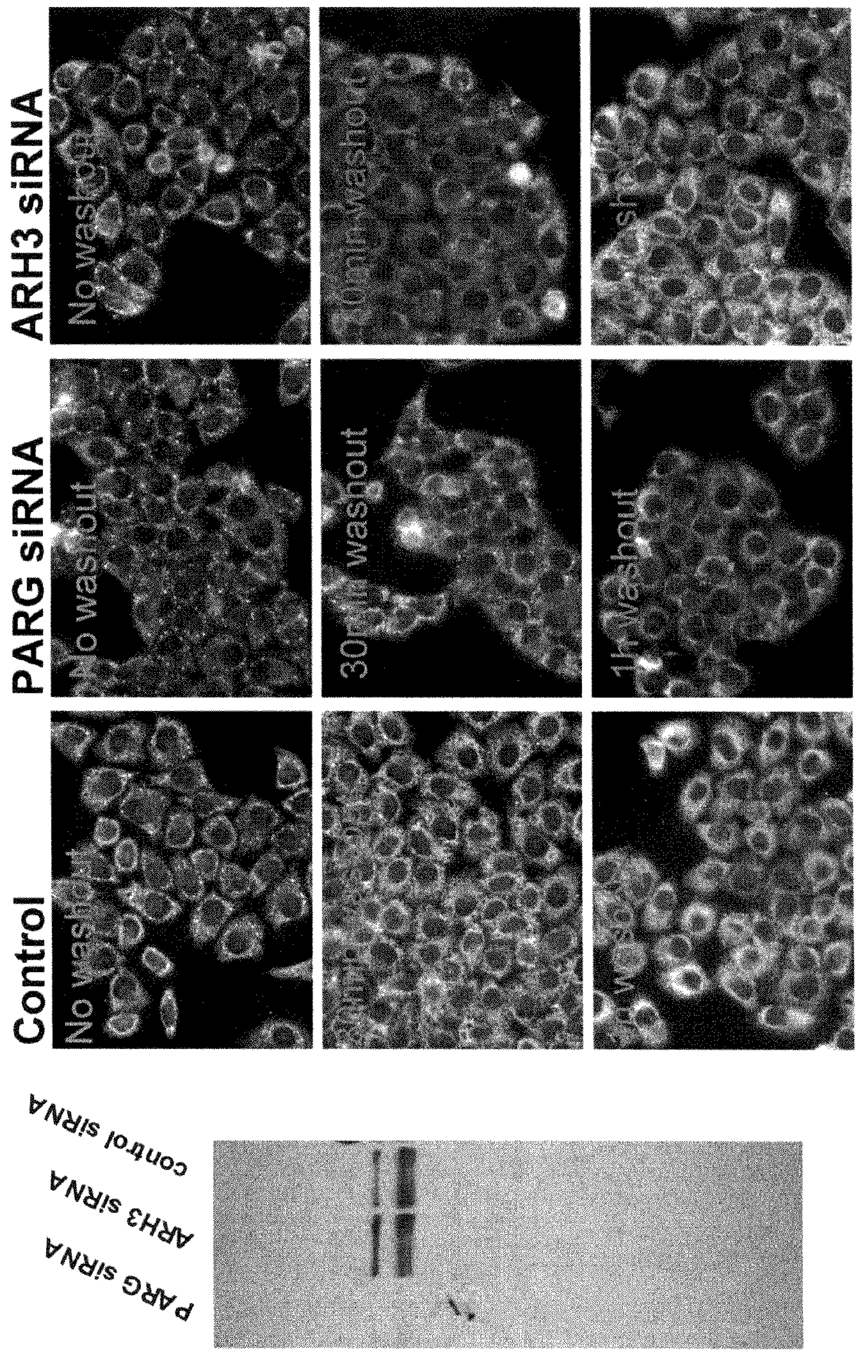
FIG. 23 is a set of micrographs showing the effect of PARG or ARH3 knockdown on stress granule formation in HeLa Kyoto cells transfected with 30 nM PARG siRNA (CCAGUUGGAUGGACACUAAUU (SEQ ID NO: 34) and UUACGAAGGUACCA UAGAAUU (SEQ ID NO: 35)), ARH3 siRNA (GGACAGAAGCCUUGUACUAUU (SEQ ID NO: 36) and CCAUUGCUGGUGCCUACUAUU (SEQ ID NO: 37)), or a control siRNA (All Stars Negative Control siRNA; Qiagen Catalog No. 1027280) following treatment with 100 μM sodium arsenite for 30 minutes, or 30 minutes or 1 hour following sodium arsenite washout. The cells were fixed and stained with an anti-eIF3 antibody and secondary fluorescently-labeled antibodies (Alexa Fluor 594 or 488 antibodies) to visualize stress granule formation. The panel on the left shows an immunoblot of cell lysate from HeLa Kyoto cells treated with 30 nM PARG siRNA, ARH3 siRNA, or control siRNA for 48 hours. The immunoblot was developed using an anti-PARG antibody.
Figure 24:
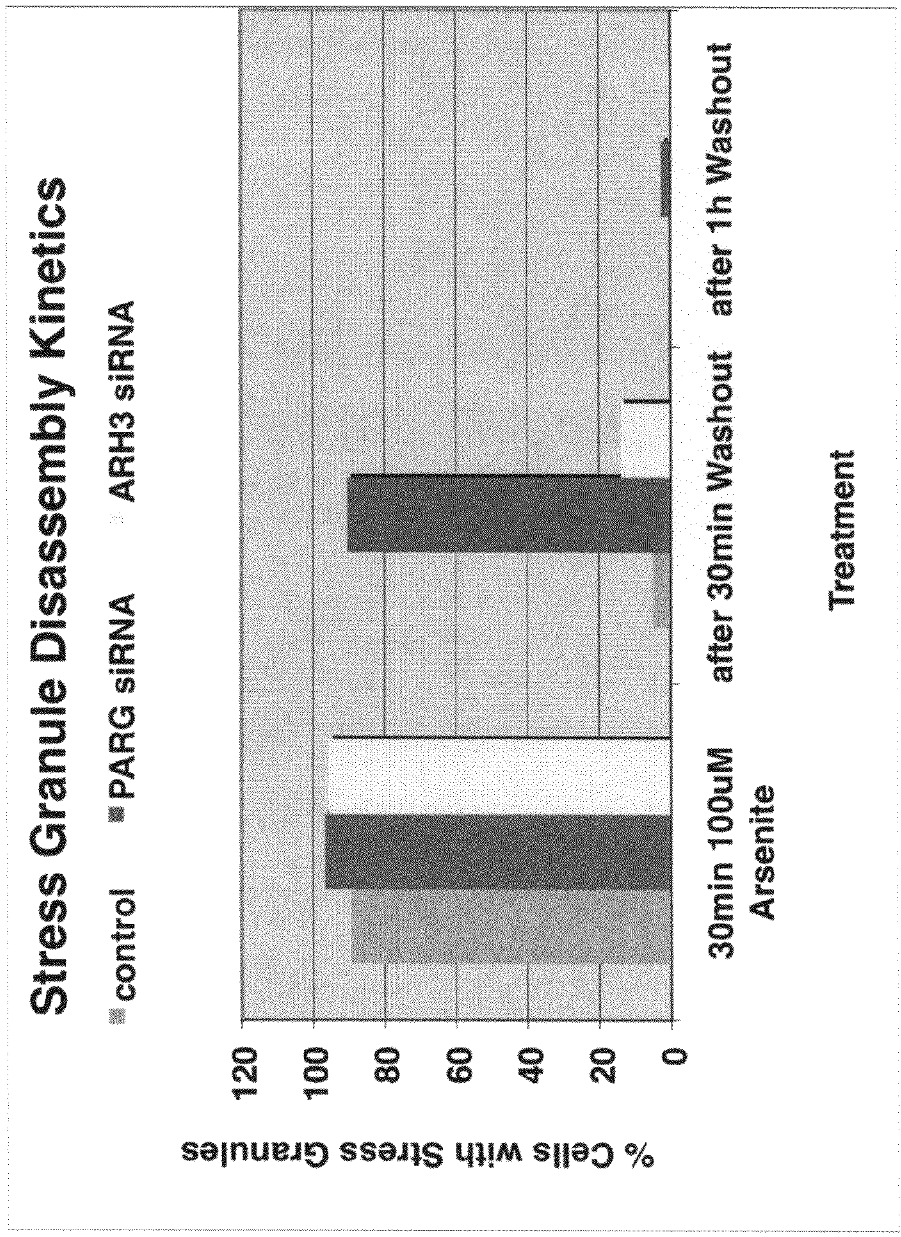
FIG. 24 is a graph showing the percentage of HeLa Kyoto cells transfected with 30 nM PARG siRNA (SEQ ID NOS: 34 and 35), ARH3 siRNA (SEQ ID NOS: 36 and 37), or a control siRNA (All Stars Negative Control siRNA; Qiagen Catalog No. 1027280) containing stress granules following treatment with 100 μM sodium arsenite for 30 minutes, or 30 minutes or 1 hour following sodium arsenite washout. The cells were fixed and stained with a fluorescently-labeled anti-eIF3 antibody to visualize stress granule formation.

Another set of experiments was performed to determine the effect of knockdown of PARG (SEQ ID NO: 42) or ARH3 (SEQ ID NO: 41) on stress granule formation in cells under stress conditions. In these experiments, HeLa Kyoto cells were treated with 30 nM siRNA specific for PARG (SEQ ID NOS: 34 and 35) or ARH3 (SEQ ID NOS: 36 and 37), or a control siRNA (All Stars Negative Control siRNA; Qiagen Catalog No. 1027280), and treated with 100 μM sodium arsenite for 30 minutes, or 30 minutes or 1 hour following sodium arsenite washout (FIG. 23). Cells treated with a PARG siRNA or ARH3 siRNA show a sustained presence of stress granules following removal of sodium arsenite from the culture medium (via imaging using anti-eIF3 antibodies and fluorescently-labeled secondary antibodies). These data indicate that PARG and ARH3 activity (hydrolysis of poly-ADP-ribose) has a positive effect on stress granule disassembly, and that poly-ADP-ribose turnover kinetics regulate the formation/disassembly of stress granules. The percentage of cells with stress granules following 30-minute washout and 1-hour washout after arsenite treatment was quantitated for cells treated with control siRNA, PARG siRNA, and ARH3 siRNA (FIG. 24). These data indicate that knockdown of PARG and ARH3 reduces the rate of stress granule disassembly following removal of the stress condition (sodium arsenite).

Experimental Methods

HeLa Kyoto cells were cultured in medium as described above. In PARG overexpression experiments, Lipofectamine 2000 (Invitrogen) was used to transfect HeLa Kyoto cells with pEGFP-C1 plasmids containing the nucleic acid sequences for each PARG isoform, i.e., PARG99, PARG102, and PARG110 (sequences described in Meyer-Ficca et al., *Exp. Cell. Res.* 297(2):521-532, 2004) according to the manufacturer's instructions. In PARG knockdown experiments, cells were treated with 30 nM of a siRNA targeting PARG (SEQ ID NOS: 34 and 35), a siRNA targeting ARH3 (SEQ ID NO: 36 and 37), or a control siRNA (AllStars Negative Control siRNA; Qiagen Catalog No. 1027280) using Lipofectamine 2000 according to the manufacturer's instructions. In these experiments, stress granule formation was induced by treatment with 100 μM sodium arsenite for 30 minutes. For stress granule disassembly experiments, the media was replaced after sodium arsenite treatment, and cells were incubated for 30 minutes and I hour prior to fixation and immunostaining. At least 200 cells were counted for each condition (in triplicate) to determine the percentage of cells containing stress granules.

Example 6

Stress Granule Proteins Bind to GFP-PARPs

Figure 25:
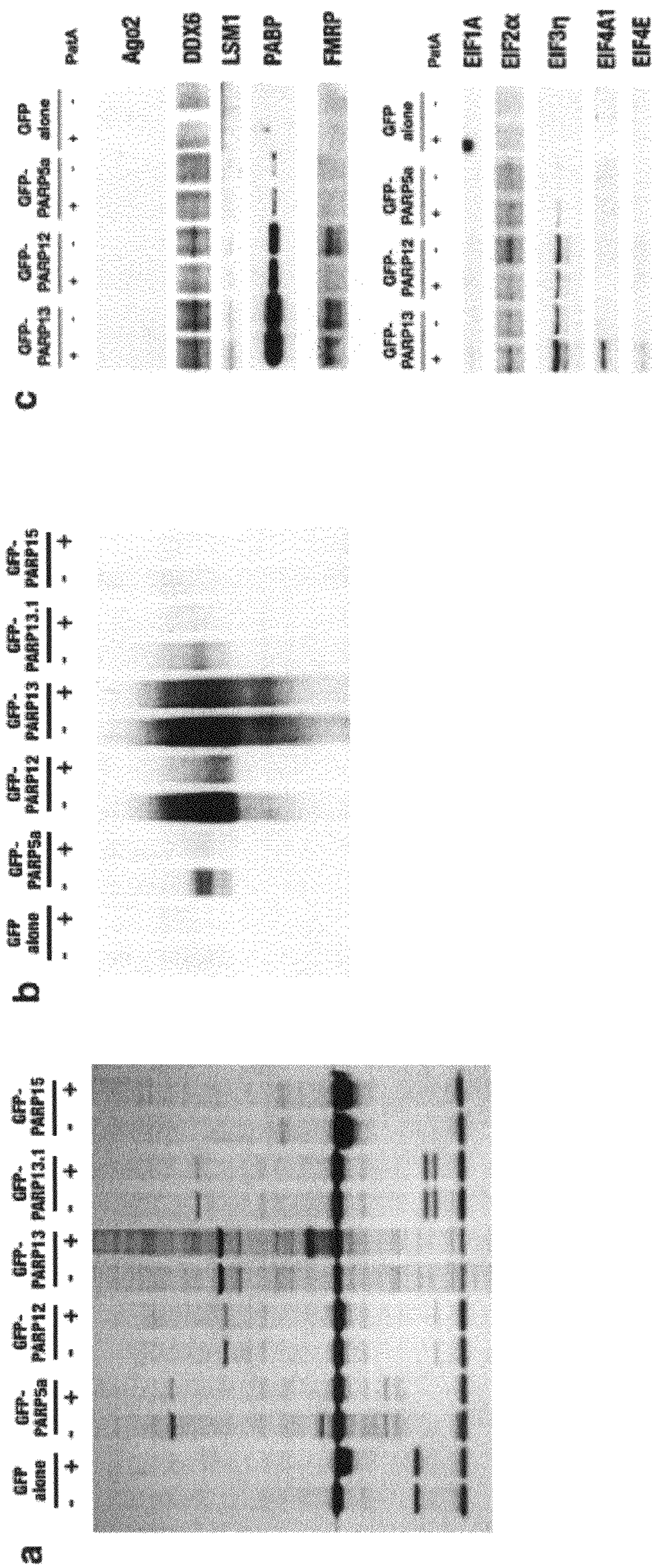
FIG. 25A is a Silver-stained 4-12% SDS-PAGE gel showing the proteins immunoprecipitated with an anti-GFP antibody from lysate from HeLa S3 cells transfected with a pEGFP-C1 plasmid expressing GFP alone, PARP5A-GFP, PARP12-GFP, PARP13-GFP, PARP13.1-GFP, or PARP15-GFP following treatment with 0 or 250 μM sodium arsenite for 30 minutes.
FIG. 25B is picture of an immunoblot of a 4-12% SDS-PAGE gel containing proteins immunoprecipitated with an anti-GFP antibody from lysate from HeLa S3 cells transfected with a pEGFP-C1 plasmid expressing GFP, PARP5A-GFP, PARP12-GFP, PARP13-GFP, PARP13.1-GFP, or PARP15-GFP following treatment with 0 or 250 μM sodium arsenite for 30 minutes. The immunoblot was developed using a polyclonal anti-poly-ADP-ribose antibody.
FIG. 25C is a picture of several immunoblots of a 4-12% SDS-PAGE gel containing proteins immunoprecipitated with an anti-GFP antibody from lysate from HeLa S3 cells transfected with a pEGFP-C1 plasmid expressing GFP, PARP5A-GFP, PARP12-GFP, PARP13-GFP, PARP13.1-GFP, or PARP15-GFP following treatment with 0 or 20 nM pateamine A for 30 minutes. The immunoblots were developed using one of the following antibodies: anti-Ago2, anti-DDX6, anti-LSM1, anti-PABP, anti-FMRP, anti-eIF1A, anti-eIF2σ, anti-eIF3η, anti-eIF4A1, and anti-eIF4E.

Experiments were performed to further identify stress granule-related proteins that may bind and be the substrates of one or more of the PARPs localized in stress granules (e.g., PARP5A, PARP12, PARP13, PARP13.1, and PARP15). In these experiments, HeLa S3 cells were transfected with pEGFP-C1 plasmids containing a nucleic acid sequence encoding PARP5A-GFP, PARP12-GFP, PARP13-GFP, PARP13.1-GFP, or PARP15-GFP fusion protein and treated with 0 or 250 μM sodium arsenite for 30 minutes. The resulting cell lysate was immunoprecipitated using anti-GFP antibodies and the resulting immunoprecipitated proteins were electrophoresed using SDS-PAGE. The resulting gel indicates that each PARP-GFP fusion protein binds to several proteins and that treatment with sodium arsenite results in an alteration in the amount and identity of the proteins binding to each PARP-GFP fusion protein (FIG. 25A). In a similar experiment, the immunoprecipitated proteins are transferred to a membrane and immunostained with an anti-poly-ADP-ribose antibody. The data in this experiment show that PARP5A-GFP, PARP12-GFP, PARP13-GFP, and PARP13.1-GFP fusion proteins bind to poly-ADP-ribosylated proteins (FIG. 25B).

Data from a separate set of experiments indicate that several stress granule-associated proteins bind to the PARP13-GFP, PARP12-GFP, and PARP5A-GFP fusion proteins. In these experiments, HeLa S3 cells were transfected with a pEGFP-C1 plasmid encoding a PARP13-GFP, PARP12-GFP, or PARP5A-GFP fusion protein and treated with 0 or 20 nM pateamine A for 30 minutes. Cell lysates from the cells were immunoprecipitated using an anti-GFP antibody and the immunoprecipitated proteins were electrophoresed using 4-12% SDS-PAGE. The resulting proteins were transferred to a membrane and immunoblotted using commercially-available antibodies specific for different stress granule-associated proteins: Ago2, DDX6, LSM1, PABP, FMRP, eIF1A, eIF2α, eIF3η, eIF4A1, and eIF4E. The data indicate that the PARP13-GFP, PARP12-GFP, and PARP5A-GFP fusion proteins have the ability to interact with one or more of these stress granule-associated proteins under both normal (0 nM pateamine A) and stress conditions (30 nM pateamine A) (FIG. 25C).

Figure 26:
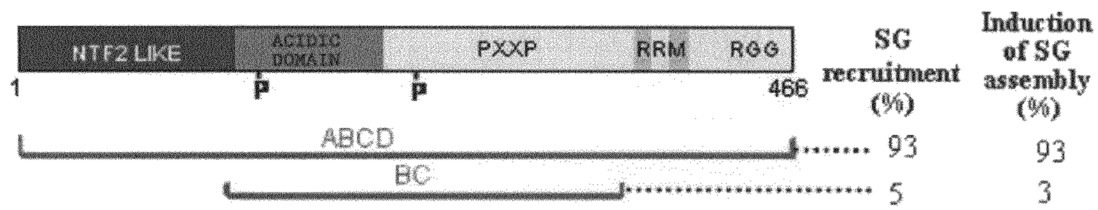
FIG. 26 (right panel) is an immunoblot of a 4-12% SDS-PAGE gel containing proteins immunoprecipitated using an anti-Ago2 antibody from untransfected HeLa cells following treatment with 0 or 250 μM sodium arsenite for 60 minutes. The immunoblot was developed using anti-poly-ADP-ribose antibodies.
Figure 26:
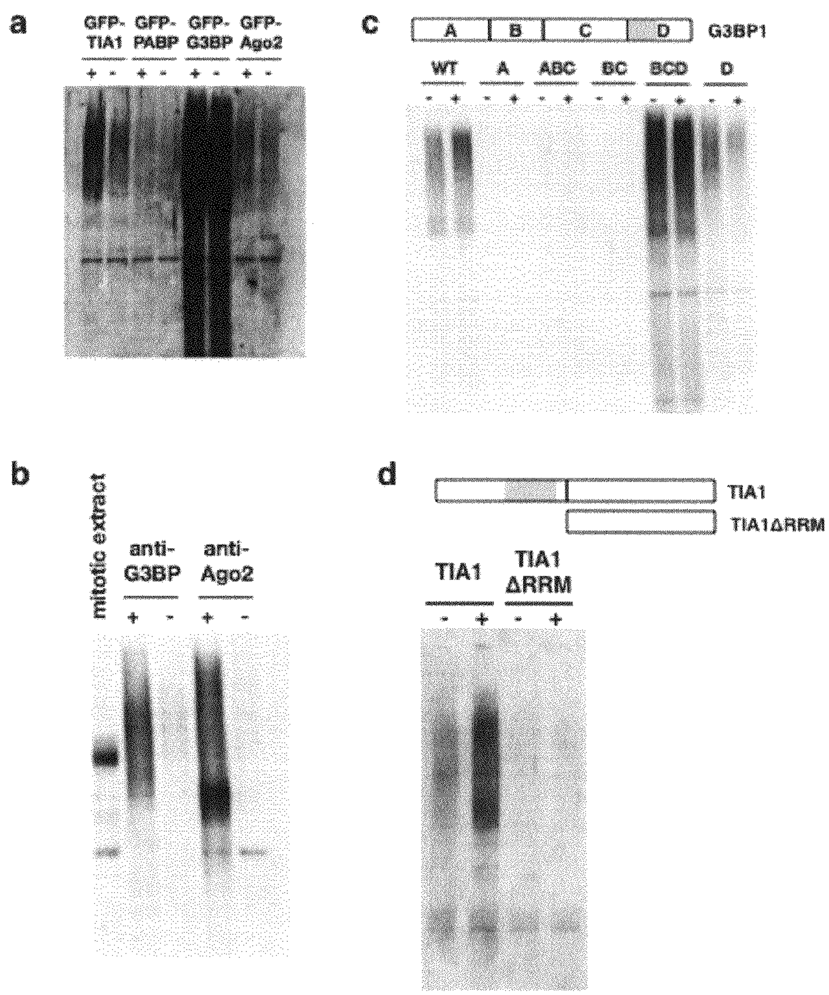

An additional set of experiments was performed to determine whether one or more stress granule-associated proteins are poly-ADP-ribosylated. In these experiments, HeLa S3 cells were transfected with a pEGFP-C1 plasmid encoding a GFP fusion protein of TIA1, PABP, G3BP, or Ago2, and treated with 0 or 20 nM pateamine A for 30 minutes. Lysates from these cells were immunoprecipitated using anti-GFP antibodies and immunoblotted using an anti-poly-ADP ribose antibody. The data show that several proteins bind the TIA1-GFP, PABP-GFP, G3BP-GFP, and Ago2-GFP fusion proteins in untreated (0 nM pateamine A) and treated (20 nM pateamine A) cells (FIG. 26A). In an additional experiment, the proteins that bind to endogenous G3BP and Ago2 proteins in 250 μM sodium arsenite-treated HeLa S3 cells were also shown to be poly-ADP-ribosylated (FIG. 26B). In this experiment, cell lysates from untransfected HeLa S3 cells treated with 0 or 250 μM sodium arsenite for 60 minutes were immunoprecipitated with anti-G3BP or anti-Ago2 antibodies and immunoblotted using an anti-poly-ADP-ribose antibody.

G3BP1, a stress granule-associated protein, was shown to be poly-ADP-ribosylated (FIG. 26C). In order to map the specific domain in G3BP1 that is modified by a poly-ADP-ribose polymer, GFP-fusion proteins of different truncation 250 μM sodium arsenite for 60 minutes. The specific nucleic acid sequences encoding each G3BP1 truncation mutant are described in Tourriere et al. (*J. Cell Biol.* 160:823-831, 2003). The cell lysate from each cell sample was immunoprecipitated using anti-GFP antibodies and immunoblotted using an anti-poly-ADP-ribose antibody. The data demonstrate that poly-ADP-ribosylation of G3BP1 occurs within the RNA-recognition motif (RRM) domain ("D" in FIG. 26C). The RRM domain of G3BP1 is a domain that binds to RNA molecules. The poly-ADP-ribosylation of G3BP1 in the RRM domain is thought to regulate the RNA-binding activity of G3BP1.

TIA1, a stress granule-associated protein, was also shown to be poly-ADP-ribosylated (FIG. 26D). In order to determine whether TIA1 is poly-ADP-ribosylated in its RRM domain, GFP-fusion proteins of full-length TIA1 and a truncation mutant of TIA1 lacking its RRM domain (TIA1ΔRRM) were expressed in HeLa S3 cells treated with 0 or 250 μM sodium arsenite for 60 minutes. The specific nucleic acid sequences encoding the full-length TIA1 and the TIA1ΔRRM truncation mutant are described in Kedersha et al. (*J. Cell Biol.* 151:1257-1268, 2000). The cell lysate from each cell sample was immunoprecipitated using anti-GFP antibodies and immunoblotting was performed using an anti-poly-ADP-ribose antibody. The data demonstrate that poly- ADP-ribosylation of TIA1 also occurs within its RNA-recognition motif (RRM) domain (FIG. 26D). The poly-ADP-ribosylation of TIA1 in its RRM domain is also thought to mediate an alteration in its RNA-binding activity.

Experimental Methods

Immunoprecipitation experiments to identify proteins binding to PARP5A-GFP, PARP12-GFP, PARP13-GFP, PARP13.1-GFP, and PARP15-GFP were performed using HeLa S3 cells transfected with a pEGFP-C1 plasmid containing a nucleic acid sequence encoding each respective PARP-GFP fusion protein following treatment with 0 or 20 nM pateamine A for 30 minutes. In each experiment, the cell lysate is incubated with an anti-GFP antibody to immunoprecipitate proteins bound to each of the PARP-GFP fusion proteins using standard methods. The resulting immunoprepitated proteins were electrophoresed on 4-12% SDS-PAGE gels, and either stained directly with Coomassie Blue or transferred onto a membrane and immunostained with one or more of the following antibodies: anti-poly-ADP-ribose, anti-Ago2, anti-DDX6, anti-LSM1, anti-PABP, anti-FMRP, anti-eIF1A, anti-eIF2α, anti-eIF3η, anti-eIF4A1, and anti-eIF4e antibodies.

Immunoprecipitation experiments using TIA1-GFP, PABP-GFP, G3BP-GFP, and Ago2-GFP fusion proteins were performed using HeLa S3 cells transfected with pEGFP-C1 plasmids containing a sequence encoding a nucleic acid sequence encoding TIA1 (Kedersha et al., *J. Cell Biol.* 151: 1257-1268, 2000), PABP (NCBI Accession No. NM_12154.2), G3BP (Tourriere et al., *J. Cell Biol.* 160:823-831, 2003), Ago2 (NCBI Accession No._002568.3), a truncation mutant of G3BP (i.e., A, ABC, BC, BCD, and D truncation mutants described in Tourriere et al., supra), or the ΔRRM truncation mutation of TIA1 (described in Kedersha et al., supra) following treatment with 0 or 20 nM pateamine A for 30 minutes. In each experiment, the cell lysate is incubated with an anti-GFP antibody to immunoprecipitate proteins bound to each of the GFP fusion proteins using standard methods. The resulting immunoprepitated proteins were electrophoresed on 4-12% SDS-PAGE gels, and either stained directly with Coomassie Blue or transferred onto a membrane and immunostained with anti-poly-ADP-ribose antibody.

Example 7

PARP13 and PARG Regulation of RNAi Activity

Figure 27:
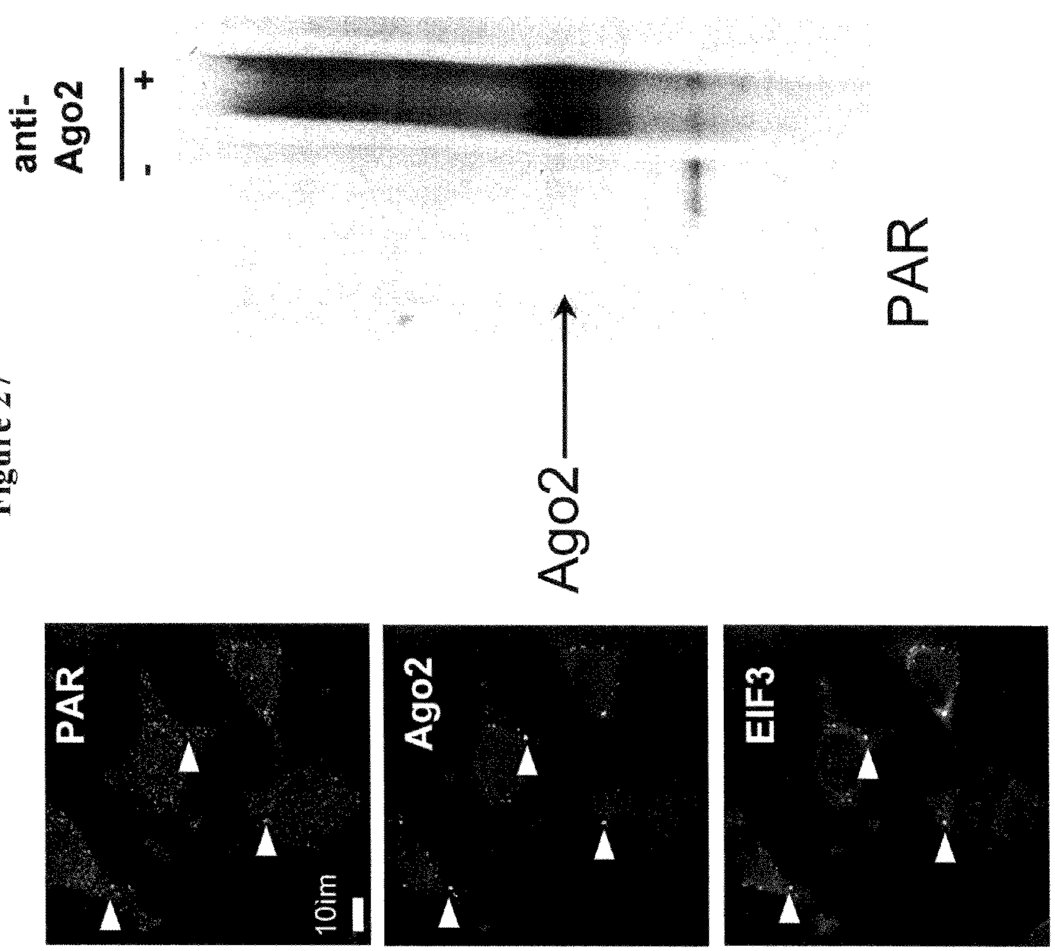
FIG. 27 (left panel) is a set of micrographs showing the localization of poly-ADP-ribose, and endogenous Ago2 and eIF3 in HeLa cells following treatment with 250 μM sodium arsenite for 30 minutes. The cells were imaged using fluorescently labeled anti-poly-ADP-ribose, anti-Ago2, and anti-eIF3 antibodies.

We have further discovered that PARP13 and PARG regulate the activity of RNAi and miRNA molecules in cells. Regulation of RNAi and miRNA activity in cells remains largely uncharacterized. One of the proteins implicated for a role in the regulation of RNAi and miRNA activity is Argonaut 2, a single-stranded RNAse. Using immunofluorescence microscopy we have observed that Argonaut 2 localizes to stress granules in HeLa cells treated with 250 μM sodium arsenite for 30 minutes (FIG. 27, left panel). In these experiments, cells were treated with sodium arsenite and stained using both antibodies against Argonaut 2 and eIF3 (a stress granule marker), and secondary fluorescently-labeled antibodies. The data show that Argonaut 2 is poly-ADP-ribosylated in HeLa cells following exposure to 250 μM sodium arsenite for 30 minutes (FIG. 27, right panel). In these experiments, cell lysate from cells treated with 250 μM sodium arsenite was immunoprecipitated with an anti-Argonaut 2 antibody, and the resulting immunoprecipitated proteins were immunoblotted using an anti-poly-ADP-ribose antibody. The results indicate that Argonaut 2 is localized to stress granules and poly-ADP-ribosylated under cellular stress conditions.

Figure 28:
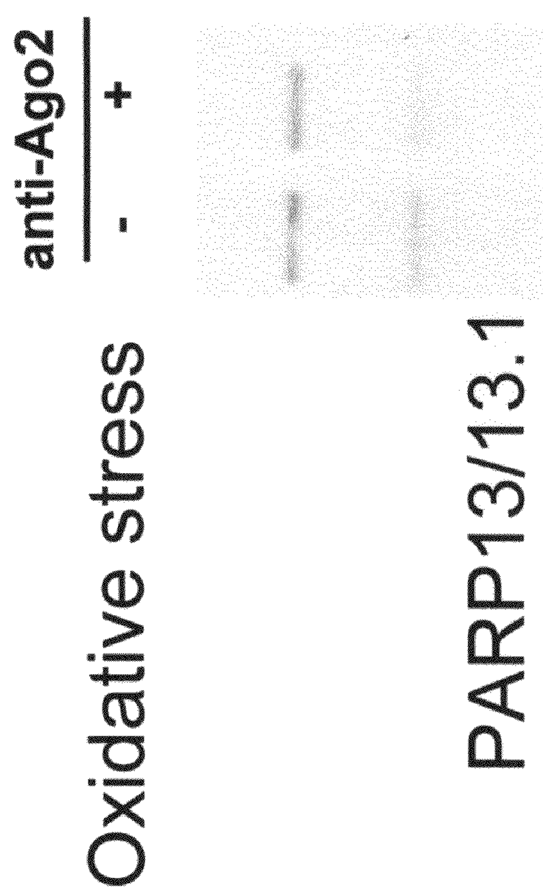
FIG. 28 is a picture of an immunoblot of a 4-12% SDS-PAGE gel containing proteins immunoprecipitated with an anti-Ago2 antibody from lysate from untransfected HeLa cells following treatment with 0 or 250 μM sodium arsenite for 30 minutes. The immunoblot was developed using a polyclonal anti-PARP13/13.1 antibody.

To determine whether one or more of the PARPs identified herein mediate the poly-ADP-ribosylation of Argonaut 2, immunoprecipitation experiments were performed on cell lysate from untransfected HeLa cells treated with 0 or 250 μM sodium arsenite for 30 minutes using an anti-Argonaut 2 antibody. The resulting immunoprecipitated proteins were immunoblotted using an anti-PARP13/13.1 antibody. The data show that PARP13/13.1 binds to Argonaut 2 under both normal (0 μM sodium arsenite) and stress conditions (250 μM sodium arsenite) (FIG. 28).

Figure 29:
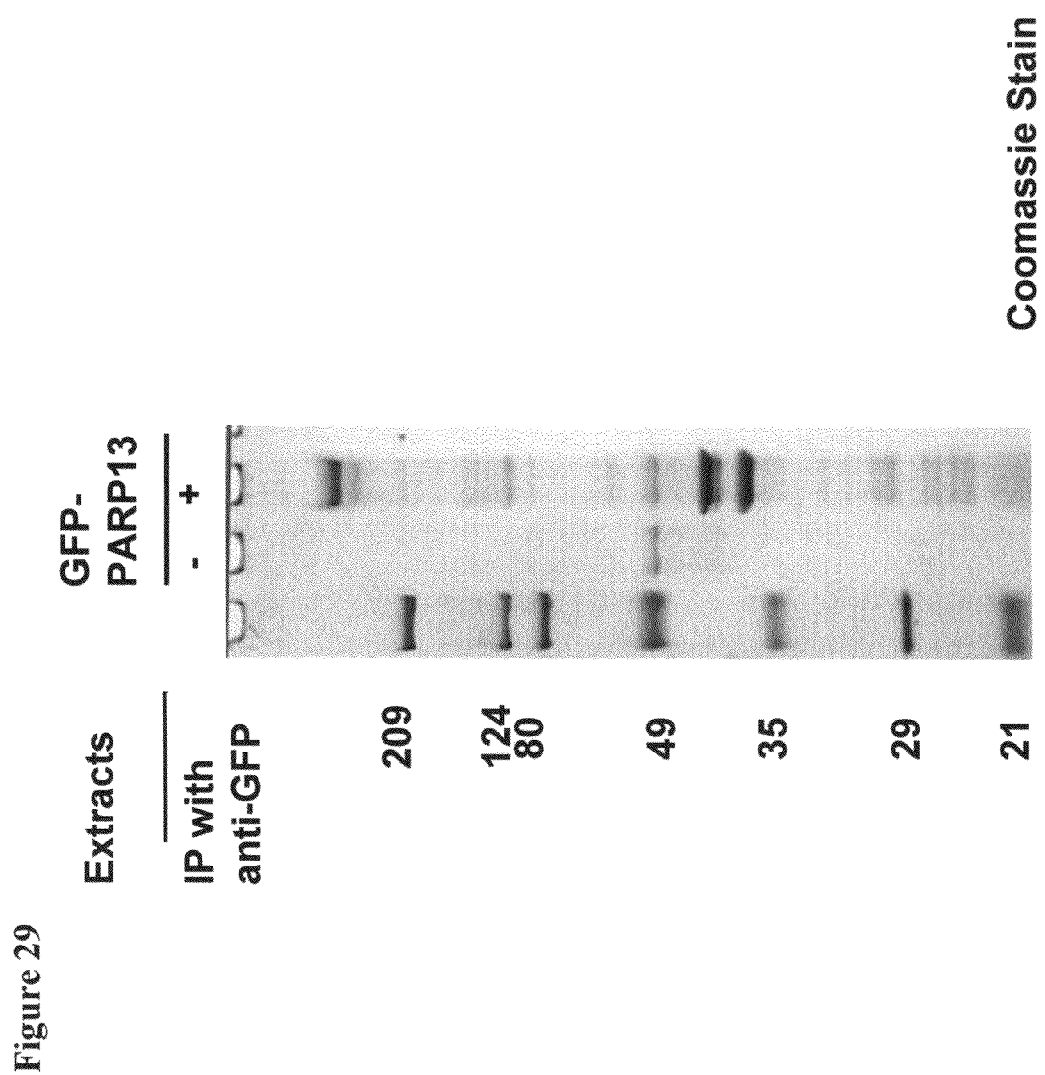
FIG. 29 is a picture of a Coomassie Blue-stained 4-12% SDS-PAGE gel containing proteins immunoprecipitated using an anti-GFP antibody from lysate from HeLa S3 cells transfected with a pEGFP-C1 plasmid expressing PARP13-GFP following treatment with 0 or 250 μM sodium arsenite for 30 minutes.
Figure 30:
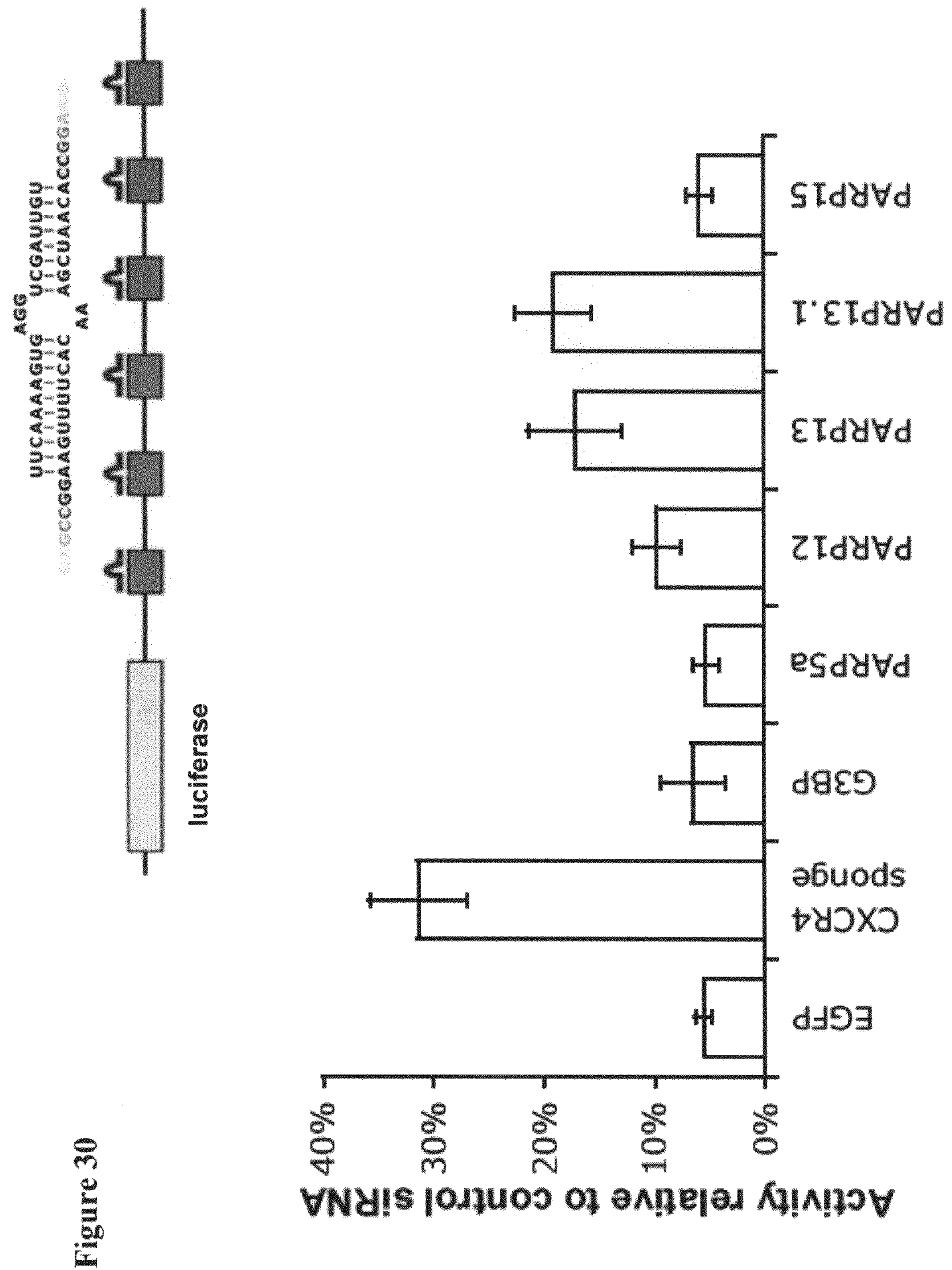
FIG. 30 is a graph showing the relative expression of luciferase in lysates from 293T cells transfected with a modified pGL4.72[hRlucCP]™ vector (Promega); 10 nM of vector-target RNAi (SEQ ID NOS: 38 and 39); and a pEGFP-C1 vector encoding EGFP, G3BP, PAPR5A, PARP12, PARP13, PARP13.1, or PARP15. Luciferase expression was measured in cell lysates at 48 hours post-transfection. The level of luciferase in treated cells is compared to the level of luciferase produced in cells transfected with the modified pGL4.72 [hRlucCP]™ vector alone. As another positive control, the level of luciferase produced from cells transfected with the modified pGL4.72[hRlucCP]™ vector and the vector-target RNAi is shown (CXCR4 sponge).
Figure 31:
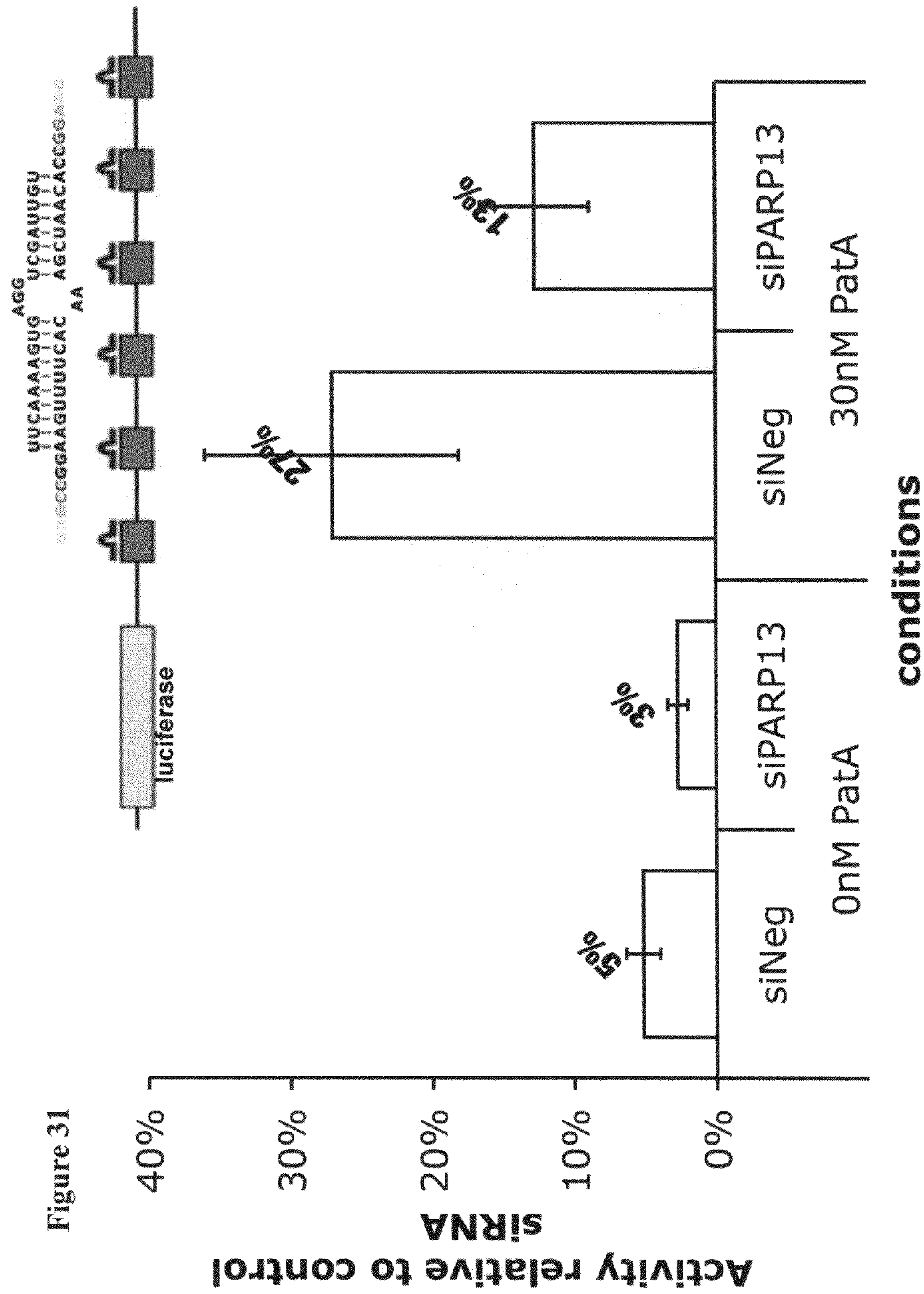
FIG. 31 is a graph showing the relative expression of luciferase in 293T cells transfected with a modified pGL4.72 [hRlucCP]™ vector and 20 nM of negative RNAi control for PARP13 siRNA (siNeg; All Stars Negative Control siRNA; Qiagen Catalog No. 1027280) or PARP13 siRNA (si-PARP13; GCUCACGGAACUAUGAGCUGAGUUU; SEQ ID NO: 40) following treatment with 0 or 30 nM pateamine A for 30 minutes. Luciferase expression was measured in cell lysates at 48 hours post-transfection.

To identify additional substrate proteins of PAPR13, immunoprecipitation experiments were performed on lysate from HeLa cells transfected with a pEGFP-C1 plasmid containing a sequence encoding a PARP13-GFP fusion protein following treatment with either 0 or 250 μM sodium arsenite for 30 minutes. The cell lysate was treated with an anti-GFP antibody and the resulting immunoprecipitated proteins were electrophoresed using SDS-PAGE. The data show that exposure to 250 μM sodium arsenite increases the number and identity of proteins that bind to the PARP13-GFP fusion protein (FIG. 29). The identification of the specific proteins co-immunoprecipitated with the PARP13-GFP fusion protein will help to further elucidate the role of PARP13 in cellular mechanisms, including its regulation of Argonaut 2 and its role in the regulation of miRNA and RNAi activity. Additional experiments were performed to determine the effect of PARP13 knockdown on miRNA activity. For these experiments, the pGL4.72[hRlucCP]™-vector assay (Promega) was used to measure RNAi activity in 293T cells. The pGL4.72[hRlucCP]™ vector contains a constitutively expressed firefly luciferase gene which is located upstream of several nucleic acid sequences targeted by an RNAi molecule. An increase in the activity of an RNAi molecule targeting the downstream 3' sequences of the vector results in a decrease in the amount of luciferase produced from the vector. In experiments to study the effect of PARP13 on miRNA activity, the pGL4.72[hRlucCP]™ vector was first engineered to contain 6 repeats of a sequence recognized by an RNAi molecule targeting the vector ("vector-target RNAi;" SEQ ID NOS: 38 and 39; GUUUUCACUCCAGCUAACACA and TTCAAAAGUGAGGUCGAUUGU, respectively). In a first experiment, cells were transfected with a modified pGL4.72[hRlucCP]™ vector and a pEGFP-C1 plasmid encoding EGFP (negative control), G3BP (negative control), PARP5a, PARP12, PARP13, PARP13.1, or PARP15; and 10 nM of the vector-target RNAi. In a positive control, the cells were transfected with the modified pGL4.72 [hRlucCP]™ vector and vector-target RNAi alone (CXCR4 sponge). Cells overexpressing PARP13 or PARP13.1 showed a 3-fold decrease in the level of miRNA-mediated repression compared to control cells (e.g., EGFP- and G3BP-overexpressing cells) (FIG. 30). In a second set of experiments, the ability of the vector-target RNAi to reduce the expression of luciferase was measured in 293T cells transfected with pGL4.72[hRlucCP]™ vector, 20 nM vector-target RNAi, and 20 nM of negative RNAi control for PARP13 siRNA (siNeg; AllStars Negative Control siRNA; Qiagen Catalog No. 1027280) or PARP13 siRNA (siPARP13; SEQ ID NO: 40) following treatment with 0 or 30 nM pateamine A for 2 hours. The data in FIG. 31 show that knockdown of PARP13 expression by siPARP13 results in an increase in the activity of the vector-target RNAi under stress conditions (i.e., 30 nM pateamine A) (FIG. 31). These data indicate that PARP13 activity in the cell has a negative effect on RNAi activity in the cell. This effect on RNAi activity may occur through the poly-ADP-ribosylation of Argonaut 2 by PARP13 or by the ability of PARP13 to modify or bind other proteins located within stress granules or proteins required for the assembly or disassembly of stress granules.

Experimental Methods

Immunoprecipitation experiments were performed using non-transfected HeLa cells following treatment with 0 or 250 μM sodium arsenite for 60 minutes using an anti-Argonaut 2 antibody. The resulting precipitated proteins were electrophoresed using 4-12% SDS-PAGE and immunoblotted using an anti-poly-ADP ribose antibody. Non-transfected HeLa cells treated with 250 μM sodium arsenite for 30 minutes were also stained for immunofluorescence microscopy using antibodies specific for Argonaut 2 and eIF3 (a marker of stress granules), and a secondary fluorescently-labeled antibody (Alexa Fluor 594 and 488 antibodies).

Additional co-immunoprecipitation experiments were performed using methods known in the art. In these experiments, HeLa cell lysate was prepared from cells treated with 0 or 250 μM sodium arsenite for 30 minutes, and the lysate subsequently immunoprecipitated with an anti-Argonaut 2 antibody. The resulting precipitated proteins were immunoblotted using-an anti-PARP13/13.1 antibody.

Experiments to identify additional proteins bound to a PARP13-GFP fusion protein were performed by transfecting HeLa S3 cells with a pEGFP-C1 plasmid encoding a PARP13-GFP fusion protein. The transfected cells were treated with 0 or 250 μM sodium arsenite for 30 minutes before lysis. The resulting cell lysate was immunoprecipitated with an anti-GFP antibody and the resulting precipitated proteins were electrophoresed using 4-12% SDS-PAGE and the resulting gel stained with Coomassie Blue.

Experiments to determine the effect of knockdown of PARP13 on miRNA and RNAi activity were performed using a modified pGL4.72[hRlucCP]™-vector assay (Promega). For these experiments, the pGL4.72[hRlucCP]™-vector was modified by placing six copies of a target sequence at a position 3' to the luciferase gene. RNAi molecules targeting the vector were designed to bind the six copies of the target sequence (SEQ ID NOS: 34 and 35). The modified pGL4.72 [hRlucCP]™-vector was introduced into 293T cells using Lipofectamine 2000 (Invitrogen) according to the manufacturer's instructions. In each experiment, the cells were further transfected (Lipofectamine 2000) with 10 or 20 nM of the vector-target RNAi alone or in combination with either 20 nM of a control RNAi molecule for the siRNA targeting PARP13 (siNeg) or an RNAi molecule targeting PARP13 (siPARG13), and the cells treated with 0 or 30 nM pateamine A for 60 minutes. Following 48-hours incubation, the level of luciferase protein production was measured using a luciferase assay kit (Promega). The data are shown as the relative level of luciferase protein produced in cells transfected with the modified vector alone in the absence of any RNAi treatment.

Experiments were also performed to determine the effect of overexpression of a PARP-GFP protein on the activity of miRNA using the modified pGL4.72[hRlucCP]™-vector assay described above. In these experiments, 293T cells were transfected with pEGFP-C1 expression vectors encoding EGFP, G3BP, PARP5A, PARP12, PARP13, PARP13.1, or PARP15; the modified pGL4.72[hRlucCP]™ vector, and 10 nM vector-targeting RNAi. As a positive control for RNAi activity, the cells were transfected with the modified pGL4.72 [hRlucCP]™ and the vector-target RNAi alone (CXCR4 sponge).

From the foregoing description, one skilled in the art can easily ascertain the essential characteristics of this invention; can make various changes and modifications of the invention to adapt it to various usages and conditions. Thus, other embodiments are also within the claims. All references cited herein are incorporated by reference in their entirety.

The invention claimed is:

1. A collection of PARP fusion proteins encoded by four or more nucleic acid sequences comprising:

(a) a PARP sequence at least 95% identical to a PARP selected from PARP1 (SEQ ID NOS: 1 or 2), PARP2 (SEQ ID NO: 3), PARP3 (SEQ ID NO: 4), PARP3 isoform 2 (PARP3.2; SEQ ID NO: 5), PARP3 isoform 3 (PARP3.3; SEQ ID NO: 6), PARP4 (SEQ ID NO: 7), PARP5a (Tankyrase 1) (SEQ ID NO: 8 or 9), PARP5b (Tankyrase 2) (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13 isoform 1 (PARP13.1; SEQ ID NO: 19), PARP13 isoform 2 (PARP13.2; SEQ ID NO: 20), PARP14 (SEQ ID NO: 21), PARP15 isoform 1 (PARP15.1; SEQ ID NO: 22), PARP15 isoform 2 (PARP15.2; SEQ ID NO: 23), and PARP16 (SEQ ID NO: 24); and (b) a polypeptide tag sequence.

2. The PARP fusion proteins of claim 1, wherein the polypeptide tag sequence is at the 5'-end of the PARP sequence in at least one of the four or more nucleic acid sequences.

3. The PARP fusion proteins of claim 1, wherein the polypeptide tag sequence comprises a nucleic acid sequence encoding a fluorescent protein.

4. The PARP fusion proteins of claim 3, wherein the fluorescent protein is a green fluorescent protein having at least 95% sequence identity to SEQ ID NO: 25.

5. The PARP fusion proteins of claim 1, wherein the polypeptide tag sequence comprises a nucleic acid sequence encoding a protease recognition sequence.

6. The PARP fusion proteins of claim 5, wherein the protease recognition sequence is a TEV protease recognition sequence of Glu-X-X-Tyr-X-Gln-Ser (SEQ ID NO: 26).

7. The PARP fusion proteins of claim 6, wherein the polypeptide tag sequence comprises a nucleic acid sequence encoding a ZZ-domain at least 95% identical to SEQ ID NO: 27 and a nucleic acid sequence encoding the TEV protease recognition sequence of Glu-X-X-Tyr-X-Gln-Ser (SEQ ID NO: 26), wherein the sequence encoding the TEV protease recognition sequence is located 3' of the sequence encoding the ZZ-domain.

8. The PARP fusion proteins of claim 1, wherein polypeptide tag sequence comprises a nucleic acid sequence encoding a ZZ-domain at least 95% identical to SEQ ID NO: 27.

9. The PARP fusion proteins of claim 1, wherein one of the 4 or more nucleic acid sequences encoding the PARP fusion proteins comprises at least 95% sequence identity to PARP5a (Tankyrase 1) (SEQ ID NO: 8).

10. The PARP fusion proteins of claim 1, wherein one of the 4 or more nucleic acid sequences encoding the PARP fusion proteins comprises at least 95% sequence identity to PARP11 (SEQ ID NO: 17).

11. The PARP fusion proteins of claim 1, wherein one of the 4 or more nucleic acid sequences encoding the PARP fusion proteins comprises at least 95% sequence identity to PARP13.1 (SEQ ID NO: 19).

12. The PARP fusion proteins of claim 1, wherein one of the 4 or more nucleic acid sequences encoding the PARP fusion proteins comprises at least 95% sequence identity to PARP16 (SEQ ID NO: 24).

13. A solid surface comprising at least four discrete locations, the at least four discrete locations comprising a different PARP fusion protein from one another, the PARP fusion proteins encoded by 4 or more nucleic acid sequences comprising:

(a) a PARP sequence at least 95% identical to a PARP selected from PARP1 (SEQ ID NOs: 1 or 2), PARP2 (SEQ ID NO: 3), PARP3 (SEQ ID NO: 4), PARP3 isoform 2 (PARP3.2; SEQ ID NO: 5), PARP3 isoform 3 (PARP3.3; SEQ ID NO: 6), PARP4 (SEQ ID NO: 7), PARP5a (Tankyrase 1)(SEQ ID NO: 8 or 9), PARP5b (Tankyrase 2) (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP 10.2 (SEQ ID NO: 16), PARP11 (SEQ ID NO: 17), PARP12 (SEQ ID NO: 18), PARP13 isoform 1 (PARP13.1; SEQ ID NO: 19), PARP13 isoform 2 (PARP13.2; SEQ ID NO: 20), PARP14 (SEQ ID NO: 21), PARP15 isoform 1 (PARP15.1; SEQ ID NO: 22), PARP15 isoform 2 (PARP15.2; SEQ ID NO: 23), and PARP16 (SEQ ID NO: 24); and (b) a polypeptide tag sequence.

14. The solid surface of claim 13, wherein the PARP fusion protein is attached to a bead.

15. The solid surface of claim 14, wherein the bead is magnetic.

16. The solid surface of claim 13, wherein at least eight wells comprise a different PARP fusion protein from one another, the PARP fusion proteins encoded by eight or more of the nucleic acid sequences.

17. The solid surface of claim 16, wherein at least 16 wells comprise a different PARP fusion protein from one another, the PARP fusion proteins encoded by 16 or more of the nucleic acid sequences.

18. The solid surface of claim 17, wherein at least 24 wells comprise a different PARP fusion protein from one another, the PARP fusion proteins encoded by all 24 of the nucleic acid sequences.

19. The solid surface of claim 13, wherein the PARP fusion proteins are encoded by the nucleic acid sequences comprising:

(a) a PARP sequence at least 95% identical to:

(i) PARP1 (SEQ ID NOs: 1 or 2), PARP2 (SEQ ID NO: 3), PARP4 (SEQ ID NO: 7), PARP5a (Tankyrase 1) (SEQ ID NO: 8 or 9), PARP5b (Tankyrase 2) (SEQ ID NO: 10), PARP6 (SEQ ID NO: 11), PARP7 (SEQ ID NO: 12), PARP8 (SEQ ID NO: 13), PARP9 (SEQ ID NO: 14), PARP12 (SEQ ID NO: 18), PARP14 (SEQ ID NO: 21), and PARP16 (SEQ ID NO: 24);

(ii) one PARP selected from PARP3 (SEQ ID NO: 4), PARP3 isoform 2 (PARP3.2; SEQ ID NO: 5), and PARP3 isoform 3 (PARP3.3; SEQ ID NO: 6);

(iii) one PARP selected from PARP10 (SEQ ID NO: 15) and PARP 10.2 (SEQ ID NO: 16);

(iii) one PARP selected from PARP13 isoform 1 (PARP13.1; SEQ ID NO: 19) and PARP13 isoform 2 (PARP13.2; SEQ ID NO: 20); and (iv) one PARP selected from PARP15 isoform 1 (PARP15.1; SEQ ID NO: 22) and PARP15 isoform 2 (PARP15.2; SEQ ID NO: 23); and (b) a polypeptide tag sequence.

20. The solid surface of claim 13, wherein the polypeptide tag sequence is at the 5'-end of the PARP sequence in at least one of the four or more nucleic acid sequences.

21. The solid surface of claim 13, wherein the polypeptide tag sequence is at the 5'-end of the PARP sequence in each of the four or more nucleic acid sequences.

22. The solid surface of claim 13, wherein the polypeptide tag sequence comprises a nucleic acid sequence encoding a fluorescent protein.

23. The solid surface of claim 22, wherein the fluorescent protein is a green fluorescent protein having at least 95% sequence identity to SEQ ID NO: 25.

24. The solid surface of claim 13, wherein the polypeptide tag sequence comprises a nucleic acid sequence encoding a protease recognition sequence.

25. The solid surface of claim 24, wherein the protease recognition sequence is a TEV protease recognition sequence of Glu-X-X-Tyr-X-Gln-Ser (SEQ ID NO: 26).

26. The solid surface of claim 25, wherein the polypeptide tag sequence comprises a nucleic acid sequence encoding a ZZ-domain at least 95% identical to SEQ ID NO: 27 and a nucleic acid sequence encoding the TEV protease recognition sequence of Glu-X-X-Tyr-X-Gln-Ser (SEQ ID NO: 26), wherein the sequence encoding the TEV protease recognition sequence is located 3' of the sequence encoding the ZZ-domain.

27. The solid surface of claim 13, wherein the polypeptide tag sequence comprises a nucleic acid sequence encoding a ZZ-domain at least 95% identical to SEQ ID NO: 27.

* * * * *

UNITED STATES PATENT AND TRADEMARK OFFICE

CERTIFICATE OF CORRECTION

PATENT NO. : 8,268,550 B2
APPLICATION NO. : 12/459212
DATED : September 18, 2012
INVENTOR(S) : Paul Chang et al.

It is certified that error appears in the above-identified patent and that said Letters Patent is hereby corrected as shown below:

Column 119, Claim 8, Lines 47-48, replace "wherein polypeptide" with --wherein the polypeptide--.

Column 120, Claim 13, Line 9, replace "(Tankyrase 1)(SEQ ID NO: 8 or 9)," with --(Tankyrase 1) (SEQ ID NO: 8 or 9),--.

Signed and Sealed this
Fifth Day of March, 2013

Teresa Stanek Rea
*Acting Director of the United States Patent and Trademark Office*